US008008325B2

(12) United States Patent
Buckman et al.

(10) Patent No.: US 8,008,325 B2
(45) Date of Patent: *Aug. 30, 2011

(54) PLASMA CARBOXYPEPTIDASE B INHIBITORS

(75) Inventors: Brad O. Buckman, Oakland, CA (US); Kumar Emayan, Berkeley, CA (US); Imadul Islam, Hercules, CA (US); Karen May, Napa, CA (US); Judi Bryant, Mill Valley, CA (US); Raju Mohan, Encinitas, CA (US); Christopher West, El Sobrante, CA (US); Shendong Yuan, San Ramon, CA (US)

(73) Assignee: Bayer Schering Pharma AG, Berlin (DE)

( * ) Notice: Subject to any disclaimer, the term of this patent is extended or adjusted under 35 U.S.C. 154(b) by 20 days.

This patent is subject to a terminal disclaimer.

(21) Appl. No.: 12/332,619

(22) Filed: Dec. 11, 2008

(65) Prior Publication Data

US 2009/0093520 A1    Apr. 9, 2009

Related U.S. Application Data

(62) Division of application No. 10/508,169, filed as application No. PCT/US03/08587 on Mar. 21, 2003, now Pat. No. 7,528,173.

(60) Provisional application No. 60/367,156, filed on Mar. 21, 2002.

(51) Int. Cl.
*A61K 31/445* (2006.01)
*C07D 211/00* (2006.01)

(52) U.S. Cl. ........................ 514/315; 546/184

(58) Field of Classification Search .................. 514/315; 546/184

See application file for complete search history.

(56) References Cited

U.S. PATENT DOCUMENTS

| | | | |
|---|---|---|---|
| 5,977,090 A | 11/1999 | Slusher et al. | |
| 6,011,021 A | 1/2000 | Slusher et al. | |
| 6,017,903 A | 1/2000 | Slusher et al. | |
| 6,046,180 A | 4/2000 | Jackson et al. | |
| 7,528,173 B2 * | 5/2009 | Buckman et al. | 514/634 |

FOREIGN PATENT DOCUMENTS

| | | |
|---|---|---|
| EP | 0 361 365 | 4/1990 |
| EP | 1 152 004 | 11/2001 |
| EP | 1 174 434 | 1/2002 |
| JP | 2-157260 | 6/1990 |
| JP | 4-30563 | 2/1992 |
| JP | 2001-527084 | 12/2001 |
| WO | WO 99/33849 | 4/1990 |
| WO | WO 94/06808 | 3/1994 |
| WO | WO 97/48400 | 12/1997 |
| WO | WO 97/49399 | 12/1997 |
| WO | WO 98/13044 | 4/1998 |
| WO | WO 98/53812 | 12/1998 |
| WO | WO 00/66152 | 11/2000 |
| WO | WO 00/66550 | 11/2000 |
| WO | WO 00/66557 | 11/2000 |
| WO | WO 03/027128 | 4/2003 |

OTHER PUBLICATIONS

Nishio et al., 2000, CAS: 134: 29339.*
Jackson et al., 1998, CAS: 128: 70764.*
Allen et al., 2000, CAS: 132:180639.*
Slusher et al., 1999, CAS: 131: 317798.*
Nishio et al., 1992, CAS: 117:7893.*
Barluenga et al., 1989, CAS: 110:192579.*
Nishio et al., 1988, CAS: 108:221659.*
Tachibana et al., 1987, CAS: 107: 165412.*
Calet et al., "Cobalt Carbonyl and Phase Transfer Catalyzed Carbonylation of Thiiranes", Organometallics, vol. 6, 1987, pp. 1625-1628.
Campbell., "The Synthesis of Phosphonate Esters, an Extension of the Mitsunobu Reaction", J. Org. Chem., vol. 57, 1992, pp. 6331-6335.
Inguimbert et al., Toward an Optimal Joint Recognition of the Subsites of Endothelin Converting Enzyme-1 (ECE-1), Angiotensin Converting Enzyme (ACE), and Neutral Endopeptidase (NEP), J. Med. Chem., vol. 45, 2002, pp. 1477-1486.
Takehiko Nishio, Photochemical Reactions of 4-Pyridinethiones and 9-acridinethiones with Alkenes, Journal of the Chemical Society, Perkin Transactions 1: Organic and Bio-Organic Chemistry, (1972-1999) (1987), 2 pages.
Takehiko Nishio et al., Photochemical reactions of N-acylbenzoxazole-2-thiones, Perkin 1, (2000), 1 page.
Takehiko Nishio, et al., Synthesis of indole derivatives by [2+2] photocycloaddition of indoline-2-thiones with alkenes and photodesulfurization of indoline-2-thiones, Helvetica Chimica Acta, (1997), 1 page.
Takehiko Nishio, et al., Photoaddition of benzoxazole-2-thiones with alkenes, Journal of the Chemical Society, Perkin Transactions 1: Organic and Bio-Organic Chemistry, (1996), 2 pages.
J.M. Gaullier, et al., Amino acid-pyrrole N-conjugates; a new class of antioxidants. II. Effectiveness of singlet oxygen quenching by luminescence measurements, Journal of Photochemistry and Photobiology, B: Biology, (1995), 1 page.
Law Ho, et al., New N-ethanethiol pyrroles as radioprotectors, European Journal of Medicinal Chemistry (1993), 1 page.
Takehiko, Nishio, et al., Photochemical reactions of benzothiazole-2-thiones, Journal of the Chemical Society, Perkin Transactions 1: Organic and Bio-Organic Chemistry (1972-1999), 1 page.

(Continued)

*Primary Examiner* — Rei-tsang Shiao
(74) *Attorney, Agent, or Firm* — Millen, White, Zelano & Branigan, P.C.

(57) ABSTRACT

Compounds of the following formula (I), for example:

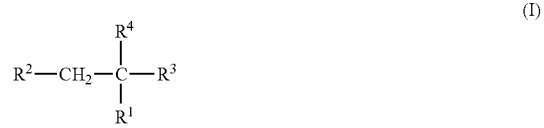

wherein $R^1$, $R^2$, $R^3$, and $R^4$ are described herein, are useful as inhibitors of plasma carboxypeptidase B. Pharmaceutical compositions containing these compounds, methods of using these compounds as antithrombotic agents and processes for synthesizing these compounds are also described herein.

14 Claims, No Drawings

OTHER PUBLICATIONS

Takehiko Nishio, Photocycloaddition of quinoxaline-2 (1H)-thiones to alekenes, Helvetica Chima Acta, (1992), 12 pages.

Eisuke Sato, et al., Photo-induced reactions. 114. Photochemistry of conjugated nitrogen-thiocarbonyl systems. VII. Photoaddition of quinoline-, isoquinoline- and phthalazinethione systems to olefins, Chemical & Pharmaceutical Bulletin, (1990), 1 page.

Michael P. Kirkup, A concise route to the oxathiazepine containing eudistomin skeleton and some carba-analogs, Tetrahedron Letters, (1989), 1 page.

Takehiki Nishio, Photochemical reactions of pyrimidinethiones with alkenes, Journal of the Chemical Society, Perkin Transactions 1: Organic and Bio-Organic Chemistry, (1972-1999), 2 pages.

Takehiko Nishio, Photo-induced carbon-carbon bond formation: reactions of 2-thiopyridones and 2-quinolinethiones with alkenes, Synthesis, (1986), 2 pages.

Nishiyama et al., "Agricultural and Biological Chemistry", XP-002543633, Abstract, 2009.

Konovalova, I.V. et al: "Reactions of 2,2,2-trifluoroethyl phosphites and isocyanatophosphites with carbonyl compounds", XP-002543634, Abstract, 1992.

Nomura et al., "Penicillins", XP-002543635, Abstract, 1976.

Konovalova, I.V et al, "(Diethoxy-phosphoryloxy)-phenyl-acetic acid methyl ester", XP-002543637, Abstract, 2009.

Pudovik et al, "2-(Diethoxy-phosphoryloxy)-2-phenyl-butyric acid ester", XP002543638, Abstract, 1974.

Pudowik et al., "Dimethyl-($\alpha$-ethoxycarbonyl-benzyl)-phosphat", SP-002543674, Abstract, 1988.

Delaney, N. G. et al., "Preparation of aminobenzoic and aminocyclohexanecarboxylic acids as neutral compositions containing them," 1991, Accession Number: 1991:121755.

Klein, J. et al., "Decarboxylation of alpha-arylcinnamic acids," Israel Journal of Chemistry, 1968, vol. 6, No. 5, pp. 701-712, Accession Numbers: 1969:491009.

Oonishi, H. et al., "Preparation of $\beta$-mercaptocarboxylic acids by hydrolysis of mercaptonitriles," Jpn. Kokai Tokkyo Koho, 1993, Accession No. : 1993:168704.

Valla, a. et al., "Preparation of pyrrole derivatives as antioxidants and as cosmetic materials," Centre National de la Recherche Scientifique, 1991, Accession Number: 1991:185259.

* cited by examiner

PLASMA CARBOXYPEPTIDASE B INHIBITORS

This application is a divisional application of U.S. application Ser. No. 10/508,169, filed on Apr. 22, 2005, which was the National Stage of International Application No. PCT/US03/08587, filed Mar. 21, 2003, which claimed the benefit of U.S. Provisional Application No. 60/367,156, filed Mar. 21, 2002.

FIELD OF THE INVENTION

The invention relates to plasma carboxypeptidase B inhibitors and their use as anti-thrombotic agents. This invention also relates to methods of using such inhibitors as anti-thrombotic agents and to pharmaceutical compositions containing such inhibitors.

BACKGROUND OF THE INVENTION

The fibrinolytic system removes fibrin clots from the circulation in order to maintain blood vessel patency. It also mediates the activation of metalloproteases which degrade extracellular matrix proteins. The fibrinolytic system therefore plays an important role in wound healing, cell migration, and cancer invasion. Abnormalities in the fibrinolytic system can lead to pathological conditions ranging from thrombosis and hemorrhage to atherosclerosis and tumor metastasis. The molecular components of the fibrinolytic system have been extensively characterized, and consist of plasminogen, plasminogen activators and their various inhibitors.

The first step in fibrinolysis is generation of a limited amount of plasmin, an active serine protease, from Glu-plasminogen by a plasminogen activator. Glu-plasminogen, a 92 kDa plasma protein, consists of a preactivation peptide, five kringle domains and the protease domain, and binds to fibrin and a number of other proteins through lysine-binding and aminohexyl-binding sites present in the kringle domains. There are two physiological plasminogen activators; tissue-type plasminogen activator (t-PA) and urokinase-type plasminogen activator (u-PA). t-PA plays the more important role in fibrinolysis in plasma while u-PA exerts its main functions in tissues. When both t-PA and Glu-plasminogen bind to the internal lysine and arginine residues of fibrin, the affinity of t-PA for plasminogen is increased by two orders of magnitude. The fibrin surface allows formation of a ternary complex between the enzyme and its substrate, resulting in more efficient conversion of Glu-plasminogen to plasmin by t-PA. Thus, on the clot surface, plasmin initiates clot lysis by proteolytic cleavage of internal lysine residues in the Aα-chain of fibrin.

Fibrinolysis is accelerated by several mechanisms. The major feedback mechanism involves newly exposed C-terminal lysine residues of the Aα-chain of fibrin following its partial degradation by plasmin. Since both Glu-plasminogen and t-PA have high affinities for these newly-exposed C-terminal lysine residues, this leads to increased binding of Glu-plasminogen and t-PA to fibrin. Other mechanisms of acceleration of lysis include plasmin-induced conversion of Glu-plasminogen to Lys-plasminogen, which has a greater fibrin affinity, and conversion of single-chain t-PA to two-chain t-PA by plasmin, which has both an increased binding to fibrin and higher turnover rate. The overall result is the amplification of plasmin production at the site of the clot, enhancing clot dissolution.

Regulation of the fibrinolytic system occurs at the level of plasmin and plasminogen activators. α2-Antiplasmin is the primary inhibitor of free plasmin in plasma. It forms a stable and irreversible complex with plasmin. The initial reaction is facilitated by the interaction between the lysine binding site of plasmin and lysine residues in the C-terminal region of α2-antiplasmin. The rapid inactivation of free plasmin by α2-antiplasmin without inhibition of fibrin-bound plasmin prevents excessive systemic proteolysis of circulating proteins such as fibrinogen, and coagulation factors V and VIII, and restricts plasmin action to the site of fibrin deposition. Plasminogen activator inhibitor-1 (PAI-1) functions as the main inhibitor of plasminogen activators in plasma by forming a SDS-stable complex with both free and fibrin-bound t-PA. Recently, another protein which exhibits carboxypeptidase B-like activity has been shown to modulate the process of fibrinolysis. This protein, plasma carboxypeptidase B, inhibits the amplification of plasmin production by removing the C-terminal lysine residues from partially degraded fibrin, thereby slowing down fibrinolysis.

Plasma carboxypeptidase B (EC 3.4.17.20), also known as plasma carboxypeptidase U or thrombin-activatable fibrinolysis inhibitor (TAFI), is a 60 kDa glycoprotein that circulates in plasma at ~75 nM. The protein consists of a 22-amino acid signal peptide, a 92-amino acid activation peptide and a 309-amino acid catalytic domain, which shows 50% identity with the protease domain of pancreatic carboxypeptidase A and B (pancreatic CPA and pancreatic CPB). The presence of aspartic acid at position 256 of the catalytic domain suggests that it is a basic carboxypeptidase.

Similar to pancreatic CPA and pancreatic CPB, plasma carboxypeptidase B can be activated in vitro by high concentrations of trypsin, thrombin, or plasmin via cleavage at Arg92. Activated plasma carboxypeptidase B is a zinc metalloprotease that hydrolyzes synthetic and natural peptides with C-terminal arginines and lysines, with a preference for arginine. It is inhibited by a synthetic molecule such as guanidinoethyl-mercaptosuccinic acid (GEMSA) and a naturally occurring carboxypeptidase inhibitor from potato (CPI).

Unlike pancreatic CPA and CPB, plasma carboxypeptidase activated with trypsin or thrombin is very unstable since it undergoes conformational changes that result in thermal instability. This thermal instability in turn facilitates the proteolytic cleavage of TAFIa at Arg302 by these activators that result in the loss of a substrate binding site. The stability of the activated enzyme is enhanced when its catalytic site is occupied with inhibitors such as GEMSA and aminohexanoic acid. The physiological activator of plasma carboxypeptidase B probably is a thrombin/thrombomodulin complex. Compared to activation by free thrombin, thrombomodulin (both soluble and cell surface) increases the catalytic efficiency of the activation of plasma carboxypeptidase B by a factor of 1250, almost exclusively through its effect on kcat. Furthermore, thrombomodulin protects activated plasma carboxypeptidase B by inhibiting the cleavage of Arg302 by free thrombin.

Activated plasma carboxypeptidase B prolongs the lysis time of clots formed in the presence of Glu-plasminogen up to three-fold as measured by a clot lysis assay using purified protein components. This effect is dose-dependent with the half maximal effect obtained at a plasma carboxypeptidase B concentration of 1 nM. Since the concentration of circulating plasma carboxypeptidase B is about 75 nM, a sufficient amount of the active enzyme can be generated in plasma to modulate fibrinolysis. In a plasma clot lysis assay, activation of plasma carboxypeptidase B by the thrombin/thrombomodulin complex results in inhibition of t-PA-induced lysis. Furthermore, this prolongation was abolished when activation of plasma carboxypeptidase B was inhibited with either monoclonal anti-plasma carboxypeptidase B antibody or anti-thrombomodulin antibody. The known inhibitors of carboxypeptidase B, CPI and GEMSA, also blocked the inhibitory effect of plasma carboxypeptidase B on clot lysis.

In vivo, the effect of activated plasma carboxypeptidase B has been reported in a number of animal models using CPI. Minnema, M. C. et al. (*J. Clin. Invest.* (1998), Vol. 101, pp. 10-14) demonstrated that incorporation of CPI or anti-Factor XI antibody in the thrombus at the time of its formation resulted in a two-fold increase in the rate of endogenous fibrinolysis compared with the control in a rabbit jugular vein thrombolysis model (ref). Using a rabbit arterial thrombosis model, Klement et al. (*Blood* (1998), Vol. 92 (Supplement 1), p. 709a) showed that systemic administration of CPI with t-PA resulted in shortening of reperfusion time and longer duration of patency of the occluded vessel compared with t-PA only. Co-administration of CPI strongly inhibited thrombus growth. Similar effects of plasma carboxypeptidase on t-PA-induced thrombolysis were also reported in a rabbit arterio-venous shunt model and in a rabbit jugular vein thrombolysis model in house (see Refino, C. J. et al., *Fibrinolysis & Proteolysis* (1998), 12 (Supplement 1), Abstract No. 29). Furthermore, prevention of venous thrombosis in the presence of a TAFI inhibitor was observed in both rabbit and rat model (see Refino, supra; Nerme, V. et al, *Fibrinolysis & Proteolysis* (2000), 14 (Supplement 1), Abstract No. 69; and Muto, Y. et al., *Fibrinolysis & Proteolysis* (2000), 14 (Supplement 1), Abstract No. 70).

These in vivo studies together with in vitro clot lysis assays provide accumulating evidence that plasma carboxypeptidase B is involved in the physiological regulation of fibrinolysis/thrombolysis. There exists, therefore, a need for effective inhibitors of plasma carboxypeptidase B in order to enhance fibrinolysis/thrombolysis as needed.

SUMMARY OF THE INVENTION

The compounds of the invention are inhibitors of plasma carboxypeptidase B and are therefore useful in treating disease-states characterized by thrombotic activity and in so doing are useful as antithrombotic agents in the treatment and prevention of thrombosis.

Accordingly, in one aspect, the invention is directed to compounds of the following formula (I):

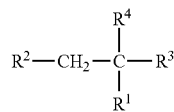

(I)

wherein:
$R^1$ is hydrogen, alkyl, alkenyl, aralkyl, or aralkenyl;
$R^2$ is —SH, —S—C(O)—$R^8$, —P(O)(O$R^5$)$_2$, —P(O)(O$R^5$)$R^6$, —P(O)(O$R^5$)—$R^7$—N($R^6$)$_2$, —P(O)(O$R^5$)—$R^7$—C(O)—$R^8$, —P(O)(O$R^5$)—$R^7$—N($R^5$)—C(O)O$R^8$, —P(O)(O$R^5$)—$R^7$—N($R^5$)—C(O)—$R^7$—N($R^5$)—C(O)O$R^8$, —P(O)(O$R^5$)—$R^7$—N($R^5$)—S(O)$_2$—$R^9$, or —P(O)(O$R^5$)—$R^7$—N($R^5$)—C(S)—N($R^6$)$_2$;
$R^3$ is tetrazole, —C(O)O$R^6$, —C(O)O—$R^7$—OC(O)$R^5$, —S(O)O$R^5$, —S(O)$_2$O$R^5$, —P(O)(O$R^5$)$_2$, —P(O)(O$R^5$)$R^6$, or —B(O$R^5$)$_2$;
$R^4$ is aryl optionally substituted by one or more substituents selected from the group consisting of alkyl, halo, haloalkyl, haloalkoxy, mercapto, alkylthio, phenyl, cycloalkyl, nitro, cyano, —O$R^6$, —N($R^6$)$_2$, —$R^7$—N($R^6$)$_2$, —N($R^6$)—C(O)O$R^8$, —$R^7$—N($R^6$)—C(O)O$R^8$, —N($R^6$)—C(O)—$R^6$, —$R^7$—N($R^6$)—C(O)—$R^6$, —C(O)—N($R^6$)$_2$, —C(O)—$R^7$—N($R^6$)$_2$, —N($R^5$)—C(N$R^5$)—N($R^5$)$_2$, —N($R^5$)—C(O)—N($R^6$)$_2$ and —N($R^5$)—C(O)—$R^7$—N($R^6_2$);

or $R^4$ is N-heterocyclyl wherein a carbon atom in the N-heterocyclyl may be optionally substituted by alkyl, halo, nitro, cyano, —N($R^6$)$_2$, —$R^7$—N($R^6$)$_2$, —N($R^6$)—C(O)O$R^8$, —$R^7$—N($R^6$)—C(O)O$R^8$, —N($R^6$)—C(O)—$R^6$, —$R^7$—N($R^6$)—C(O)—$R^6$, —C(O)—N($R^6$)$_2$, —C(O)—$R^7$—N($R^6$)$_2$, —N($R^5$)—C(N$R^5$)—N($R^5$)$_2$, —N($R^5$)—C(O)—N($R^6$)$_2$ or —N($R^5$)—C(O)—$R^7$—N($R^6_2$), or wherein a nitrogen atom in the N-heterocyclyl may be optionally substituted by —C(N$R^5$)—N($R^5$)$_2$, —C(N$R^5$)—$R^6$, —C(O)—N($R^6$)$_2$ or —C(O)—$R^7$—N($R^6$)$_2$;

each $R^5$ is independently hydrogen, alkyl or aralkyl;
each $R^6$ is independently hydrogen, alkyl, alkenyl, alkynyl, aryl, aralkyl or aralkenyl;
each $R^7$ is independently cycloalkylene (optionally substituted by alkyl), a straight or branched alkylene chain (optionally substituted by hydroxy, mercapto, alkylthio, aryl, cycloalkyl, —N($R^6$)$_2$, —C(O)O$R^6$, or —C(O)N($R^6$)$_2$), or a straight or branched alkenylene chain (optionally substituted by hydroxy, mercapto, alkylthio, aryl, cycloalkyl, —N($R^6$)$_2$, —C(O)O$R^6$, or —C(O)N($R^6$)$_2$);
each $R^8$ is independently alkyl, alkenyl, aryl, aralkyl or aralkenyl; and
$R^9$ is —$R^7$N($R^6$)C(O)O$R^8$, haloalkyl, alkyl (optionally substituted by hydroxy, alkoxy, aralkoxy, haloalkoxy, cyano, nitro, —N($R^6$)$_2$, —C(O)O$R^6$, —C(O)N($R^6$)$_2$ or —N($R^6$)C(O)$R^6$), alkenyl (optionally substituted by hydroxy, alkoxy, haloalkoxy, cyano, nitro, —N($R^6$)$_2$, —C(O)O$R^6$, —C(O)N($R^6$)$_2$ or —N($R^6$)C(O)$R^6$), aryl (optionally substituted by alkyl, aryl, aralkyl, hydroxy, alkoxy, cyano, nitro, halo, haloalkoxy, —N($R^6$)$_2$, —C(O)O$R^6$, —C(O)N($R^6$)$_2$ or —N($R^6$)C(O)$R^6$), aralkyl (wherein the aryl group is optionally substituted by alkyl, aryl, aralkyl, hydroxy, alkoxy, cyano, nitro, halo, haloalkoxy, —N($R^6$)$_2$, —C(O)O$R^6$, —C(O)N($R^6$)$_2$ or —N($R^6$)C(O)$R^6$), aralkenyl (wherein the aryl group is optionally substituted by alkyl, aryl, aralkyl, hydroxy, alkoxy, cyano, nitro, halo, haloalkoxy, —N($R^6$)$_2$, —C(O)O$R^6$, —C(O)N($R^6$)$_2$ or —N($R^6$)C(O)$R^6$), or N-heterocyclyl (optionally substituted by alkyl, aryl, aralkyl, hydroxy, alkoxy, cyano, nitro, halo, haloalkoxy, —N($R^6$)$_2$, —C(O)O$R^6$, —C(O)N($R^6$)$_2$ or —N($R^6$)C(O)$R^6$);

provided that when $R^3$ is —C(O)OH or when $R^4$ is a substituted aryl or substituted N-heterocyclyl, $R^2$ can not be —P(O)(O$R^5$)—$R^7$—N(H)—C(O)O$R^8$ or —P(O)(O$R^5$)—$R^7$—N(H)—C(O)—$R^7$—N($R^5$)—C(O)O$R^8$;

as a single stereoisomer, a mixture of stereoisomers, or as a racemic mixture of stereoisomers;
or a pharmaceutically acceptable salt thereof.

In another aspect, the invention is directed to compounds of the following formula (II):

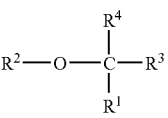

(II)

wherein:
$R^1$ is hydrogen, alkyl, alkenyl, aryl or aralkenyl;
$R^2$ is —P(O)(O$R^5$)$_2$, —P(O)(O$R^5$)$R^6$, —P(O)(O$R^5$)—$R^7$—N($R^6$)$_2$, —P(O)(O$R^5$)—$R^7$—C(O)—$R^8$, —P(O)(O$R^5$)—

$R^7$—N($R^5$)—C(O)O$R^8$, —P(O)(O$R^5$)—$R^7$—N($R^5$)—C(O)—$R^7$—N($R^5$)—C(O)O$R^8$, —P(O)(O$R^5$)—$R^7$—N($R^5$)—S(O)$_2$—$R^9$, or —P(O)(O$R^5$)—$R^7$—N($R^5$)—C(S)—N($R^6$)$_2$;

$R^3$ is tetrazole, —C(O)O$R^6$, —C(O)O—$R^7$—OC(O)$R^5$, —S(O)O$R^5$, —S(O)$_2$O$R^5$, —P(O)(O$R^5$)$_2$, —P(O)(O$R^5$)$R^6$, or —B(O$R^5$)$_2$;

$R^4$ is aryl optionally substituted by one or more substituents selected from the group consisting of alkyl, halo, haloalkyl, haloalkoxy, mercapto, alkylthio, phenyl, cycloalkyl, nitro, cyano, —O$R^6$, —N($R^6$)$_2$, —$R^7$—N($R^6$)$_2$, —N($R^6$)—C(O)O$R^8$, —$R^7$—N($R^6$)—C(O)O$R^8$, —N($R^6$)—C(O)—$R^6$, —$R^7$—N($R^6$)—C(O)—$R^6$, —C(O)—N($R^6$)$_2$, —C(O)—$R^7$—N($R^6$)$_2$, —N($R^5$)—C(N$R^5$)—N($R^5$)$_2$, —N($R^5$)—C(O)—N($R^6$)$_2$ and —N($R^5$)—C(O)—$R^7$—N($R^6_2$);

or $R^4$ is N-heterocyclyl wherein a carbon atom in the N-heterocyclyl may be optionally substituted by alkyl, halo, nitro, cyano, —N($R^6$)$_2$, —$R^7$—N($R^6$)$_2$, —N($R^6$)—C(O)O$R^8$, —$R^7$—N($R^6$)—C(O)O$R^8$, —N($R^6$)—C(O)—$R^6$, —$R^7$—N($R^6$)—C(O)—$R^6$, —C(O)—N($R^6$)$_2$, —C(O)—$R^7$—N($R^6$)$_2$, —N($R^5$)—C(N$R^5$)—N($R^5$)$_2$, —N($R^5$)—C(O)—N($R^6$)$_2$ or —N($R^5$)—C(O)—$R^7$—N($R^6_2$), or wherein a nitrogen atom in the N-heterocyclyl may be optionally substituted by —C(N$R^5$)—N($R^5$)$_2$, —C(N$R^5$)—$R^6$, —C(O)—N($R^6$)$_2$ or —C(O)—$R^7$—N($R^6$)$_2$;

each $R^5$ is independently hydrogen, alkyl or aralkyl;

each $R^6$ is independently hydrogen, alkyl, alkenyl, alkynyl, aryl, aralkyl or aralkenyl;

each $R^7$ is independently cycloalkylene (optionally substituted by alkyl), a straight or branched alkylene chain (optionally substituted by hydroxy, mercapto, alkylthio, aryl, cycloalkyl, —N($R^6$)$_2$, —C(O)O$R^6$, or —C(O)N($R^6$)$_2$), or a straight or branched alkenylene chain (optionally substituted by hydroxy, mercapto, alkylthio, aryl, cycloalkyl, —N($R^6$)$_2$, —C(O)O$R^6$, or —C(O)N($R^6$)$_2$);

each $R^8$ is independently alkyl, alkenyl, aryl, aralkyl or aralkenyl; and $R^9$ is —$R^7$N($R^6$)C(O)O$R^8$, haloalkyl, alkyl (optionally substituted by hydroxy, alkoxy, aralkoxy, haloalkoxy, cyano, nitro, —N($R^6$)$_2$, —C(O)O$R^6$, —C(O)N($R^6$)$_2$ or —N($R^6$)C(O)$R^6$), alkenyl (optionally substituted by hydroxy, alkoxy, haloalkoxy, cyano, nitro, —N($R^6$)$_2$, —C(O)O$R^6$, —C(O)N($R^6$)$_2$ or —N($R^6$)C(O)$R^6$), aryl (optionally substituted by alkyl, aryl, aralkyl, hydroxy, alkoxy, cyano, nitro, halo, haloalkoxy, —N($R^6$)$_2$, —C(O)O$R^6$, —C(O)N($R^6$)$_2$ or —N($R^6$)C(O)$R^6$), aralkyl (wherein the aryl group is optionally substituted by alkyl, aryl, aralkyl, hydroxy, alkoxy, cyano, nitro, halo, haloalkoxy, —N($R^6$)$_2$, —C(O)O$R^6$, —C(O)N($R^6$)$_2$ or —N($R^6$)C(O)$R^6$), aralkenyl (wherein the aryl group is optionally substituted by alkyl, aryl, aralkyl, hydroxy, alkoxy, cyano, nitro, halo, haloalkoxy, —N($R^6$)$_2$, —C(O)O$R^6$, —C(O)N($R^6$)$_2$ or —N($R^6$)C(O)$R^6$), or N-heterocyclyl (optionally substituted by alkyl, aryl, aralkyl, hydroxy, alkoxy, cyano, nitro, halo, haloalkoxy, —N($R^6$)$_2$, —C(O)O$R^6$, —C(O)N($R^6$)$_2$ or —N($R^6$)C(O)$R^6$);

provided that when $R^3$ is —C(O)OH or when $R^4$ is a substituted aryl or substituted N-heterocyclyl, $R^2$ can not be —P(O)(O$R^5$)—$R^7$—N(H)—C(O)O$R^8$ or —P(O)(O$R^5$)—$R^7$—N(H)—C(O)—$R^7$—N($R^5$)—C(O)O$R^8$;

as a single stereoisomer, a mixture of stereoisomers, or as a racemic mixture of stereoisomers;

or a pharmaceutically acceptable salt thereof.

In another aspect, the invention is directed to compounds of formula (III):

wherein:

X is —CH$_2$— or —O—;

$R^1$ is hydrogen, alkyl, alkenyl, aryl or aralkenyl;

$R^2$ is —P(O)(O$R^5$)—$R^7$—N($R^5$)—C(O)$R^6$, —P(O)(O$R^5$)—$R^7$—N($R^5$)—C(O)O$R^8$ or —P(O)(O$R^5$)—$R^7$—N($R^5$)—C(O)—$R^7$—N($R^5$)—C(O)O$R^8$, $R^3$ is —C(O)OH;

$R^4$ is aryl optionally substituted by one or more substituents selected from the group consisting of alkyl, halo, haloalkyl, haloalkoxy, mercapto, alkylthio, phenyl, cycloalkyl, nitro, cyano, —O$R^6$, —N($R^6$)$_2$, —$R^7$—N($R^6$)$_2$, —N($R^6$)—C(O)O$R^8$, —$R^7$—N($R^6$)—C(O)O$R^8$, —N($R^6$)—C(O)—$R^6$, —$R^7$—N($R^6$)—C(O)—$R^6$, —C(O)—N($R^6$)$_2$, —C(O)—$R^7$—N($R^6$)$_2$, —N($R^5$)—C(N$R^5$)—N($R^5$)$_2$, —N($R^5$)—C(O)—N($R^6$)$_2$ and —N($R^5$)—C(O)—$R^7$—N($R^6_2$);

or $R^4$ is N-heterocyclyl wherein a carbon atom in the N-heterocyclyl may be optionally substituted by alkyl, halo, nitro, cyano, —N($R^6$)$_2$, —$R^7$—N($R^6$)$_2$, —N($R^6$)—C(O)O$R^8$, —$R^7$—N($R^6$)—C(O)O$R^8$, —N($R^6$)—C(O)—$R^6$, —$R^7$—N($R^6$)—C(O)—$R^6$, —C(O)—N($R^6$)$_2$, —C(O)—$R^7$—N($R^6$)$_2$, —N($R^5$)—C(N$R^5$)—N($R^5$)$_2$, —N($R^5$)—C(O)—N($R^6$)$_2$ or —N($R^5$)—C(O)—$R^7$—N($R^6_2$), or wherein a nitrogen atom in the N-heterocyclyl may be optionally substituted by —C(N$R^5$)—N($R^5$)$_2$, —C(N$R^5$)—$R^6$, —C(O)—N($R^6$)$_2$ or —C(O)—$R^7$—N($R^6$)$_2$;

each $R^5$ is independently hydrogen, alkyl or aralkyl;

each $R^6$ is independently hydrogen, alkyl, alkenyl, alkynyl, aryl, aralkyl or aralkenyl;

each $R^7$ is independently cycloalkylene (optionally substituted by alkyl), a straight or branched alkylene chain (optionally substituted by hydroxy, mercapto, alkylthio, aryl, cycloalkyl, —N($R^6$)$_2$, —C(O)O$R^6$, or —C(O)N($R^6$)$_2$), or a straight or branched alkenylene chain (optionally substituted by hydroxy, mercapto, alkylthio, aryl, cycloalkyl, —N($R^6$)$_2$, —C(O)O$R^6$, or —C(O)N($R^6$)$_2$); and each $R^8$ is independently alkyl, alkenyl, aryl, aralkyl or aralkenyl;

as a single stereoisomer, a mixture of stereoisomers, or as a racemic mixture of stereoisomers;

or a pharmaceutically acceptable salt thereof.

In another aspect, the invention is directed to pharmaceutical compositions useful in treating a mammal, preferably a human, having a disease-state characterized by thrombotic activity, which compositions comprise a compound of formula (I), a compound of formula (II), or a compound of formula (III) as described above and a pharmaceutically acceptable excipient.

In another aspect, the invention is directed to methods of treating a mammal, preferably a human, having a disease-state characterized by thrombotic activity, which methods comprise administering to a mammal, preferably a human, having a disease-state characterized by thrombotic activity a therapeutically effective amount of a compound of formula (I), a compound of formula (II), or a compound of formula (III) as described above.

DETAILED DESCRIPTION OF THE INVENTION

A. Definitions

As used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, 1,1-dimethylethyl (t-butyl), and the like. Unless stated otherwise specifically in the specification, the alkyl radical may be optionally substituted by hydroxy, alkoxy, aryloxy, haloalkoxy, cyano, nitro, mercapto, alkylthio, cycloalkyl, $-N(R^6)_2$, $-C(O)OR^6$, $-C(O)N(R^6)_2$ or $-N(R^6)-C(O)-R^6$ where each $R^6$ is as defined in the Summary of the Invention. Unless stated otherwise specifically in the specification, it is understood that for radicals, as defined below, that contain a substituted alkyl group that the substitution can occur on any carbon of the alkyl group.

"Alkoxy" refers to a radical of the formula $-OR_a$ where $R_a$ is an alkyl radical as defined above, e.g., methoxy, ethoxy, n-propoxy, 1-methylethoxy (iso-propoxy), n-butoxy, n-pentoxy, 1,1-dimethylethoxy (t-butoxy), and the like. Unless stated otherwise specifically in the specification, it is understood that for radicals, as defined below, that contain a substituted alkoxy group that the substitution can occur on any carbon of the alkoxy group. The alkyl radical in the alkoxy radical may be optionally substituted as described above.

"Alkylthio" refers to a radical of the formula $-SR_a$ where $R_a$ is an alkyl radical as defined above, e.g., methylthio, ethylthio, n-propylthio, 1-methylethylthio (iso-propylthio), n-butylthio, n-pentylthio, 1,1-dimethylethylthio (t-butylthio), and the like. Unless stated otherwise specifically in the specification, it is understood that for radicals, as defined below, that contain a substituted alkylthio group that the substitution can occur on any carbon of the alkylthio group. The alkyl radical in the alkylthio radical may be optionally substituted as described above.

"Alkenyl" refers to a straight or branched hydrocarbon chain radical consisting solely of carbon and hydrogen atoms, containing at least one double bond, having from two to eight carbon atoms, and which is attached to the rest of the molecule by a single bond or a double bond, e.g., ethenyl, prop-1-enyl, but-1-enyl, pent-1-enyl, penta-1,4-dienyl, and the like. Unless stated otherwise specifically in the specification, the alkenyl radical may be optionally substituted by hydroxy, alkoxy, haloalkoxy, cyano, nitro, mercapto, alkylthio, cycloalkyl, $-N(R^6)_2$, $-C(O)OR^6$, $-C(O)N(R^6)_2$ or $-N(R^6)-C(O)-R^6$ where each $R^6$ is as defined in the Summary of the Invention. Unless stated otherwise specifically in the specification, it is understood that for radicals, as defined below, that contain a substituted alkenyl group that the substitution can occur on any carbon of the alkenyl group.

"Alkynyl" refers to a straight or branched monovalent hydrocarbon chain radical consisting solely of carbon and hydrogen atoms, containing at least one triple bond, having from two to eight carbon atoms, and which is attached to the rest of the molecule by a single bond, e.g., ethynyl, prop-1-ynyl, but-1-ynyl, pent-1-ynyl, pent-3-ynyl, and the like. Unless stated otherwise specifically in the specification, the alkynyl radical may be optionally substituted by hydroxy, alkoxy, haloalkoxy, cyano, nitro, mercapto, alkylthio, cycloalkyl, $-N(R^6)_2$, $-C(O)OR^6$, $-C(O)N(R^6)_2$ or $-N(R^6)-C(O)-R^6$ where each $R^6$ is as defined in the Summary of the Invention. Unless stated otherwise specifically in the specification, it is understood that for radicals, as defined below, that contain a substituted alkynyl group that the substitution can occur on any carbon of the alkynyl group.

"Aryl" refers to a phenyl or naphthyl radical. Unless stated otherwise specifically in the specification, the term "aryl" or the prefix "ar-" (such as in "aralkyl") is meant to include aryl radicals optionally substituted by one or more substituents selected from the group consisting of alkyl, halo, nitro, cyano, haloalkyl, haloalkoxy, mercapto, alkylthio, phenyl, cycloalkyl, $-OR^6$ (including hydroxy and alkoxy), $-N(R^6)_2$, $-R^7-N(R^6)_2$, $-N(R^6)-C(O)OR^8$, $-R^7-N(R^6)-C(O)OR^8$, $-N(R^6)C(O)-R^6$, $-R^7-N(R^6)-C(O)-R^6$, $-C(O)OR^6$, $-R^7-C(O)OR^6$, $-C(O)-N(R^6)_2$, $-R^7-C(O)-N(R^6)_2$, $-C(O)-R^7-N(R^6)_2$, $-N(R^5)-C(NR^5)-N(R^5)_2$, $-N(R^5)-C(O)-N(R^6)_2$ and $-N(R^5)-C(O)-R^7-N(R^6_2)$ where each $R^5$, $R^6$, and $R^7$ are as defined above in the Summary of the Invention.

"Aralkyl" refers to a radical of the formula $-R_aR_b$ where $R_a$ is an alkyl radical as defined above and $R_b$ is one or more aryl radicals as defined above, e.g., benzyl, diphenylmethyl and the like. The aryl radical(s) may be optionally substituted as described above.

"Aralkoxy" refers to a radical of the formula $-OR_d$ where $R_d$ is an aralkyl radical as defined above, e.g., benzyloxy, and the like. The aryl radical may be optionally substituted as described above.

"Aralkenyl" refers to a radical of the formula $-R_cR_b$ where $R_c$ is an alkenyl radical as defined above and $R_b$ is one or more aryl radicals as defined above, e.g., 3-phenylprop-1-enyl, and the like. The aryl radical(s) and the alkenyl radical may be optionally substituted as described above.

"Alkylene chain" refers to a straight or branched divalent hydrocarbon chain consisting solely of carbon and hydrogen, containing no unsaturation and having from one to eight carbon atoms, e.g., methylene, ethylene, propylene, n-butylene, and the like. The alkylene chain may be optionally substituted by one or more substituents selected from the group consisting of aryl, halo, hydroxy, alkoxy, haloalkoxy, cyano, nitro, mercapto, alkylthio, cycloalkyl, $-N(R^6)_2$, $-C(O)OR^6$, $-C(O)N(R^6)_2$ or $-N(R^6)-C(O)-R^6$ where each $R^6$ is as described above in the Summary of the Invention. The alkylene chain may be attached to the rest of the molecule through any two carbons within the chain.

"Alkenylene chain" refers to a straight or branched divalent hydrocarbon chain consisting solely of carbon and hydrogen, containing at least one double bond and having from two to eight carbon atoms, e.g., ethenylene, prop-1-enylene, but-1-enylene, pent-1-enylene, hexa-1,4-dienylene, and the like. The alkenylene chain may be optionally substituted by one or more substituents selected from the group consisting of aryl, halo, hydroxy, alkoxy, haloalkoxy, cyano, nitro, mercapto, alkylthio, cycloalkyl, $-N(R^6)_2$, $-C(O)OR^6$, $-C(O)N(R^6)_2$ or $-N(R^6)-C(O)-R^6$ where each $R^6$ is as described above in the Summary of the Invention. The alkenylene chain may be attached to the rest of the molecule through any two carbons within the chain.

"Cycloalkyl" refers to a stable monovalent monocyclic or bicyclic hydrocarbon radical consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents independently selected from the group consisting of alkyl, aryl, aralkyl, halo, haloalkyl, hydroxy, alkoxy, haloalkoxy, cyano, nitro, mercapto, alkylthio, cycloalkyl, —N(R$^6$)$_2$, —C(O)OR$^6$, —C(O)N(R$^6$)$_2$ or —N(R$^6$)—C(O)—R$^6$ where each R$^6$ is as defined in the Summary of the Invention.

"Cycloalkylene" refers to a stable divalent monocyclic or bicyclic hydrocarbon consisting solely of carbon and hydrogen atoms, having from three to ten carbon atoms, and which is saturated and attached to the rest of the molecule by two single bonds, e.g., cyclopropylene, cyclobutylene, cyclopentylene, cyclohexylene, decalinylene and the like. Unless otherwise stated specifically in the specification, the term "cycloalkylene" is meant to include cycloalkylene moieties which are optionally substituted by one or more substituents independently selected from the group consisting of alkyl, aryl, aralkyl, halo, haloalkyl, hydroxy, alkoxy, haloalkoxy, cyano, nitro, mercapto, alkylthio, cycloalkyl, —N(R$^6$)$_2$, —C(O)OR$^6$, —C(O)N(R$^6$)$_2$ or —N(R$^6$)—C(O)—R$^6$ where each R$^6$ is as defined in the Summary of the Invention.

"N-heterocyclyl" refers to a stable 3- to 15-membered ring radical which consists of carbon atoms and from one to five heteroatoms selected from the group consisting of nitrogen, oxygen and sulfur wherein at least one of the heteroatoms is a nitrogen. For purposes of this invention, the N-heterocyclyl radical may be a monocyclic, bicyclic or tricyclic ring system, which may include fused or bridged ring systems; and the nitrogen, carbon or sulfur atoms in the N-heterocyclyl radical may be optionally oxidized; the nitrogen atom may be optionally quaternized; and the N-heterocyclyl radical may be partially or fully saturated or aromatic. The N-heterocyclyl radical may be attached to the main structure at any heteroatom or carbon atom which results in the creation of a stable compound. Examples of such N-heterocyclyl radicals include, but are not limited to, azepinyl, azetidinyl, benzimidazolyl, benzoxazolyl, carbazolyl, decahydroisoquinolyl, quinuclidinyl, imidazolyl, imidazolinyl, imidazolidinyl, isothiazolidinyl, indolyl, isoindolyl, indolinyl, isoindolinyl, indolizinyl, isoxazolyl, isoxazolidinyl, morpholinyl, benzothiadiazolyl, oxadiazolyl, octahydroindolyl, octahydroisoindolyl, 2-oxopiperazinyl, 2-oxopiperidinyl, 2-oxopyrrolidinyl, 2-oxoazepinyl, oxazolyl, oxazolidinyl, perhydroazepinyl, piperidinyl, piperazinyl, 4-piperidonyl, phenazinyl, phenothiazinyl, phenoxazinyl, phthalazinyl, pteridinyl, purinyl, pyrrolyl, pyrrolidinyl, pyrazolyl, pyrazolidinyl, pyridinyl, pyrazinyl, pyrimidinyl, pyridazinyl, quinazolinyl, quinoxalinyl, quinolinyl, quinuclidinyl, isoquinolinyl, thiazolyl, thiazolidinyl, thiadiazolyl, triazolyl, tetrazolyl, tetrahydroisoquinolyl, thiomorpholinyl, thiomorpholinyl sulfoxide, and thiomorpholinyl sulfone. The carbon atoms in the N-heterocyclyl radical may be optionally substituted by alkyl, halo, nitro, cyano, haloalkyl, haloalkoxy, mercapto, alkylthio, phenyl, cycloalkyl, —OR$^6$, —N(R$^6$)$_2$, —R$^7$—N(R$^6$)$_2$, —N(R$^6$)—C(O)OR$^8$, —R$^7$—N(R$^6$)—C(O)OR$^8$, —N(R$^6$)—C(O)—R$^6$, —R$^7$—N(R$^6$)—C(O)—R$^6$, —C(O)OR$^6$, —R$^7$—C(O)OR$^6$, —C(O)—N(R$^6$)$_2$, —R$^7$—C(O)—N(R$^6$)$_2$, —C(O)—R$^7$—N(R$^6$)$_2$, —N(R$^5$)—C(NR$^5$)—N(R$^5$)$_2$, —N(R$^5$)—C(O)—N(R$^6$)$_2$ and —N(R$^5$)—C(O)—R$^7$—N(R$^6$$_2$) where each R$^5$, R$^6$, R$^7$ and R$^8$ are as defined above in the Summary of the Invention. The nitrogen atoms in the N-heterocyclyl may be optionally substituted by —C(NR$^5$)—N(R$^5$)$_2$, —C(NR$^5$)—R$^6$, —C(O)—N(R$^6$)$_2$ or —C(O)—R$^7$—N(R$^6$)$_2$ where each R$^5$, R$^6$ and R$^7$ are as defined above in the Summary of the Invention. Preferred N-heterocyclyl radicals are piperidinyl, tetrahydroisoquinolinyl, or benzothiadiazolyl.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkoxy" refers to a radical of the formula —OR$_c$, where R$_c$ is an haloalkyl radical as defined above, e.g., trifluoromethoxy, difluoromethoxy, trichloromethoxy, 2,2,2-trifluoroethoxy, 1-fluoromethyl-2-fluoroethoxy, 3-bromo-2-fluoropropoxy, 1-bromomethyl-2-bromoethoxy, and the like.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), and Wako Chemicals USA, Inc. (Richmond Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandler et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., www.acs.org may be contacted for more details). Chemicals that are known but not commercially available in catalogs may be prepared by custom chemical synthesis houses, where many of the standard chemical supply houses (e.g., those listed above) provide custom synthesis services.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., *Design of Prodrugs* (1985), pp. 7-9, 21-24 (Elsevier, Amsterdam).

A discussion of prodrugs is provided in Higuchi, T., et al., "Pro-drugs as Novel Delivery Systems," *A.C.S. Symposium Series*, Vol. 14, and in *Bioreversible Carriers in Drug Design*, ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

"Mammal" includes humans and domesticated animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Therapeutically effective amount" refers to that amount of a compound of the invention which, when administered to a human in need thereof, is sufficient to effect treatment, as defined below, for a disease-state characterized by thrombotic activity. The amount of a compound of the invention which constitutes a "therapeutically effective amount" will vary depending on the compound, the condition and its severity, and the age of the human to be treated, but can be determined routinely by one of ordinary skill in the art having regard to his own knowledge and to this disclosure.

"Treating" or "treatment" as used herein covers the treatment of a disease-state in a mammal, preferably a human, which disease-state is characterized by thrombotic activity, and includes:

(i) preventing the condition from occurring in a human, in particular, when such human is predisposed to the condition but has not yet been diagnosed as having it;

(ii) inhibiting the condition, i.e., arresting its development; or (iii) relieving the condition, i.e., causing regression of the condition.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

The nomenclature used herein is a modified form of the I.U.P.A.C. nomenclature system wherein the compounds of the invention are named herein as derivatives of the acid moiety. For example, the following compound of formula (III) wherein $R^1$ is hydrogen, $R^2$ is —P(O)(OH)—$R^7$—N(H)—C(O)O$R^8$ (where $R^7$ is hexyl and $R^8$ is benzyl), $R^3$ is —C(O)OH, and $R^4$ is 3-guanidinophenyl, i.e., the compound of the following formula:

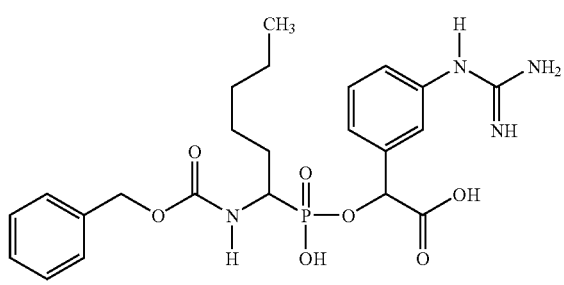

is named herein as 2-(3-guanidinophenyl)-2-((1-(benzyloxycarbonyl)aminohexyl)-(hydroxy)phosphinoyl)oxyethanoic acid. Unless otherwise indicated, compound names are intended to include any single stereoisomer, enantiomer, diastereomer, racemate or mixture of stereoisomers.

The use of parentheses in a formula herein is used to conserve space. Accordingly, the use of parenthesis in a formula indicates that the group enclosed within the parentheses is attached directly to the atom preceding the parenthesis. For example, the term —P(O)(OR$^5$)—R$^7$—N(R$^5$)—C(O)—R$^7$—N(R$^5$)—C(O)OR$^8$ can be drawn as follows:

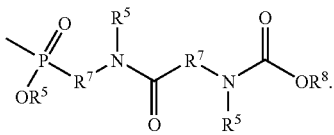

B. Utility of the Compounds of the Invention

The compounds of the invention are inhibitors of plasma carboxypeptidase B and are therefore useful in treating disease-states or conditions characterized by thrombotic activity, i.e., by the formation of a thrombus, or by hypercoagulability. It is known that hypercoagulability may lead to thrombo-embolic disease-states. Conditions associated with hypercoagulability include protein C resistance and inherited or acquired deficiencies in antithrombin III, protein C, protein S and heparin cofactor II. Other conditions and disease-states known to be associated with thrombotic activity and/or hypercoagulability include circulatory and septic shock, circulating antiphospholipid antibodies, homocysteinuria, homocysteinemia, heparin induced thrombocytopenia and defects in fibrinolysis. The compounds of the invention are thus indicated both in the therapeutic and/or prophylactic treatment of these conditions and/or disease-states. The compounds of the invention are further indicated in the treatment of conditions where there is an undesirable excess of plasma carboxypeptidase B/activated plasma carboxypeptidase B.

In addition to the foregoing, the compounds of the invention are useful in treating disease-states such as venous thrombosis and pulmonary embolism, arterial thrombosis (e.g., in myocardial infarction, unstable angina, thrombosis-based stroke and peripheral arterial thrombosis) and systemic embolism usually from the atrium during arterial fibrillation or from the left ventricle after transmural myocardial infarction.

Furthermore, the compounds of the invention have utility in treating re-occlusion and restenosis after thrombolysis, percutaneous trans-luminal angioplasty (PTA), endoarterectomy, and coronary bypass operations, and in the prevention of thrombotic activity after microsurgery and vascular surgery in general.

Further indications include the therapeutic and/or prophylactic treatment of disseminated intravascular coagulation caused by bacteria, multiple trauma, intoxication or any other mechanism, fibrinolytic treatment when blood is in contact with foreign surfaces in the body, such as vascular grafts, vascular stents, vascular catheters, mechanical and biological prosthetic valves or any other medical device used in vascular surgery, and fibrinolytic treatment when blood is in contact with medical devices outside the body, such as during cardiovascular surgery using a heart-lung machine or hemodialysis.

The compounds of the invention may also be combined and/or coadministered with any anti-thrombotic or anti-coagulant agent with a different mechanism of action, such as the anti-platelet agents acetylsalicylic acid, ticlopidine, clopidogrel, thromboxane receptor and/or synthetase inhibitors, factor Xa and factor VIIa inhibitors, fibrinogen receptor antagonists, prostacyclin mimetics, phosphodiesterase inhibitors, ADP receptor antagonists, and thrombin inhibitors.

The compounds of the invention may be further combined and/or co-administered with thrombolytics such as tissue plasminogen activator (natural, recombinant or modified), streptokinase, urokinase, pro-urokinase, anisolyated plasminogen-streptokinase activator complex, animal salivary gland plasminogen activators, and the like, in the treatment of thrombotic disease-states, in particular, myocardial infarction and stroke.

C. Testing of the Compounds of the Invention

The inhibitory effects of the compounds of the invention against activated plasma carboxypeptidase B may be determined either in a defined system using the purified protein or in plasma milieu. Briefly, plasma carboxypeptidase B is first activated with a thrombin/thrombomodulin complex in the presence of calcium. Plasma carboxypeptidase B activity is then assayed by measuring the hydrolysis of substrate such as hippuryl-arginine (Folk et al., *J. Biol. Chem.* (1960), Vol. 235, pp. 2272-2277) or furylacryloyl-alanyl-arginine (Plummer and Kimmel, *Anal. Biochem.* (1980), Vol. 108, pp 348-353). The product from hippuryl-arginine may be converted to a chromogen to improve the sensitivity of the assay (Hendricks, D. et al., *Clinica Chimica Acta* (1986), Vol. 157, pp. 103-108., Wang, W. et al., *Journal of Biological Chemistry* (1994), Vol. 269, pp. 15937-15944, or in Zhao et al., "Identification and characterization of two thrombin-activatable fibrinolysis inhibitor isoforms", *Thromb. Haemost.* (1998), Vol. 80, pp. 949-955.

The effects of the compounds of the invention on clot lysis time were investigated using a general plate clot lysis assay (for instance, Beebe and Aronson, in *Thrombosis Research* (1987), Vol. 47, pp. 123-128; Jones and Meunier, in *Thrombosis and Haemostasis* (1990), Vol. 64, pp. 455-463; and Bajzar et al., *J. Biol. Chem.* (1996), Vol. 271, pp. 16603-16608) and/or in an in vitro plasma clot lysis assay described in Nagashima, M. et al., in *Thrombosis Research* (2000), Vol. 98, pp. 333-342.

D. Administration of the Compounds of the Invention

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the present invention may be in any form that allows for the composition to be administered to a patient. Typical routes of administration include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see Remington's Pharmaceutical Sciences, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state characterized by thrombotic activity, i.e., by the formation of a thrombus, or by hypercoagulability, in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, e.g., inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, e.g., a gelatin capsule, it may contain, in addition to materials of the above type, a liquid carrier such as polyethylene glycol or a fatty oil.

The pharmaceutical composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 1% by weight of the compound of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, e.g., of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units which can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

Whether in solid, liquid or gaseous form, the pharmaceutical composition of the present invention may contain one or more known pharmacological agents used in the treatment of disease-states characterized by thrombotic activity.

The pharmaceutical compositions of the invention may be prepared by methodology well known in the pharmaceutical art. For example, a pharmaceutical composition intended to be administered by injection can be prepared by combining a compound of the invention with water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disease-state; and the host undergoing therapy. Generally, a therapeutically effective daily dose is from about 0.14 mg to about 14.3 mg/kg of body weight per day of a compound of the invention, or a pharmaceutically acceptable salt thereof; preferably, from about 0.7 mg to about 10 mg/kg of body weight per day; and most preferably, from about 1.4 mg to about 7.2 mg/kg of body weight per day. For example, for administration to a 70 kg person, the dosage range would be from about 10 mg to about 1.0 gram per day of a compound of the invention, or a pharmaceutically acceptable salt thereof, preferably from about 50 mg to about 700 mg per day, and most preferably from about 100 mg to about 500 mg per day.

E. Preferred Embodiments

Of the compounds of the invention as set forth above in the Summary of the Invention, several groups of compounds are particularly preferred.

Of the compounds of formula (I) as set forth above in the Summary of the Invention, a preferred group is that group of compounds of formula (I) wherein:
$R^1$ is hydrogen;
$R^2$ is —SH or —S—C(O)—$R^8$;
$R^3$ is tetrazole, —C(O)O$R^6$ or —C(O)O—$R^7$—OC(O)$R^5$;
$R^4$ is aryl optionally substituted by one or more substituents selected from the group consisting of alkyl, halo, nitro, cyano, —N($R^6$)$_2$, —$R^7$—N($R^6$)$_2$, —N($R^6$)—C(O)O$R^8$, —$R^7$—N($R^6$)—C(O)O$R^8$, —N($R^6$)—C(O)—$R^6$, —$R^7$—N($R^6$)—C(O)—$R^6$, —C(O)—N($R^6$)$_2$, —C(O)—$R^7$—N($R^6$)$_2$, —N($R^5$)—C(N$R^5$)—N($R^5$)$_2$, —N($R^5$)—C(O)—N($R^6$)$_2$ and —N($R^5$)—C(O)—$R^7$—N($R^6$_2$);
or $R^4$ is N-heterocyclyl wherein a carbon atom in the N-heterocyclyl may be optionally substituted by alkyl, halo, nitro, cyano, —N($R^6$)$_2$, —$R^7$—N($R^6$)$_2$, —N($R^6$)—C(O)O$R^8$, —$R^7$—N($R^6$)—C(O)O$R^8$, —N($R^6$)—C(O)—$R^6$, —$R^7$—N($R^6$)—C(O)—$R^6$, —C(O)—N($R^6$)$_2$, —C(O)—$R^7$—N($R^6$)$_2$, —N($R^5$)—C(N$R^5$)—N($R^5$)$_2$, —N($R^5$)—C(O)—N($R^6$)$_2$ or —N($R^5$)—C(O)—$R^7$—N($R^6$_2$), or wherein a nitrogen atom in the N-heterocyclyl may be optionally substituted by —C(N$R^5$)—N($R^5$)$_2$, —C(N$R^5$)—$R^6$, —C(O)—N($R^6$)$_2$ or —C(O)—$R^7$—N($R^6$)$_2$;
each $R^5$ is independently hydrogen, alkyl or aralkyl;
each $R^6$ is independently hydrogen, alkyl, alkenyl, alkynyl, aryl, aralkyl or aralkenyl;
each $R^7$ is independently a straight or branched alkylene chain optionally substituted by hydroxy, mercapto, alkylthio, aryl, cycloalkyl, —N($R^6$)$_2$, —C(O)O$R^6$, or —C(O)N($R^6$)$_2$; and
each $R^8$ is independently alkyl, alkenyl, aryl, aralkyl or aralkenyl.

Of this preferred group of compounds, a preferred subgroup is that subgroup of compounds of formula (I) wherein:
$R^1$ is hydrogen;
$R^2$ is —SH or —S—C(O)—$R^8$;
$R^3$ is —C(O)O$R^6$;
$R^4$ is aryl optionally substituted by one or more substituents selected from the group consisting of halo, nitro, —N($R^6$)$_2$, —$R^7$—N($R^6$)$_2$ and —N($R^5$)—C(N$R^5$)—N($R^5$)$_2$;
each $R^5$ is independently hydrogen, alkyl or aralkyl;
each $R^6$ is independently hydrogen, alkyl, aryl or aralkyl;
$R^7$ is a straight or branched alkylene chain; and
$R^8$ is independently alkyl, alkenyl, aryl, aralkyl or aralkenyl.

Of this preferred subgroup of compounds of formula (I), preferred compounds are selected from the group consisting of the following:
2-(4-guanidinophenyl)-3-mercaptopropanoic acid;
2-(3-guanidinophenyl)-3-mercaptopropanoic acid;
2-(3-aminophenyl)-3-mercaptopropanoic acid; and
2-(2-chloro-5-guanidinophenyl)-3-mercaptopropanoic acid.

Of the preferred group of compounds of formula (I) as set forth above, another preferred subgroup is that subgroup of compounds of formula (I) wherein:
$R^1$ is hydrogen;
$R^2$ is —SH, or —S—C(O)—$R^8$;
$R^3$ is —C(O)O$R^6$;
$R^4$ is 3(4)-piperidinyl wherein the nitrogen atom in the piperidinyl radical is optionally substituted by —C(N$R^5$)—N($R^5$)$_2$, —C(N$R^5$)—$R^6$, —C(O)—N($R^6$)$_2$ or —C(O)—$R^7$—N($R^6$)$_2$;
each $R^5$ is independently hydrogen, alkyl or aralkyl;
each $R^6$ is independently hydrogen, alkyl, aryl or aralkyl;
$R^7$ is a straight or branched alkylene chain optionally substituted by hydroxy, mercapto, alkylthio, aryl, cycloalkyl, —N($R^6$)$_2$, —C(O)O$R^6$, or —C(O)N($R^6$)$_2$; and
$R^8$ is alkyl, alkenyl, aryl, aralkyl or aralkenyl.

Of this preferred subgroup of compounds of formula (I), preferred compounds are selected from the group consisting of the following:
2-(piperidin-4-yl)-3-mercaptopropanoic acid;
2-(1-amidinopiperidin-4-yl)-3-mercaptopropanoic acid;
2-(1-(1-iminoethyl)piperidin-4-yl)-3-mercaptopropanoic acid;
2-(1-(aminomethylcarbonyl)piperidin-4-yl)-3-mercaptopropanoic acid;
2-(piperidin-3-yl)-3-mercaptopropanoic acid; and
2-(1-amidinopiperidin-3-yl)-3-mercaptopropanoic acid.

Of the compounds of formula (I) as set forth above in the Summary of the Invention, another preferred group is that group of compounds of formula (I) wherein:
$R^1$ is hydrogen;
$R^2$ is —P(O)(O$R^5$)$_2$, —P(O)(O$R^5$)$R^6$ or —P(O)(O$R^5$)—$R^7$—C(O)—$R^8$;
$R^3$ is tetrazole, —C(O)O$R^6$, or —C(O)O—$R^7$—OC(O)$R^5$;
$R^4$ is aryl optionally substituted by one or more substituents selected from the group consisting of alkyl, halo, nitro, cyano, —N($R^6$)$_2$, —$R^7$—N($R^6$)$_2$, —N($R^6$)—C(O)O$R^8$, —$R^7$—N($R^6$)—C(O)O$R^8$, —N($R^6$)—C(O)—$R^6$, —$R^7$—N($R^6$)—C(O)—$R^6$, —C(O)—N($R^6$)$_2$, —C(O)—$R^7$—N (R$^6$)$_2$, —N(R$^5$)—C(NR$^5$)—N(R$^5$)$_2$, —N(R$^5$)—C(O)—N(R$^6$)$_2$ and —N(R$^5$)—C(O)—R$^7$—N(R$^6$$_2$);

or R$^4$ is N-heterocyclyl wherein a carbon atom in the N-heterocyclyl may be optionally substituted by alkyl, halo, nitro, cyano, —N(R$^6$)$_2$, —R$^7$—N(R$^6$)$_2$, —N(R$^6$)—C(O)OR$^8$, —R$^7$—N(R$^6$)—C(O)OR$^8$, —N(R$^6$)—C(O)—R$^6$, —R$^7$—N(R$^6$)—C(O)—R$^6$, —C(O)—N(R$^6$)$_2$, —C(O)—R$^7$—N(R$^6$)$_2$, —N(R$^5$)—C(NR$^5$)—N(R$^5$)$_2$, —N(R$^5$)—C(O)—N(R$^6$)$_2$ or —N(R$^5$)—C(O)—R$^7$—N(R$^6$$_2$), or wherein a nitrogen atom in the N-heterocyclyl may be optionally substituted by —C(NR$^5$)—N(R$^5$)$_2$, —C(NR$^5$)—R$^6$, —C(O)—N(R$^6$)$_2$ or —C(O)—R$^7$—N(R$^6$)$_2$;

each R$^5$ is independently hydrogen, alkyl or aralkyl;
each R$^6$ is independently hydrogen, alkyl, alkenyl, alkynyl, aryl, aralkyl or aralkenyl;
each R$^7$ is independently a straight or branched alkylene chain optionally substituted by hydroxy, mercapto, alkylthio, aryl, cycloalkyl, —N(R$^6$)$_2$, —C(O)OR$^6$, or —C(O)N(R$^6$)$_2$; and
each R$^8$ is independently alkyl, alkenyl, aryl, aralkyl or aralkenyl.

Of this preferred group of compounds, a preferred subgroup is that subgroup of compounds of formula (I) wherein:
R$^1$ is hydrogen;
R$^2$ is —P(O)(OR$^5$)$_2$, —P(O)(OR$^5$)R$^6$ or —P(O)(OR$^5$)—R$^7$—C(O)—R$^8$;
R$^3$ is —C(O)OR$^6$;
R$^4$ is aryl optionally substituted by one or more substituents selected from the group consisting of halo, nitro, —N(R$^6$)$_2$, —R$^7$—N(R$^6$)$_2$ and —N(R$^5$)—C(NR$^5$)—N(R$^5$)$_2$;
each R$^5$ is independently hydrogen, alkyl or aralkyl;
each R$^6$ is independently hydrogen, alkyl, aryl or aralkyl;
each R$^7$ is independently a straight or branched alkylene chain optionally substituted by aryl, —N(R$^6$)$_2$ or —C(O)OR$^6$; and
R$^8$ is alkyl, alkenyl, aryl, aralkyl or aralkenyl.

Of this preferred subgroup of compounds of formula (I), preferred compounds are selected from the group consisting of the following:
2-(3-guanidinophenyl)-3-phosphonopropanoic acid;
2-(3-aminophenyl)-3-((phenyl)(hydroxy)phosphinoyl)propanoic acid;
2-(3-aminophenyl)-3-((4-phenylbutyl)(hydroxy)phosphinoyl)propanoic acid;
2-(3-aminophenyl)-3-((pentyl)(hydroxy)phosphinoyl)propanoic acid;
2-(3-guanidinophenyl)-3-((phenyl)(hydroxy)phosphinoyl)propanoic acid;
2-(3-guanidinophenyl)-3-((4-phenylbutyl)(hydroxy)phosphinoyl)propanoic acid;
2-(3-guanidinophenyl)-3-((pentyl)(hydroxy)phosphinoyl)propanoic acid;
2-(3-guanidinophenyl)-3-((4-methylpentyl)(hydroxy)phosphinoyl)propanoic acid;
2-(3-guanidinophenyl)-3-((3-phenylpropyl)(hydroxy)phosphinoyl)propanoic acid;
2-(3-guanidinophenyl)-3-((3-phenylprop-2-enyl)(hydroxy)phosphinoyl)propanoic acid;
2-(3-guanidinophenyl)-3-((phenylmethyl)(hydroxy)phosphinoyl)propanoic acid;
2-(3-guanidinophenyl)-3-((pentyl)(hydroxy)phosphinoyl)propanoic acid methyl ester;
2-(3-guanidinophenyl)-3-((ethyl)(hydroxy)phosphinoyl)propanoic acid;
2-(3-guanidinophenyl)-3-((2-phenylethyl)(hydroxy)phosphinoyl)propanoic acid; and
2-(3-guanidinophenyl)-3-((2-(methylcarbonyl)ethyl)(hydroxy)phosphinoyl)propanoic acid.

Of the compounds of formula (I) as set forth above in the Summary of the Invention, another preferred group is that group of compounds of formula (I) wherein:
R$^1$ is hydrogen;
R$^2$ is —P(O)(OR$^5$)—R$^7$—N(R$^5$)—C(O)OR$^8$;
R$^3$ is —C(O)OR$^6$ (where R$^6$ is alkyl, aryl or aralkyl);
R$^4$ is aryl optionally substituted by one or more substituents selected from the group consisting of alkyl, halo, nitro, cyano, —N(R$^6$)$_2$, —R$^7$—N(R$^6$)$_2$, —N(R$^6$)—C(O)OR$^8$, —R$^7$—N(R$^6$)—C(O)OR$^8$, —N(R$^6$)—C(O)—R$^6$, —R$^7$—N(R$^6$)—C(O)—R$^6$, —C(O)—N(R$^6$)$_2$, —C(O)—R$^7$—N(R$^6$)$_2$, —N(R$^5$)—C(NR$^5$)—N(R$^5$)$_2$, —N(R$^5$)—C(O)—N(R$^6$)$_2$ and —N(R$^5$)—C(O)—R$^7$—N(R$^6$$_2$) where each R$^6$ is independently hydrogen, alkyl, aryl or aralkyl;
each R$^5$ is independently hydrogen, alkyl or aralkyl;
each R$^7$ is a straight or branched alkylene chain optionally substituted by aryl, —N(R$^6$)$_2$ or —C(O)OR$^6$; and
each R$^8$ is independently alkyl, alkenyl, aryl, aralkyl or aralkenyl.

Of this group of compounds of formula (I), preferred compounds are selected from the group consisting of the following:
2-(3-(t-butoxycarbonylamino)methylphenyl)-3-((1-(benzyloxycarbonyl)amino-2-methylpropyl)(hydroxy)phosphinoyl)propanoic acid t-butyl ester; and
2-(3-(t-butoxycarbonylamino)methylphenyl)-3-((1-(benzyloxycarbonyl)amino-2-methylpropyl)(ethoxy)phosphinoyl)propanoic acid t-butyl ester.

Of the compounds of formula (I) as set forth above in the Summary of the Invention, another preferred group is that group of compounds of formula (I) wherein:
R$^1$ is hydrogen;
R$^2$ is —P(O)(OR$^5$)—R$^7$—N(R$^6$)$_2$ or —P(O)(OR$^5$)—R$^7$—N(R$^5$)—C(S)—N(R$^6$)$_2$;
R$^3$ is tetrazole, —C(O)OR$^6$, or —C(O)O—R$^7$—OC(O)R$^5$;
R$^4$ is aryl optionally substituted by one or more substituents selected from the group consisting of alkyl, halo, nitro, cyano, —N(R$^6$)$_2$, —R$^7$—N(R$^6$)$_2$, —N(R$^6$)—C(O)OR$^8$, —R$^7$—N(R$^6$)—C(O)OR$^8$, —N(R$^6$)—C(O)—R$^6$, —R$^7$—N(R$^6$)—C(O)—R$^6$, —C(O)—N(R$^6$)$_2$, —C(O)—R$^7$—N(R$^6$)$_2$, —N(R$^5$)—C(NR$^5$)—N(R$^5$)$_2$, —N(R$^5$)—C(O)—N(R$^6$)$_2$ and —N(R$^5$)—C(O)—R$^7$—N(R$^6$$_2$);
each R$^5$ is independently hydrogen, alkyl or aralkyl;
each R$^6$ is independently hydrogen, alkyl, alkenyl, alkynyl, aryl, aralkyl or aralkenyl;
each R$^7$ is a straight or branched alkylene chain optionally substituted by hydroxy, mercapto, alkylthio, aryl, cycloalkyl, —N(R$^6$)$_2$, —C(O)OR$^6$, or —C(O)N(R$^6$)$_2$; and
each R$^8$ is independently alkyl, alkenyl, aryl, aralkyl or aralkenyl.

Of this group of compounds of formula (I), preferred compounds are selected from the group consisting of the following:
2-(3-(t-butoxycarbonylamino)methylphenyl)-3-((1-amino-2-methylpropyl)(hydroxy)-phosphinoyl)propanoic acid t-butyl ester; and
2-(3-(t-butoxycarbonylamino)methylphenyl)-3-((1-amino-2-methylpropyl)(ethoxy)-phosphinoyl)propanoic acid t-butyl ester.

Of the compounds of formula (I) as set forth above in the Summary of the Invention, another preferred group is that group of compounds of formula (I) wherein:
R$^1$ is hydrogen;
R$^2$ is —P(O)(OR$^5$)—R$^7$—N(R$^5$)—S(O)$_2$—R$^9$;
R$^3$ is tetrazole, —C(O)OR$^6$, or —C(O)O—R$^7$—OC(O)R$^5$;

R$^4$ is aryl optionally substituted by one or more substituents selected from the group consisting of alkyl, halo, nitro, cyano, —N(R$^6$)$_2$, —R$^7$—N(R$^6$)$_2$, —N(R$^6$)—C(O)OR$^8$, —R$^7$—N(R$^6$)—C(O)OR$^8$, —N(R$^6$)—C(O)—R$^6$, —R$^7$—N(R$^6$)—C(O)—R$^6$, —C(O)—N(R$^6$)$_2$, —C(O)—R$^7$—N(R$^6$)$_2$, —N(R$^5$)—C(NR$^5$)—N(R$^5$)$_2$, —N(R$^5$)—C(O)—N(R$^6$)$_2$ and —N(R$^5$)—C(O)—R$^7$—N(R$^6$$_2$);

or R$^4$ is N-heterocyclyl wherein a carbon atom in the N-heterocyclyl may be optionally substituted by alkyl, halo, nitro, cyano, —N(R$^6$)$_2$, —R$^7$—N(R$^6$)$_2$, —N(R$^6$)—C(O)OR$^8$, —R$^7$—N(R$^6$)—C(O)OR$^8$, —N(R$^6$)—C(O)—R$^6$, —R$^7$—N(R$^6$)—C(O)—R$^6$, —C(O)—N(R$^6$)$_2$, —C(O)—R$^7$—N(R$^6$)$_2$, —N(R$^5$)—C(NR$^5$)—N(R$^5$)$_2$, —N(R$^5$)—C(O)—N(R$^6$)$_2$ or —N(R$^5$)—C(O)—R$^7$—N(R$^6$$_2$), or wherein a nitrogen atom in the N-heterocyclyl may be optionally substituted by —C(NR$^5$)—N(R$^5$)$_2$, —C(NR$^5$)—R$^6$, —C(O)—N(R$^6$)$_2$ or —C(O)—R$^7$—N(R$^6$)$_2$;

each R$^5$ is independently hydrogen, alkyl or aralkyl;

each R$^6$ is independently hydrogen, alkyl, alkenyl, alkynyl, aryl, aralkyl or aralkenyl;

each R$^7$ is independently cycloalkylene (optionally substituted by alkyl), a straight or branched alkylene chain (optionally substituted by hydroxy, mercapto, alkylthio, aryl, cycloalkyl, —N(R$^6$)$_2$, —C(O)OR$^6$, or —C(O)N(R$^6$)$_2$), or a straight or branched alkenylene chain (optionally substituted by hydroxy, mercapto, alkylthio, aryl, cycloalkyl, —N(R$^6$)$_2$, —C(O)OR$^6$, or —C(O)N(R$^6$)$_2$);

each R$^8$ is independently alkyl, alkenyl, aryl, aralkyl or aralkenyl; and

R$^9$ is —R$^7$N(R$^6$)C(O)OR$^8$, haloalkyl, alkyl (optionally substituted by hydroxy, alkoxy, aralkoxy, haloalkoxy, cyano, nitro, —N(R$^6$)$_2$, —C(O)OR$^6$, —C(O)N(R$^6$)$_2$ or —N(R$^6$)C(O)R$^6$), alkenyl (optionally substituted by hydroxy, alkoxy, haloalkoxy, cyano, nitro, —N(R$^6$)$_2$, —C(O)OR$^6$, —C(O)N(R$^6$)$_2$ or —N(R$^6$)C(O)R$^6$), aryl (optionally substituted by alkyl, aryl, aralkyl, hydroxy, alkoxy, cyano, nitro, halo, haloalkoxy, —N(R$^6$)$_2$, —C(O)OR$^6$, —C(O)N(R$^6$)$_2$ or —N(R$^6$)C(O)R$^6$), aralkyl (wherein the aryl group is optionally substituted by alkyl, aryl, aralkyl, hydroxy, alkoxy, cyano, nitro, halo, haloalkoxy, —N(R$^6$)$_2$, —C(O)OR$^6$, —C(O)N(R$^6$)$_2$ or —N(R$^6$)C(O)R$^6$), aralkenyl (wherein the aryl group is optionally substituted by alkyl, aryl, aralkyl, hydroxy, alkoxy, cyano, nitro, halo, haloalkoxy, —N(R$^6$)$_2$, —C(O)OR$^6$, —C(O)N(R$^6$)$_2$ or —N(R$^6$)C(O)R$^6$), or N-heterocyclyl (optionally substituted by alkyl, aryl, aralkyl, hydroxy, alkoxy, cyano, nitro, halo, haloalkoxy, —N(R$^6$)$_2$, —C(O)OR$^6$, —C(O)N(R$^6$)$_2$ or —N(R$^6$)C(O)R$^6$).

Of this group of compounds, a preferred subgroup is that subgroup of compounds of formula (I) wherein:

R$^1$ is hydrogen;

R$^2$ is —P(O)(OR$^5$)—R$^7$—N(R$^5$)—S(O)$_2$—R$^9$;

R$^3$ is tetrazole, —C(O)OR$^6$, or —C(O)O—R$^7$—OC(O)R$^5$;

R$^4$ is aryl optionally substituted by one or more substituents selected from the group consisting of alkyl, halo, nitro, cyano, —N(R$^6$)$_2$, —R$^7$—N(R$^6$)$_2$, —N(R$^6$)—C(O)OR$^8$; —R$^7$—N(R$^6$)—C(O)OR$^8$, and —N(R$^5$)—C(NR$^5$)—N(R$^5$)$_2$;

each R$^5$ is independently hydrogen, alkyl or aralkyl;

each R$^6$ is independently hydrogen, alkyl, alkenyl, alkynyl, aryl, aralkyl or aralkenyl;

each R$^7$ is independently a straight or branched alkylene chain (optionally substituted by hydroxy, mercapto, alkylthio, aryl, cycloalkyl, —N(R$^6$)$_2$, —C(O)OR$^6$, or —C(O)N(R$^6$)$_2$), each R$^8$ is independently alkyl, alkenyl, aryl, aralkyl or aralkenyl; and R$^9$ is —R$^7$N(R$^6$)C(O)OR$^8$, haloalkyl, alkyl (optionally substituted by hydroxy, alkoxy, aralkoxy, haloalkoxy, cyano, nitro, —N(R$^6$)$_2$, —C(O)OR$^6$, —C(O)N(R$^6$)$_2$ or —N(R$^6$)C(O)R$^6$), alkenyl (optionally substituted by hydroxy, alkoxy, haloalkoxy, cyano, nitro, —N(R$^6$)$_2$, —C(O)OR$^6$, —C(O)N(R$^6$)$_2$ or —N(R$^6$)C(O)R$^6$), aryl (optionally substituted by alkyl, aryl, aralkyl, hydroxy, alkoxy, cyano, nitro, halo, haloalkoxy, —N(R$^6$)$_2$, —C(O)OR$^6$, —C(O)N(R$^6$)$_2$ or —N(R$^6$)C(O)R$^6$), aralkyl (wherein the aryl group is optionally substituted by alkyl, aryl, aralkyl, hydroxy, alkoxy, cyano, nitro, halo, haloalkoxy, —N(R$^6$)$_2$, —C(O)OR$^6$, —C(O)N(R$^6$)$_2$ or —N(R$^6$)C(O)R$^6$), aralkenyl (wherein the aryl group is optionally substituted by alkyl, aryl, aralkyl, hydroxy, alkoxy, cyano, nitro, halo, haloalkoxy, —N(R$^6$)$_2$, —C(O)OR$^6$, —C(O)N(R$^6$)$_2$ or —N(R$^6$)C(O)R$^6$), or N-heterocyclyl (optionally substituted by alkyl, aryl, aralkyl, hydroxy, alkoxy, cyano, nitro, halo, haloalkoxy, —N(R$^6$)$_2$, —C(O)OR$^6$, —C(O)N(R$^6$)$_2$ or —N(R$^6$)C(O)R$^6$).

Of this preferred subgroup of compounds, a preferred class is that class of compounds of formula (I) wherein:

R$^1$ is hydrogen;

R$^2$ is —P(O)(OR$^5$)—R$^7$—N(R$^5$)—S(O)$_2$—R$^9$;

R$^3$ is tetrazole, —C(O)OR$^6$, or —C(O)O—R$^7$—OC(O)R$^5$;

R$^4$ is aryl optionally substituted by one or more substituents selected from the group consisting of alkyl, halo, nitro, cyano, —N(R$^6$)$_2$, —R$^7$—N(R$^6$)$_2$, —N(R$^6$)—C(O)OR$^8$; —R$^7$—N(R$^6$)—C(O)OR$^8$, and —N(R$^5$)—C(NR$^5$)—N(R$^5$)$_2$;

each R$^5$ is independently hydrogen, alkyl or aralkyl;

each R$^6$ is independently hydrogen, alkyl, alkenyl, alkynyl, aryl, aralkyl or aralkenyl;

each R$^7$ is independently a straight or branched alkylene chain optionally substituted by hydroxy, mercapto, alkylthio, aryl, cycloalkyl, —N(R$^6$)$_2$, —C(O)OR$^6$, or —C(O)N(R$^6$)$_2$, each R$^8$ is independently alkyl, alkenyl, aryl, aralkyl or aralkenyl; and R$^9$ is alkyl (optionally substituted by hydroxy, alkoxy, aralkoxy, haloalkoxy, cyano, nitro, —N(R$^6$)$_2$, —C(O)OR$^6$, —C(O)N(R$^6$)$_2$ or —N(R$^6$)C(O)R$^6$), alkenyl (optionally substituted by hydroxy, alkoxy, haloalkoxy, cyano, nitro, —N(R$^6$)$_2$, —C(O)OR$^6$, —C(O)N(R$^6$)$_2$ or —N(R$^6$)C(O)R$^6$), aralkyl (wherein the aryl group is optionally substituted by alkyl, aryl, aralkyl, hydroxy, alkoxy, cyano, nitro, halo, haloalkoxy, —N(R$^6$)$_2$, —C(O)OR$^6$, —C(O)N(R$^6$)$_2$ or —N(R$^6$)C(O)R$^6$), aralkenyl (wherein the aryl group is optionally substituted by alkyl, aryl, aralkyl, hydroxy, alkoxy, cyano, nitro, halo, haloalkoxy, —N(R$^6$)$_2$, —C(O)OR$^6$, —C(O)N(R$^6$)$_2$ or —N(R$^6$)C(O)R$^6$).

Of this preferred class of compounds of formula (I), preferred compounds are selected from the group consisting of the following:

2-(3-(amino)methylphenyl)-3-((1-(3-phenylpropylsulfonyl)amino-2-methylpropyl)-(hydroxy)phosphinoyl)propanoic acid, methyl ester;

2-(3-(t-butoxycarbonylamino)methylphenyl)-3-((1-(3-phenylpropylsulfonyl)amino-2-methylpropyl)(hydroxy)phosphinoyl)propanoic acid;

2-(3-(t-butoxycarbonylamino)methylphenyl)-3-((1-(3-phenylpropylsulfonyl)amino-2-methylpropyl)(hydroxy)phosphinoyl)propanoic acid, methyl ester;

2-(3-(amino)methylphenyl)-3-((1-(3-phenylpropylsulfonyl)amino-2-methylpropyl)(hydroxy)-phosphinoyl)propanoic acid;

(2R)-2-(3-(amino)methylphenyl)-3-(((1R)-1-(3-phenylpropylsulfonyl)amino-2-methylpropyl)(hydroxy)phosphinoyl)propanoic acid;

(2S)-2-(3-(amino)methylphenyl)-3-(((1R)-1-(3-phenylpropylsulfonyl)amino-2-methylpropyl)(hydroxy)phosphinoyl)propanoic acid;

(2R/S)-2-(3-(amino)methylphenyl)-3-(((1S)-1-(3-phenylpropylsulfonyl)amino-2-methylpropyl)(hydroxy)phosphinoyl)propanoic acid;

(2R/S)-2-(3-(amino)methylphenyl)-3-(((1R)-1-(3-phenylpropylsulfonyl)amino-2-methylpropyl)(hydroxy)phosphinoyl)propanoic acid;

(2R)-2-(3-(amino)methylphenyl)-3-(((1S)-1-(3-phenylpropylsulfonyl)amino-2-methylpropyl)(hydroxy)phosphinoyl)propanoic acid;

(2S)-2-(3-(amino)methylphenyl)-3-(((1S)-1-(3-phenylpropylsulfonyl)amino-2-methylpropyl)(hydroxy)phosphinoyl)propanoic acid;

2-(3-(t-butoxycarbonylamino)methylphenyl)-3-((1-(3-phenylpropylsulfonyl)amino-2-methylpropyl)(ethoxy)phosphinoyl)propanoic acid, t-butyl ester;

2-(3-(amino)methylphenyl)-3-((1-(2-phenylethylsulfonyl)amino-2-methylpropyl)-(hydroxy)phosphinoyl)propanoic acid;

2-(3-(amino)methylphenyl)-3-((1-(benzylsulfonyl)amino-2-methylpropyl)-(hydroxy)phosphinoyl) propanoic acid;

2-(3-(amino)methylphenyl)-3-((1-(2-(naphth-1-yl)ethylsulfonyl)amino-2-methylpropyl)(hydroxy)phosphinoyl)propanoic acid;

2-(3-(amino)methylphenyl)-3-((1-(3-(4-methoxyphenyl)propylsulfonyl)amino-2-methylpropyl)(hydroxy)phosphinoyl)propanoic acid;

2-(3-(amino)methylphenyl)-3-((1-(2-(4-methoxyphenyl)ethylsulfonyl)amino-2-methylpropyl)(hydroxy)phosphinoyl)propanoic acid;

2-(3-(amino)methylphenyl)-3-((1-(methylsulfonyl)amino-2-methylpropyl)(hydroxy)phosphinoyl)propanoic acid;

2-(3-(amino)methylphenyl)-3-((1-(2-benzyloxyethylsulfonyl)amino-2-methylpropyl)-(hydroxy)phosphinoyl)propanoic acid;

2-(3-(amino)methylphenyl)-3-((1-(2-hydroxyethylsulfonyl)amino-2-methylpropyl)-(hydroxy)phosphinoyl)propanoic acid;

2-(3-aminophenyl)-3-((1-(3-phenylpropylsulfonyl)amino-2-methylpropyl)-(hydroxy)phosphinoyl)propanoic acid;

2-(3-guanidinophenyl)-3-((1-(3-phenylpropylsulfonyl)amino-2-methylpropyl)(hydroxy)-phosphinoyl)propanoic acid;

2-(3-(amino)methylphenyl)-3-((1-(4-phenylbutylsulfonyl)amino-2-methylpropyl)-(hydroxy)phosphinoyl)propanoic acid, and 2-(3-(amino)methylphenyl)-3-((1-(2-phenylethenylsulfonyl)amino-2-methylpropyl)-(hydroxy)phosphinoyl)propanoic acid.

Of the preferred subgroup of compounds as set forth above, another preferred class is that class of compounds of formula (I) wherein:

$R^1$ is hydrogen;
$R^2$ is —P(O)(OR$^5$)—R$^7$—N(R$^5$)—S(O)$_2$—R$^9$;
$R^3$ is tetrazole, —C(O)OR$^6$, or —C(O)O—R$^7$—OC(O)R$^5$;
$R^4$ is aryl optionally substituted by one or more substituents selected from the group consisting of alkyl, halo, nitro, cyano, —N(R$^6$)$_2$, —R$^7$—N(R$^6$)$_2$, —N(R$^6$)—C(O)OR$^8$; —R$^7$—N(R$^6$)—C(O)OR$^8$, and —N(R$^5$)—C(NR$^5$)—N(R$^5$)$_2$;
each $R^5$ is independently hydrogen, alkyl or aralkyl;
each $R^6$ is independently hydrogen, alkyl, alkenyl, alkynyl, aryl, aralkyl or aralkenyl;
each $R^7$ is independently a straight or branched alkylene chain optionally substituted by hydroxy, mercapto, alkylthio, aryl, cycloalkyl, —N(R$^6$)$_2$, —C(O)OR$^6$, or —C(O)N(R$^6$)$_2$,
each $R^8$ is independently alkyl, alkenyl, aryl, aralkyl or aralkenyl; and
$R^9$ is aryl (optionally substituted by alkyl, aryl, aralkyl, hydroxy, alkoxy, cyano, nitro, halo, haloalkoxy, —N(R$^6$)$_2$, —C(O)OR$^6$, —C(O)N(R$^6$)$_2$ or —N(R$^6$)C(O)R$^6$).

Of this class of compounds of formula (I), preferred compounds are selected from the group consisting of the following:

2-(3-(amino)methylphenyl)-3-((1-(naphth-1-ylsulfonyl)amino-2-methylpropyl)(hydroxy)-phosphinoyl)propanoic acid;

2-(3-(amino)methylphenyl)-3-((1-(3-trifluoromethylphenylsulfonyl)amino-2-methyl-propyl)(hydroxy)phosphinoyl) propanoic acid;

2-(3-(amino)methylphenyl)-3-((1-(4-pentylphenylsulfonyl)amino-2-methylpropyl)-(hydroxy)phosphinoyl)propanoic acid;

2-(3-(amino)methylphenyl)-3-((1-(4-acetamidophenylsulfonyl)amino-2-methylpropyl)-(hydroxy)phosphinoyl)propanoic acid;

2-(3-(amino)methylphenyl)-3-((1-(4-phenylphenylsulfonyl)amino-2-methylpropyl)-(hydroxy)phosphinoyl)propanoic acid; and 2-(3-(amino)methylphenyl)-3-((1-(phenylsulfonyl)amino-2-methylpropyl)(hydroxy)-phosphinoyl)propanoic acid.

Of the preferred subgroup of compounds as set forth above, another preferred class is that class of compounds of formula (I) wherein:

$R^1$ is hydrogen;
$R^2$ is —P(O)(OR$^5$)—R$^7$—N(R$^5$)—S(O)$_2$—R$^9$;
$R^3$ is tetrazole, —C(O)OR$^6$, or —C(O)O—R$^7$—OC(O)R$^5$;
$R^4$ is aryl optionally substituted by one or more substituents selected from the group consisting of alkyl, halo, nitro, cyano, —N(R$^6$)$_2$, —R$^7$—N(R$^6$)$_2$, —N(R$^6$)—C(O)OR$^8$; —R$^7$—N(R$^6$)—C(O)OR$^8$, —N(R$^6$)—C(O)—R$^6$, —R$^7$—N(R$^6$)—C(O)—R$^6$, and —N(R$^5$)—C(NR$^5$)—N(R$^5$)$_2$;
each $R^5$ is independently hydrogen, alkyl or aralkyl;
each $R^6$ is independently hydrogen, alkyl, alkenyl, alkynyl, aryl, aralkyl or aralkenyl;
each $R^7$ is independently a straight or branched alkylene chain (optionally substituted by hydroxy, mercapto, alkylthio, aryl, cycloalkyl, —N(R$^6$)$_2$, —C(O)OR$^6$, or —C(O)N(R$^6$)$_2$),
each $R^8$ is independently alkyl, alkenyl, aryl, aralkyl or aralkenyl; and
$R^9$ is —R$^7$—N(R$^6$)—C(O)OR$^8$.

Of this class of compounds of formula (I), a preferred compound is 2-(3-(amino)methylphenyl)-3-((1-(3-phenyl-2-(benzyloxycarbonyl)aminopropyl-sulfonyl)amino-2-methylpropyl)(hydroxy)phosphinoyl)propanoic acid.

Of the preferred subgroup of compounds as set forth above, another preferred class is that class of compounds of formula (I) wherein:

$R^1$ is hydrogen;
$R^2$ is —P(O)(OR$^5$)—R$^7$—N(R$^5$)—S(O)$_2$—R$^9$;
$R^3$ is tetrazole, —C(O)OR$^6$, or —C(O)O—R$^7$—OC(O)R$^5$;
$R^4$ is aryl optionally substituted by one or more substituents selected from the group consisting of alkyl, halo, nitro, cyano, —N(R$^6$)$_2$, —R$^7$—N(R$^6$)$_2$, —N(R$^6$)—C(O)OR$^8$; —R$^7$—N(R$^6$)—C(O)OR$^8$, —N(R$^6$)—C(O)—R$^6$, —R$^7$—N(R$^6$)—C(O)—R$^6$, and —N(R$^5$)—C(NR$^5$)—N(R$^5$)$_2$;

each $R^5$ is independently hydrogen, alkyl or aralkyl;
each $R^6$ is independently hydrogen, alkyl, alkenyl, alkynyl, aryl, aralkyl or aralkenyl;
each $R^7$ is independently a straight or branched alkylene chain (optionally substituted by hydroxy, mercapto, alkylthio, aryl, cycloalkyl, —N($R^6$)$_2$, —C(O)O$R^6$, or —C(O)N($R^6$)$_2$),
each $R^8$ is independently alkyl, alkenyl, aryl, aralkyl or aralkenyl; and
$R^9$ is N-heterocyclyl (optionally substituted by alkyl, aryl, aralkyl, hydroxy, alkoxy, cyano, nitro, halo, haloalkoxy, —N($R^6$)$_2$, —C(O)O$R^6$, —C(O)N($R^6$)$_2$ or —N($R^6$)C(O)$R^6$).

Of this class of compounds of formula (I), preferred compounds are selected from the group consisting of the following:
2-(3-(amino)methylphenyl)-3-((1-(thien-2-ylsulfonyl)amino-2-methylpropyl)-(hydroxy)phosphinoyl)propanoic acid; and
2-(3-(amino)methylphenyl)-3-((1-(benzothiadiazolylsulfonyl)amino-2-methylpropyl)-(hydroxy)phosphinoyl)propanoic acid.

Of the compounds of formula (I) as set forth above in the Summary of the Invention, another preferred group is that group of compounds of formula (I) wherein:
$R^1$ is hydrogen;
$R^2$ is —P(O)(O$R^5$)—$R^7$—N($R^5$)—C(O)O$R^8$;
$R^3$ is —C(O)O$R^6$;
$R^4$ is unsubstituted phenyl or unsubstituted N-heterocyclyl;
each $R^5$ is independently hydrogen, alkyl or aralkyl;
each $R^6$ is independently hydrogen, alkyl, alkenyl, alkynyl, aryl, aralkyl or aralkenyl;
each $R^7$ is a straight or branched alkylene chain optionally substituted by aryl, —N($R^6$)$_2$ or —C(O)O$R^6$; and
$R^8$ is alkyl, alkenyl, aryl, aralkyl or aralkenyl.

Of this group of compounds of formula (I), preferred compounds are selected from the group consisting of the following:
2-phenyl-3-((1-(benzyloxycarbonyl)amino-2-methylpropyl)(hydroxy)phosphinoyl)-propanoic acid;
2-tetrahydroisoquinolinyl-3-((1-(benzyloxycarbonyl)amino-2-methylpropyl)-(hydroxy)phosphinoyl)propanoic acid.

Of the compounds of formula (II) as set forth above in the Summary of the Invention, a preferred group is that group of compounds of formula (II) wherein:
$R^1$ is hydrogen;
$R^2$ is —P(O)(O$R^5$)$R^6$, —P(O)(O$R^5$)—$R^7$—N($R^6$)$_2$, or —P(O)(O$R^5$)—$R^7$—N($R^5$)—C(S)—N($R^6$)$_2$;
$R^3$ is tetrazole, —C(O)O$R^6$ or —C(O)O—$R^7$—OC(O)$R^5$;
$R^4$ is aryl optionally substituted by one or more substituents selected from the group consisting of alkyl, halo, nitro, cyano, —N($R^6$)$_2$, —$R^7$—N($R^6$)$_2$, —N($R^6$)—C(O)O$R^8$, —$R^7$—N($R^6$)—C(O)O$R^8$, —N($R^6$)C(O)—$R^6$, —$R^7$—N($R^6$)—C(O)—$R^6$, —C(O)—N($R^6$)$_2$, —C(O)—$R^7$—N($R^6$)$_2$, —N($R^5$)—C(N$R^5$)—N($R^5$)$_2$, —N($R^5$)—C(O)—N($R^6$)$_2$ and —N($R^5$)—C(O)—$R^7$—N($R^6$)$_2$);
each $R^5$ is independently hydrogen, alkyl or aralkyl;
each $R^6$ is independently hydrogen, alkyl, alkenyl, alkynyl, aryl, aralkyl or aralkenyl;
each $R^7$ is a straight or branched alkylene chain (optionally substituted by hydroxy, mercapto, alkylthio, aryl, cycloalkyl, —N($R^6$)$_2$, —C(O)O$R^6$, or —C(O)N($R^6$)$_2$); and
each $R^8$ is independently alkyl, alkenyl, aryl, aralkyl or aralkenyl.

Of this group of compounds of formula (II), preferred compounds are selected from the group consisting of the following:
2-(3-guanidinophenyl)-2-((1-(2-phenylethyl)amino-2-methylpropyl)-(hydroxy)phosphinoyloxy)ethanoic acid;
2-(3-aminophenyl)-2-((phenyl)(hydroxy)phosphinoyloxy)ethanoic acid;
2-(3-guanidinophenyl)-2-((1-amino-2-methylpropyl)(hydroxy)phosphinoyloxy)ethanoic acid; and
2-(3-guanidinophenyl)-2-((1-(benzylaminothiocarbonyl)amino-2-methylpropyl)-(hydroxy)phosphinoyloxy)ethanoic acid.

Of the compounds of formula (II) as set forth above in the Summary of the Invention, another preferred group is that group of compounds of formula (II) wherein:
$R^1$ is hydrogen;
$R^2$ is —P(O)(O$R^5$)—$R^7$—N($R^5$)—S(O)$_2$—$R^9$;
$R^3$ is tetrazole, —C(O)O$R^6$ or —C(O)O—$R^7$—OC(O)$R^5$;
$R^4$ is aryl optionally substituted by one or more substituents selected from the group consisting of alkyl, halo, nitro, cyano, —N($R^6$)$_2$, —$R^7$—N($R^6$)$_2$, —N($R^6$)—C(O)O$R^8$, —$R^7$—N($R^6$)—C(O)O$R^8$, —N($R^6$)C(O)—$R^6$, —$R^7$—N($R^6$)—C(O)—$R^6$, —C(O)—N($R^6$)$_2$, —C(O)—$R^7$—N($R^6$)$_2$, —N($R^5$)—C(N$R^5$)—N($R^5$)$_2$, —N($R^5$)—C(O)—N($R^6$)$_2$ and —N($R^5$)—C(O)—$R^7$—N($R^6$)$_2$);
each $R^5$ is independently hydrogen, alkyl or aralkyl;
each $R^6$ is independently hydrogen, alkyl, alkenyl, alkynyl, aryl, aralkyl or aralkenyl;
each $R^7$ is a straight or branched alkylene chain (optionally substituted by hydroxy, mercapto, alkylthio, aryl, cycloalkyl, —N($R^6$)$_2$, —C(O)O$R^6$, or —C(O)N($R^6$)$_2$);
each $R^8$ is independently alkyl, alkenyl, aryl, aralkyl or aralkenyl; and
$R^9$ is alkyl (optionally substituted by hydroxy, alkoxy, aralkoxy, haloalkoxy, cyano, nitro, —N($R^6$)$_2$, —C(O)O$R^6$, —C(O)N($R^6$)$_2$ or —N($R^6$)C(O)$R^6$), alkenyl (optionally substituted by hydroxy, alkoxy, haloalkoxy, cyano, nitro, —N($R^6$)$_2$, —C(O)O$R^6$, —C(O)N($R^6$)$_2$ or —N($R^6$)C(O)$R^6$), aralkyl (wherein the aryl group is optionally substituted by alkyl, aryl, aralkyl, hydroxy, alkoxy, cyano, nitro, halo, haloalkoxy, —N($R^6$)$_2$, —C(O)O$R^6$, —C(O)N($R^6$)$_2$ or —N($R^6$)C(O)$R^6$), aralkenyl (wherein the aryl group is optionally substituted by alkyl, aryl, aralkyl, hydroxy, alkoxy, cyano, nitro, halo, haloalkoxy, —N($R^6$)$_2$, —C(O)O$R^6$, —C(O)N($R^6$)$_2$ or —N($R^6$)C(O)$R^6$).

Of this group of compounds of formula (II), preferred compounds are selected from the group consisting of the following:
2-(3-guanidinophenyl)-2-((1-(benzylsulfonyl)amino-2-methylpropyl)(hydroxy)-phosphinoyloxy)ethanoic acid; and
2-(3-guanidinophenyl)-2-((1-(2-phenylethenylsulfonyl)amino-2-methylpropyl)-(hydroxy)phosphinoyloxy)ethanoic acid.

Of the compounds of formula (II) as set forth above in the Summary of the Invention, another preferred group is that group of compounds of formula (II) wherein:
$R^1$ is hydrogen;
$R^2$ is —P(O)(O$R^5$)$_2$, —P(O)(O$R^5$)$R^6$, —P(O)(O$R^5$)—$R^7$—N($R^6$)$_2$, —P(O)(O$R^5$)—$R^7$—C(O)—$R^8$, —P(O)(O$R^5$)—$R^7$—N($R^5$)—C(O)O$R^8$, —P(O)(O$R^5$)—$R^7$—N($R^5$)—C(O)—$R^7$—N($R^5$)—C(O)O$R^8$, —P(O)(O$R^5$)—$R^7$—N($R^5$)—S(O)$_2$—$R^9$, or —P(O)(O$R^5$)—$R^7$—N($R^5$)—C(S)—N($R^6$)$_2$;
$R^3$ is tetrazole;
$R^4$ is aryl optionally substituted by one or more substituents selected from the group consisting of alkyl, halo, nitro, cyano, —N($R^6$)$_2$, —$R^7$—N($R^6$)$_2$, —N($R^6$)—C(O)O$R^8$, —R$^7$—N(R$^6$)—C(O)OR$^8$, —N(R$^6$)—C(O)—R$^6$, —R$^7$—N(R$^6$)—C(O)—R$^6$, —C(O)—N(R$^6$)$_2$, —C(O)—R$^7$—N(R$^6$)$_2$, —N(R$^5$)—C(NR$^5$)—N(R$^5$)$_2$, —N(R$^5$)—C(O)—N(R$^6$)$_2$ and —N(R$^5$)—C(O)—R$^7$—N(R$^6$)$_2$);

or R$^4$ is N-heterocyclyl wherein a carbon atom in the N-heterocyclyl may be optionally substituted by alkyl, halo, nitro, cyano, —N(R$^6$)$_2$, —R$^7$—N(R$^6$)$_2$, —N(R$^6$)—C(O)OR$^8$, —R$^7$—N(R$^6$)—C(O)OR$^8$, —N(R$^6$)—C(O)—R$^6$, —R$^7$—N(R$^6$)—C(O)—R$^6$, —C(O)—N(R$^6$)$_2$, —C(O)—R$^7$—N(R$^6$)$_2$, —N(R$^5$)—C(NR$^5$)—N(R$^5$)$_2$, —N(R$^5$)—C(O)—N(R$^6$)$_2$ or —N(R$^5$)—C(O)—R$^7$—N(R$^6$)$_2$), or wherein a nitrogen atom in the N-heterocyclyl may be optionally substituted by —C(NR$^5$)—N(R$^5$)$_2$, —C(NR$^5$)—R$^6$, —C(O)—N(R$^6$)$_2$ or —C(O)—R$^7$—N(R$^6$)$_2$;

each R$^5$ is independently hydrogen, alkyl or aralkyl;

each R$^6$ is independently hydrogen, alkyl, alkenyl, alkynyl, aryl, aralkyl or aralkenyl;

each R$^7$ is independently cycloalkylene (optionally substituted by alkyl), a straight or branched alkylene chain (optionally substituted by hydroxy, mercapto, alkylthio, aryl, cycloalkyl, —N(R$^6$)$_2$, —C(O)OR$^6$, or —C(O)N(R$^6$)$_2$), or a straight or branched alkenylene chain (optionally substituted by hydroxy, mercapto, alkylthio, aryl, cycloalkyl, —N(R$^6$)$_2$, —C(O)OR$^6$, or —C(O)N(R$^6$)$_2$);

each R$^8$ is independently alkyl, alkenyl, aryl, aralkyl or aralkenyl; and

R$^9$ is —R$^7$N(R$^6$)C(O)OR$^8$, haloalkyl, alkyl (optionally substituted by hydroxy, alkoxy, aralkoxy, haloalkoxy, cyano, nitro, —N(R$^6$)$_2$, —C(O)OR$^6$, —C(O)N(R$^6$)$_2$ or —N(R$^6$)C(O)R$^6$), alkenyl (optionally substituted by hydroxy, alkoxy, haloalkoxy, cyano, nitro, —N(R$^6$)$_2$, —C(O)OR$^6$, —C(O)N(R$^6$)$_2$ or —N(R$^6$)C(O)R$^6$), aryl (optionally substituted by alkyl, aryl, aralkyl, hydroxy, alkoxy, cyano, nitro, halo, haloalkoxy, —N(R$^6$)$_2$, —C(O)OR$^6$, —C(O)N(R$^6$)$_2$ or —N(R$^6$)C(O)R$^6$), aralkyl (wherein the aryl group is optionally substituted by alkyl, aryl, aralkyl, hydroxy, alkoxy, cyano, nitro, halo, haloalkoxy, —N(R$^6$)$_2$, —C(O)OR$^6$, —C(O)N(R$^6$)$_2$ or —N(R$^6$)C(O)R$^6$), aralkenyl (wherein the aryl group is optionally substituted by alkyl, aryl, aralkyl, hydroxy, alkoxy, cyano, nitro, halo, haloalkoxy, —N(R$^6$)$_2$, —C(O)OR$^6$, —C(O)N(R$^6$)$_2$ or —N(R$^6$)C(O)R$^6$), or N-heterocyclyl (optionally substituted by alkyl, aryl, aralkyl, hydroxy, alkoxy, cyano, nitro, halo, haloalkoxy, —N(R$^6$)$_2$, —C(O)OR$^6$, —C(O)N(R$^6$)$_2$ or —N(R$^6$)C(O)R$^6$).

Of this group of compounds of formula (II), a preferred compound is 2-methyl-1-[1-(3-guanidinophenyl)-1-tetrazolylmethoxy](hydroxy)phosphinoyl-propylcarbamic acid, benzyl ester.

Of the compounds of formula (III) as set forth above in the Summary of the Invention, a preferred group is that group of compounds of formula (III) wherein:

X is —O—;

R$^2$ is —P(O)(OR$^5$)—R$^7$—N(R$^5$)—C(O)OR$^8$; and

R$^4$ is aryl optionally substituted by one or more substituents selected from the group consisting of alkyl, halo, nitro, cyano, —N(R$^6$)$_2$, —R$^7$—N(R$^6$)$_2$, —N(R$^6$)—C(O)OR$^8$, —R$^7$—N(R$^6$)—C(O)OR$^8$, —N(R$^6$)C(O)—R$^6$, —R$^7$—N(R$^6$)—C(O)—R$^6$, —C(O)—N(R$^6$)$_2$, —C(O)—N(R$^6$)—N(R$^6$)$_2$, —C(O)—R$^7$—N(R$^6$)$_2$, —N(R$^5$)—C(NR$^5$)—N(R$^5$)$_2$, —N(R$^5$)—C(O)—N(R$^6$)$_2$ and —N(R$^5$)—C(O)—R$^7$—N(R$^6$)$_2$).

Of this group of compounds of formula (III), preferred compounds are selected from the group consisting of the following:

2-(3-guanidinophenyl)-2-((1-(benzyloxycarbonyl)aminoethyl)(hydroxy)-phosphinoyloxy)ethanoic acid;

2-(3-guanidinophenyl)-2-(((benzyloxycarbonyl)aminomethyl)(hydroxy)-phosphinoyloxy)ethanoic acid;

2-(3-guanidinophenyl)-2-((1-(benzyloxycarbonyl)amino-2-methylpropyl)(hydroxy)-phosphinoyloxy)ethanoic acid;

2-(3-guanidinophenyl)-2-((1-(benzyloxycarbonyl)aminohexyl)(hydroxy)-phosphinoyloxy)ethanoic acid;

2-(3-aminophenyl)-2-((1-(benzyloxycarbonyl)amino-2-methylpropyl)-(hydroxy)phosphinoyloxy)ethanoic acid, 2-(3-guanidinophenyl)-2-((1-(benzyloxycarbonyl)amino-3-methylbutyl)-(hydroxy)phosphinoyloxy)ethanoic acid;

2-(2-chloro-3-guanidinophenyl)-2-((1-(benzyloxycarbonyl)amino-2-methylpropyl)-(hydroxy)phosphinoyloxy)ethanoic acid;

2-(3-guanidinophenyl)-2-((1-(benzyloxycarbonyl)amino-1-phenylmethyl)-(hydroxy)phosphinoyloxy)ethanoic acid;

2-(2-fluoro-3-guanidinophenyl)-2-((1-(benzyloxycarbonyl)amino-2-methylpropyl)-(hydroxy)phosphinoyloxy)ethanoic acid;

2-(3-guanidinophenyl)-2-((1-(benzyloxycarbonyl)amino-1-cyclohexylmethyl)-(hydroxy)phosphinoyloxy)ethanoic acid;

2-(2-methyl-3-guanidinophenyl)-2-((1-(benzyloxycarbonyl)amino-2-methylpropyl)-(hydroxy)phosphinoyloxy)ethanoic acid;

2-(3-(amino)methylphenyl)-2-((1-(benzyloxycarbonyl)amino-2-methylpropyl)-(hydroxy)phosphinoyloxy)ethanoic acid;

2-(3-(guanidinomethyl)phenyl)-2-((1-(benzyloxycarbonyl)amino-2-methylpropyl)-(hydroxy)phosphinoyloxy)ethanoic acid;

2-(3-(1-iminoethylaminophenyl))-2-((1-(benzyloxycarbonyl)amino-2-methylpropyl)-(hydroxy)phosphinoyloxy) ethanoic acid;

2-(3-(t-butoxycarbonylamino)methylphenyl)-2-((1-(benzyloxycarbonyl)amino-2-methylpropyl)(hydroxy)phosphinoyloxy)ethanoic acid;

2-(3-(ethoxycarbonylamino)methylphenyl)-2-((1-(benzyloxycarbonyl)amino-2-methylpropyl)(hydroxy)phosphinoyloxy)ethanoic acid;

2-(3-(isopropoxycarbonylamino)methylphenyl)-2-((1-(benzyloxycarbonyl)amino-2-methylpropyl)(hydroxy)phosphinoyloxy)ethanoic acid;

2-(3-(2,2-dimethylpropylcarbonylamino)methylphenyl)-2-((1-(benzyloxycarbonyl)-amino-2-methylpropyl)(hydroxy)phosphinoyloxy)ethanoic acid;

2-(3-guanidinophenyl)-2-((1-(2-phenylethylcarbonyl)amino-2-methylpropyl)-(hydroxy)phosphinoyloxy)ethanoic acid; and 2-(3-guanidinophenyl)-2-((1-(2-phenylethenylcarbonyl)amino-2-methylpropyl)-(hydroxy)phosphinoyloxy)ethanoic acid.

Of the compounds of formula (III) as set forth above in the Summary of the Invention, another preferred group is that group of compounds of formula (III) wherein:

X is —O—;

R$^2$ is —P(O)(OR$^5$)—R$^7$—N(R$^5$)—C(O)—R$^7$—N(R$^5$)—C(O)OR$^8$; and

R$^4$ is aryl optionally substituted by one or more substituents selected from the group consisting of alkyl, halo, nitro, cyano, —N(R$^6$)$_2$, —R$^7$—N(R$^6$)$_2$, —N(R$^6$)—C(O)OR$^8$, —R$^7$—N(R$^6$)—C(O)OR$^8$, —N(R$^6$)—C(O)—R$^6$, —R$^7$—N(R$^6$)—C(O)—R$^6$, —C(O)—N(R$^6$)$_2$, —C(O)—N(R$^6$)—N(R$^6$)$_2$, —C(O)—R$^7$—N(R$^6$)$_2$, —N(R$^5$)—C(NR$^5$)—N(R$^5$)$_2$, —N(R$^5$)—C(O)—N(R$^6$)$_2$ and —N(R$^5$)—C(O)—R$^7$—N(R$^6$)$_2$).

Of this group of compounds of formula (III), preferred compounds are selected from the group consisting of the following:

2-(3-guanidinophenyl)-2-[(1-(1-benzyloxycarbonylamino-2-(4-hydroxyphenyl)-ethylcarbonyl)amino-2-methylpropyl)(hydroxy)phosphinoyloxy]ethanoic acid;

2-(3-guanidinophenyl)-2-[(1-(1-benzyloxycarbonylamino-2-phenylethylcarbonyl)amino-2-methylpropyl)(hydroxy)phosphinoyloxy]ethanoic acid;

2-(2-fluoro-3-guanidinophenyl)-2-[(1-(1-benzyloxycarbonylamino-2-phenyl-ethylcarbonyl)amino-2-methylpropyl)(hydroxy)phosphinoyloxy]ethanoic acid;

2-(3-guanidinophenyl)-2-[(1-(1-phenylcarbonylamino-2-phenylethylcarbonyl)amino-2-methylpropyl)(hydroxy)phosphinoyloxy]ethanoic acid;

2-(3-guanidinophenyl)-2-[(1-(1-ethoxycarbonylamino-2-phenylethylcarbonyl)amino-2-methylpropyl)(hydroxy)phosphinoyloxy]ethanoic acid;

2-(3-guanidinophenyl)-2-[(1-(1-benzyloxycarbonylamino-3-phenylpropyl-carbonyl)amino-2-methylpropyl)(hydroxy)phosphinoyloxy]ethanoic acid; and 2-(3-(amino)methylphenyl)-2-[(1-(1-benzyloxycarbonylamino-3-phenylpropyl-carbonyl)amino-2-methylpropyl)(hydroxy)phosphinoyloxy]ethanoic acid.

Of the compounds of formula (III) as set forth above in the Summary of the Invention, another preferred group is that group of compounds of formula (III) wherein:

X is —CH$_2$—;

R$^2$ is —P(O)(OR$^5$)—R$^7$—N(R$^5$)—C(O)R$^6$ or —P(O)(OR$^5$)—R$^7$—N(R$^5$)—C(O)OR$^8$; and R$^4$ is aryl optionally substituted by one or more substituents selected from the group consisting of alkyl, halo, nitro, cyano, —N(R$^6$)$_2$, —R$^7$—N(R$^6$)$_2$, —N(R$^6$)—C(O)OR$^8$, —R$^7$—N(R$^6$)—C(O)OR$^8$, —N(R$^6$)—C(O)—R$^6$, —R$^7$—N(R$^6$)—C(O)—R$^6$, —C(O)—N(R$^6$)$_2$, —C(O)—N(R$^6$)—N(R$^6$)$_2$, —C(O)—R$^7$—N(R$^6$)$_2$, —N(R$^5$)—C(NR$^5$)—N(R$^5$)$_2$, —N(R$^5$)—C(O)—N(R$^6$)$_2$ and —N(R$^5$)—C(O)—R$^7$—N(R$^6$$_2$).

Of this group of compounds of formula (III), preferred compounds are selected from the group consisting of the following:

2-(3-(amino)methylphenyl)-3-((1-(methylcarbonyl)amino-2-methylpropyl)(hydroxy)-phosphinoyl)propanoic acid;

2-(3-(hydrazinocarbonyl)phenyl)-3-((1-(benzyloxycarbonyl)amino-2-methylpropyl)-(hydroxy)phosphinoyl)propanoic acid;

2-(3-guanidinophenyl)-3-((1-(benzyloxycarbonyl)amino-3-methylbutyl)-(hydroxy)phosphinoyl)propanoic acid;

2-(3-guanidinophenyl)-3-(((benzyloxycarbonyl)aminomethyl)(hydroxy)-phosphinoyl)propanoic acid;

2-(3-guanidinophenyl)-3-((1-(benzyloxycarbonyl)aminoethyl)(hydroxy)-phosphinoyl)propanoic acid;

2-(3-guanidinophenyl)-3-((1-(benzyloxycarbonyl)amino-2-methylpropyl)(hydroxy)-phosphinoyl)propanoic acid;

2-(2-chloro-5-guanidinophenyl)-3-((1-(benzyloxycarbonyl)amino-2-methylpropyl)(hydroxy)phosphinoyl)propanoic acid;

2-(3-(amino)methylphenyl)-3-((1-(benzyloxycarbonyl)amino-2-methylpropyl)(hydroxy)-phosphinoyl)propanoic acid; and 2-(3-(amino)methylphenyl)-3-((1-(2-phenylethylcarbonyl)amino-2-methylpropyl)(hydroxy)phosphinoyl)propanoic acid.

Of the compounds of formula (III) as set forth above in the Summary of the Invention, another preferred group is that group of compounds of formula (III) wherein:

X is —CH$_2$—;

R$^2$ is —P(O)(OR$^5$)—R$^7$—N(R$^5$)—C(O)—R$^7$—N(R$^5$)—C(O)OR$^8$; and

R$^4$ is aryl optionally substituted by one or more substituents selected from the group consisting of alkyl, halo, nitro, cyano, —N(R$^6$)$_2$, —R$^7$—N(R$^6$)$_2$, —N(R$^6$)—C(O)OR$^8$, —R$^7$—N(R$^6$)—C(O)OR$^8$, —N(R$^6$)—C(O)—R$^6$, —R$^7$—N(R$^6$)—C(O)—R$^6$, —C(O)—N(R$^6$)$_2$, —C(O)—N(R$^6$)—N(R$^6$)$_2$, —C(O)—R$^7$—N(R$^6$)$_2$, —N(R$^5$)—C(NR$^5$)—N(R$^5$)$_2$, —N(R$^5$)—C(O)—N(R$^6$)$_2$ and —N(R$^5$)—C(O)—R$^7$—N(R$^6$$_2$).

Of this group of compounds of formula (III), preferred compounds are selected from the group consisting of the following:

2-(3-guanidinophenyl)-3-(((1-benzyloxycarbonylamino-2-phenylethyl)-carbonylaminomethyl)(hydroxy)phosphinoyl)propanoic acid; and 2-(3-guanidinophenyl)-3-(((1-benzyloxycarbonylamino-2-phenylethyl)-carbonylaminomethyl)(hydroxy)phosphinoyl)propanoic acid.

F. Preparation of the Compounds of the Invention

The compounds of the invention may be prepared by methods and processes known to one skilled in the art or by the processes disclosed herein. It is understood that in the following description, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (e.g., t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R$^8$ (where R$^8$ is alkyl, alkenyl, aryl, aralkyl or aralkenyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein.

The use of protecting groups is described in detail in Green, T. W. and P. G. M. Wutz, *Protective Groups in Organic Synthesis* (1991), 2nd Ed., Wiley-Interscience. The protecting group may also be a polymer resin such as a Wang resin or a 2-chlorotrityl chloride resin.

It will also be appreciated by those skilled in the art, although such protected derivatives of compounds of formulae (I), (II) and (III), as described above in the Summary of the Invention, may not possess pharmacological activity as such, they may be administered to a mammal having a disease-state characterized by thrombotic activity and thereafter metabolized in the body to form compounds of the invention which are pharmacologically active. Such derivatives may therefore be described as "prodrugs". All prodrugs of compounds of formulae (I), (II) and (III) are included within the scope of the invention.

For purposes of convenience, the following Reaction Schemes are directed to compounds of formulae (I) and (II). However, compounds of formulae (III) are prepared in similar manner by methods disclosed herein or by methods known to one of ordinary skill in the art.

1. Preparation of Compounds of Formula (Ia)

Compounds of formula (Ia) are compounds of formula (I) of the invention as described above in the Summary of the Invention wherein R$^1$ is hydrogen, R$^2$ is —SH or —S—C(O)—R$^8$, R$^3$ is —C(O)OR$^{6a}$ and R$^4$ is phenyl optionally substituted by halo and substituted by —R$^{7a}$—N(H)R$^{5a}$. Other R$^4$ aryl groups optionally substituted by one or more substitutents selected from the group consisting of alkyl, haloalkyl, haloalkoxy, mercapto, alkylthio, phenyl, cycloalkyl, nitro, cyano, —OR$^6$, —N(R$^6$)$_2$, —R$^7$—N(R$^6$)$_2$, —N(R$^6$)—C(O)OR$^8$, —R$^7$—N(R$^6$)—C(O)OR$^8$, —N(R$^6$)—C(O)—R$^6$, —R$^7$—N(R$^6$)—C(O)—R$^6$, —C(O)—N(R$^6$)$_2$, —C(O)—R$^7$—N(R$^6$)$_2$, —N(R$^5$)—C(NR$^5$)—N(R$^5$)$_2$, —N(R$^5$)—C(O)—N(R$^6$)$_2$ and —N(R$^5$)—C(O)—R$^7$—N(R$^6$$_2$) may be prepared in a similar manner, provided that functional groups are adequately protected by suitable protecting groups. Compounds of formula (Ia) are prepared as illustrated below in Reaction Scheme 1 where each PG$^1$ is independently a nitrogen protecting group, such as benzyloxycarbonyl or t-butoxycarbonyl; R$^5$ is as described above in the Summary of the Invention; R$^{6a}$ is alkyl, aryl or aralkyl; R$^{7a}$ is a bond or an branched or straight alkylene chain; R$^8$ is alkyl, aryl or aralkyl; and R$^{4a}$ is hydrogen or halo:

REACTION SCHEME 1

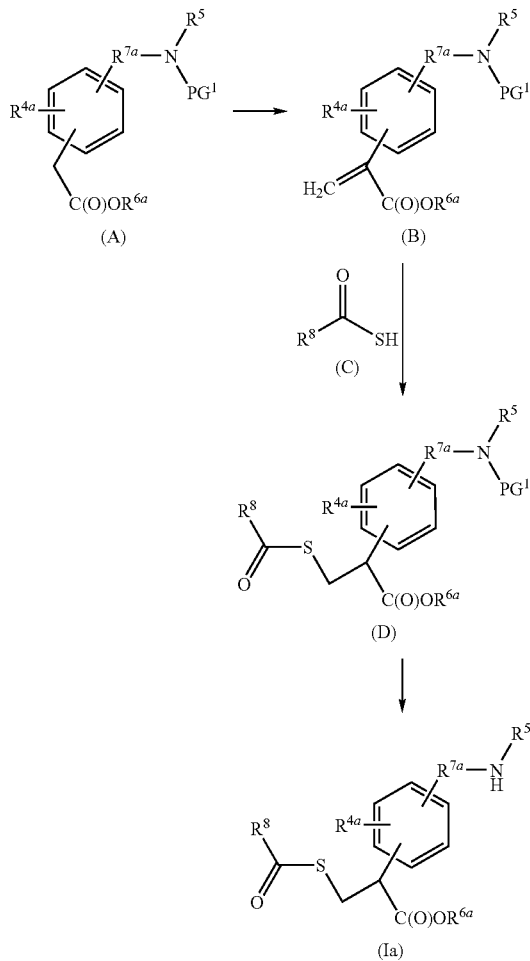

Compounds of formula (A) and formula (C) are commercially available, for example, from Aldrich Chemical Co., or may be prepared according to methods known to one skilled in the art.

In general, the compounds of formula (Ia), (Ib), and (Ic) are prepared by first treating a compound of formula (A) in an aprotic solvent such as toluene with paraformaldehyde in the presence of a base, preferably potassium carbonate, and a phase transfer catalyst, such as tetrabutylammonium iodide, at temperatures of between about 50° C. and about 110° C., preferably at about 100° C., for about 1 to about 6 hours, preferably for about 4 hours, to form a compound of formula (B), which is isolated from the reaction mixture by standard isolation techniques, such as filtration, evaporation of solvents, and purification by flash chromatography.

The compound of formula (B) in an aprotic solvent, such as chloroform, is then treated with a compound of formula (C) in the presence of at temperatures of between about 0° C. and about 100° C., preferably at about ambient temperature, for about 12 hours to about 18 hours, preferably for about 18 hours. The compound of formula (D) is then isolated from the reaction mixture by standard isolation techniques, such as evaporation of the solvents and purification by flash chromatography.

The compound of formula (D) in an aprotic solvent, such as methylene chloride was treated with an acid under standard hydrolysis conditions at temperatures of between about 0° C. and about 60° C., preferably at ambient temperature, for about 30 minutes to about an hour, preferably for about 30 minutes, to remove the nitrogen protecting group. The compound of formula (Ia) is then isolated from the reaction mixture by standard isolation techniques, such as evaporation of the solvents and purification by flash chromatography.

Compounds of formula (Ia) may be further treated with a strong aqueous base, such as aqueous ammonium hydroxide, to prepare compounds of formula (I) wherein R$^2$ is —SH. Compounds of formula (Ia) may also be treated under standard base hydrolysis conditions to form compounds of formula (Ia) wherein R$^{6a}$ is hydrogen (the free acid).

2. Preparation of Compounds of Formulae (Ib) and (Ic)

Compounds of formulae (Ib) and (Ic) are compounds of formula (I) of the invention as described above in the Summary of the Invention wherein R$^1$ is hydrogen, R$^2$ is —SH or —S—C(O)—R$^8$, R$^3$ is —C(O)OR$^{6a}$ and R$^4$ is phenyl optionally substituted by halo and substituted by —R$^{7a}$—N(H)R$^5$. Other R$^4$ aryl groups optionally substituted by one or more substitutents selected from the group consisting of alkyl, haloalkyl, haloalkoxy, mercapto, alkylthio, phenyl, cycloalkyl, nitro, cyano, —OR$^6$, —N(R$^6$)$_2$, —R$^7$—N(R$^6$)$_2$, —N(R$^6$)—C(O)OR$^8$, —R$^7$—N(R$^6$)—C(O)OR$^8$, —N(R$^6$)—C(O)—R$^6$, —R$^7$—N(R$^6$)—C(O)—R$^6$, —C(O)—N(R$^6$)$_2$, —C(O)—R$^7$—N(R$^6$)$_2$, —N(R$^5$)—C(NR$^5$)—N(R$^5$)$_2$, —N(R$^5$)—C(O)—N(R$^6$)$_2$ and —N(R$^5$)—C(O)—R$^7$—N(R$^6$$_2$) may be prepared in a similar manner, provided that functional groups are adequately protected by suitable protecting groups. Compounds of formulae (Ib) and (Ic) may be prepared as illustrated below in Reaction Scheme 2 where each PG$^1$ is independently a nitrogen protecting group, such as benzyloxycarbonyl or t-butoxycarbonyl; LG is an activating group such as trifluoromethylsulfonyl; R$^5$ is as described above in the Summary of the Invention; R$^{6a}$ is alkyl, aryl or aralkyl; R$^{7a}$ is a bond or an branched or straight alkylene chain; R$^8$ is alkyl, aryl or aralkyl; and X is hydrogen or halo:

REACTION SCHEME 2

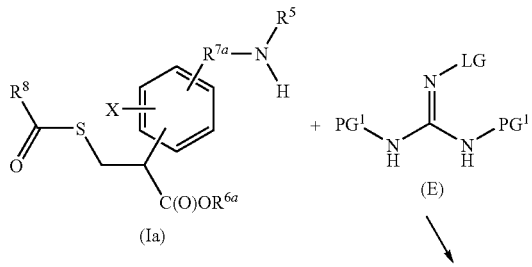

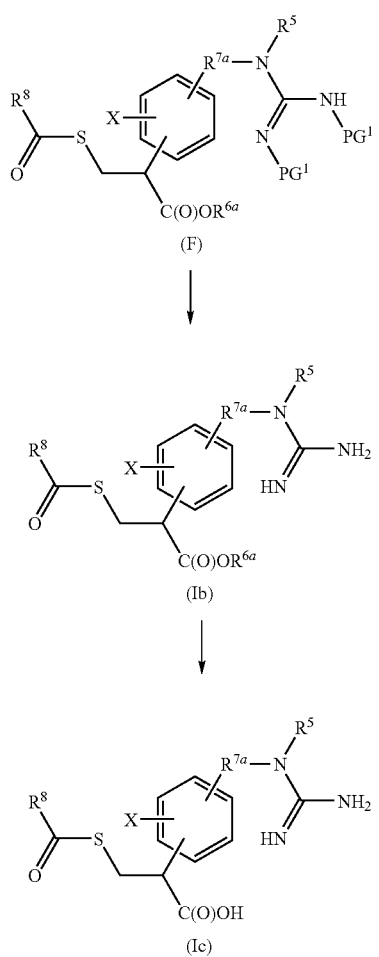

Compounds of formula (E) are commercially available, for example, from Aldrich Chemical Co., or may be prepared according to methods known to those of ordinary skill in the art, such as those described in Bernatowicz, M. S., *Tetrahedron Lett.* (1993), Vol. 34, p. 3389, or Wu, Y. et al., *Synth. Commun.* (1993), Vol. 23, p. 3055, or Drake, B. et al., *Synthesis* (1994), p. 579.

In general, compounds of formulae (Ib) and (Ic) are prepared by first treating a compound of formula (Ia), as prepared above, in an organic solvent, such as chloroform, in the presence of a base, such as diisopropylethylamine, followed by the addition of an equimolar amount of a compound of formula (E). The reaction mixture is stirred at a temperature of between about 0° C. and about 100° C., preferably at ambient temperature, for about 12 hours to about 18 hours, preferably for about 18 hours. The compound of formula (F) is isolated from the reaction mixture by standard isolation techniques, such as organic extraction, concentration of organic layers and purification by flash chromatography.

The nitrogen-protecting groups on the compound of formula (F) are then removed by standard deprotection techniques, such as acid hydrolysis in a protic solvent, such as ethanol, at temperatures between about 0° C. and about 100° C., preferably at about ambient temperature, for about 1 hour to about 18 hours, preferably for about 18 hours. The compound of formula (Ib) is then isolated from the reaction mixture by standard isolation techniques, such as evaporation of the solvents.

The compound of formula (Ib) in a polar protic solvent mixture, such as water, ethanol and tetrahydrofuran, at temperatures between about 0° C. and about 100° C., preferably at about ambient temperature, is then hydrolyzed under standard aqueous base hydrolysis conditions, such as treatment with lithium hydroxide, to form a compound of formula (Ic), which may be further treated with an acid to form the corresponding salt of a compound of formula (Ic).

3. Preparation of Compounds of Formulae (Id) and (Ie)

Compounds of formulae (Id) and (Ie) are compounds of formula (I) of the invention as described above in the Summary of the Invention wherein $R^1$ is hydrogen, $R^2$ is —SH or —S—C(O)—$R^8$, $R^3$ is —C(O)O$R^8$ and $R^4$ is 3(4)-piperidinyl. Other $R^4$ N-heterocyclyl groups wherein a carbon atom in the N-heterocyclyl group is optionally substituted by alkyl, halo, nitro, cyano, —N($R^6$)$_2$, —$R^7$—N($R^6$)$_2$, —N($R^6$)—C(O)O$R^8$, —$R^7$—N($R^6$)—C(O)O$R^8$, —N($R^6$)—C(O)—$R^6$, —$R^7$—N($R^6$)—C(O)—$R^6$, —C(O)—N($R^6$)$_2$, —C(O)—$R^7$—N($R^6$)$_2$, —N($R^5$)—C(N$R^5$)—N($R^5$)$_2$, —N($R^5$)—C(O)—N($R^6$)$_2$ or —N($R^5$)—C(O)—$R^7$—N($R^6$_2$), or wherein a nitrogen atom in the N-heterocyclyl may be optionally substituted by —C(N$R^5$)—N($R^5$)$_2$, —C(N$R^5$)—$R^6$, —C(O)—N($R^6$)$_2$ or —C(O)—$R^7$—N($R^6$)$_2$ may be prepared in a similar manner, provided that functional groups are adequately protected by suitable protecting groups. Compounds of formuale (Id) and (Ie) are prepared as illustrated below in Reaction Scheme 3 where PG$^1$ is a nitrogen protecting group, such as benzyloxycarbonyl; $R^{6a}$ is alkyl, aryl or aralkyl; $R^{7a}$ is a bond or a branched or straight alkylene chain optionally substituted by aryl, —N($R^6$)$_2$ or —C(O)O$R^6$; and $R^8$ is alkyl, aryl or aralkyl:

REACTION SCHEME 3

1.

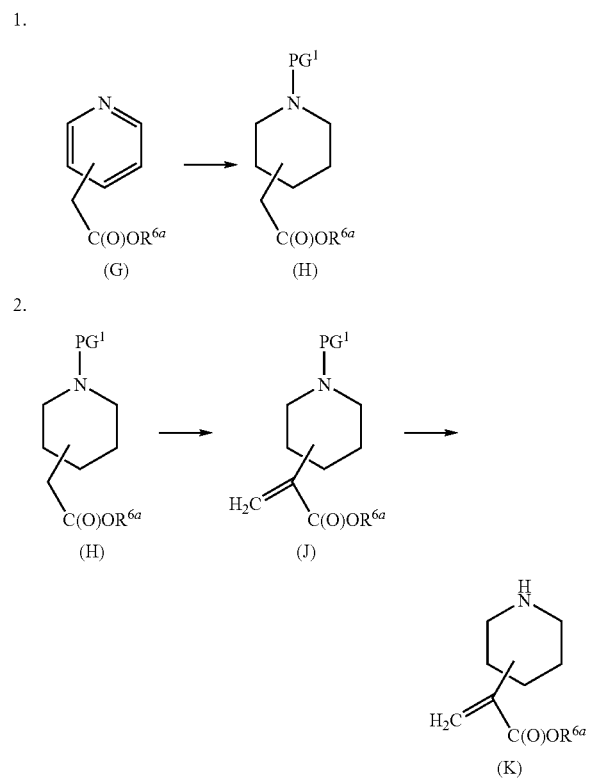

3.

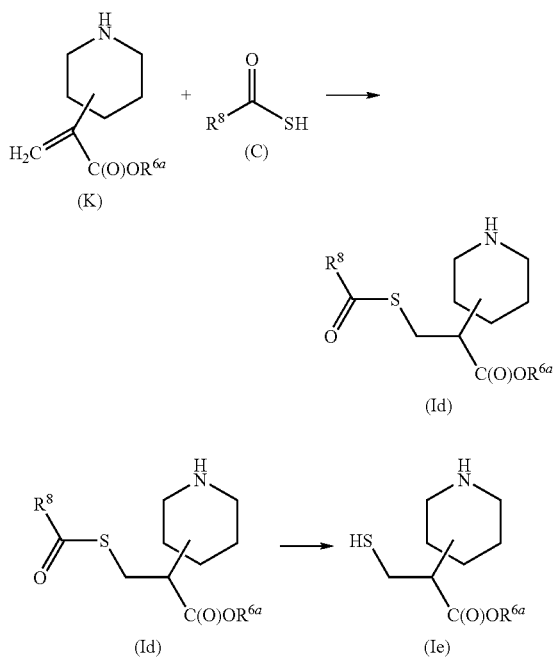

Compounds of formula (G) and formula (C) are commercially available, or may be prepared according to methods known to those skilled in the art.

In general, compounds of formula (Id) and formula (Ie) are prepared by first hydrogenating a compound of formula (G) in the presence of a catalyst, such as platinum oxide, and an acid, such as acetic acid. The resulting product is then basified by the addition of a base, such as sodium bicarbonate, and dissolved in a polar aprotic solvent, such as tetrahydrofuran. A nitrogen-protecting providing group is then added to the solvent and the resulting mixture is stirred for about 10 hours to about 18 hours, preferably for about 18 hours. The compound of formula (H) is then isolated from the reaction mixture by standard isolation techniques, such as concentration, organic solvent extraction, salt wash and concentration.

The compound of formula (H) is then added to a solution of a strong base, such as lithium diisopropylamide, in a polar aprotic solvent, such as tetrahydrofuran at temperatures between about −80° C. and about −70° C., preferably at about −78° C. The resulting reaction mixture was warmed to a temperature between about −5° C. and 5° C., preferably at about 0° C. over a period of about 1 hour to about 2 hours, preferably for a period of about 1.5 hours. Formaldehyde gas is then passed through the reaction mixture for a period of about 0.5 hours to about 1.0 hour, preferably for about 0.5 hours. The reaction is quenched by the addition of an acid, preferably HCl. The compound of formula (J) is then isolated from the reaction mixture by standard isolation techniques, such as evaporation of the solvents and purification through silica gel.

The compound of formula (J) is then de-protected under standard nitrogen deprotection conditions to form a compound of formula (K), which is isolated from the reaction mixture by standard isolation techniques.

The compound of formula (K) is then treated with a solution of a compound of formula (C) in a protic solvent, such as isopropyl alcohol, and the resulting reaction mixture is stirred for about 12 hours to about 24 hours, preferably for about 24 hours, at a temperature of between about 0° C. and about 100° C., preferably at about ambient temperature. The compound of formula (Id) is then isolated from the reaction mixture by standard isolation techniques, such as concentration.

The compound of formula (Id) is then treated with an aqueous base, such as ammonium hydroxide, under standard aqueous base hydrolysis conditions at temperatures of about 0° C. to about 80° C., preferably at about 0° C., to form compounds of formula (Ie), which are isolated from the reaction mixture as a salt under standard isolation techniques.

Compounds of formulae (K), (Id) and (Ie) may be further treated under similar conditions as described above in Reaction Scheme 2 with an appropriately substituted and activated guanidine to form compounds of formulae (K), (Id) and (Ie) wherein the piperidinyl group is substituted at the 1-position by —C(NR$^5$)—N(R$^5$)$_2$, following the methods disclosed in Feichtinger, K. et al., *J. Org. Chem.* (1998), Vol. 63, pp. 3804-3805. Alternatively, compounds of formulae (K), (Id) and (Ie) may be further treated with an appropriately substituted methyl acetimidate or derivative thereof to form compounds of formulae (K), (Id) and (Ie) wherein the piperidinyl group is substituted at the 1-position by —C(NR$^5$)—R$^6$. Alternatively, compounds of formulae (K), (Id) and (Ie) may be further treated with the appropriately substituted reagent under standard acylation or peptide coupling conditions to form compounds of formulae (K), (Id) and (Ie) wherein the piperidinyl group is substituted at the 1-position by —C(O)—N(R$^6$)$_2$ or —C(O)—R$^7$—N(R$^6$)$_2$.

4. Preparation of Compounds of Formula (If)

Compounds of formula (If) are compounds of formula (I) as described above in the Summary of the Invention wherein R$^1$ is hydrogen and R$^2$ is —P(O)(OR$^5$)—R$^6$. These compounds may be prepared as illustrated below in Reaction Scheme 4 where R$^{3a}$ is as described above in the Summary of the Invention for R$^3$ except that any free acids therein are in a suitably protected form (such as in an ester form); R$^{4a}$ is as described above in the Summary of the Invention for R$^4$ except that any reactive functional groups therein may be suitably protected; and R$^{6a}$ is as described above in the Summary of the Invention for R$^6$:

REACTION SCHEME 4

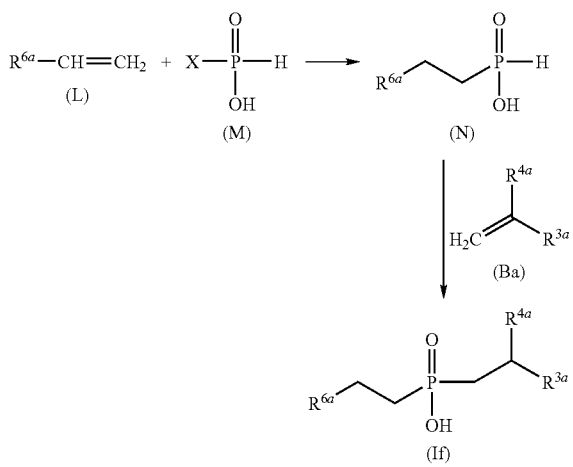

Compounds of formula (L) and formula (M) are commercially available, or may be prepared by methods known to those of ordinary skill in the art, or by methods disclosed herein. Compounds of formula (Ba) are prepared by methods described herein.

In general, compounds of formula (If) and formula (Ig) are prepared by first preparing a compound of formula (N) in a manner similar the methods described in Karanewsky, et al., *J. Med. Chem.* (1988), Vol. 31, p. 204, or by methods disclosed herein. For example, a solution of a compound of formula (L) and an excess molar amount of a compound of formula (M) in the presence of a radical initiator, such as 2,2′-azobisisobutyronitrile (AIBN), and a strong acid, such as concentrated sulfuric acid, in a protic solvent, such as ethanol, is heated to reflux for a period of about 12 hours to about 17 hours, preferably for a period of about 17 hours. The compound of formula (N) is then isolated from the reaction mixture by standard isolation techniques, such as organic extraction, evaporation of solvents, salt formation, filtration and concentration.

Compounds of formula (If) are prepared according to methods similar to those described in Boyd, et al., *Tetrahedron Lett.* (1990), pp. 2933-2936, or by methods disclosed herein. For example, the compound of formula (N) is activated by treatment with an excess molar mount of an activating agent, such as chlorotrimethylsilane, in the presence of a base, such as diisopropylethylamine. An equimolar amount of a compound of formula (Ba) is added to the reaction mixture, at a temperature of between about −30° C.° and about 50° C., preferably at about 0° C. The reaction mixture is allowed to warm to ambient temperature. The compound of formula (If) is then isolated from the reaction mixture by standard isolation techniques, such as organic extraction and concentration.

Compounds of formula (If) wherein $R^{4a}$ is phenyl substituted by an amino-protected guanidine group are prepared according to methods similar to those described in Feichtinger, K, et al., *J. Org. Chem.* (1998), Vol. 63, pp. 3804-3805, or by methods disclosed herein.

Alternatively, compounds of formula (Ba) or compounds of formula (B) (as described above in Reaction Scheme 1) may be treated with phosphonic acid esters of the formula $HP(O)(OR^5)_2$ by methods disclosed herein in order to prepare compounds of formula (I) wherein $R^2$ is $-P(O)(OR^5)_2$.

5. Preparation of Compounds of Formula (IIa)

Compounds of formula (IIa) are compounds of formula (II) as described above in the Summary of the Invention wherein $R^1$ is hydrogen and $R^3$ is $-C(O)OR^6$ (where $R^6$ is alkyl, aryl or aralkyl). They are prepared as illustrated below in Reaction Scheme 5 wherein $R^{4a}$ is as described above in the Summary of the Invention for $R^4$ except that any reactive functional groups therein may be suitably protected; at least one $R^5$ is hydrogen and the other is as described above in the Summary of the Invention; $R^{6a}$ is alkyl, aryl or aralkyl; and $R^{10}$ is $-R^6$, $-R^7-N(R^6)_2$, $-R^7-C(O)-R^8$, $-R^7-N(R^5)-C(O)OR^8$, or $-R^7-N(R^5)-C(O)-R^7-N(R^5)-C(O)OR^8$:

REACTION SCHEME 5

1.

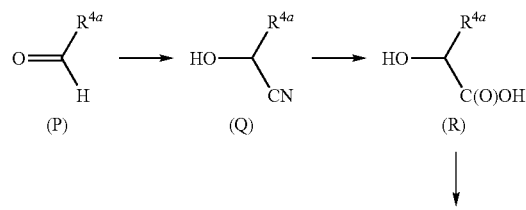

2.

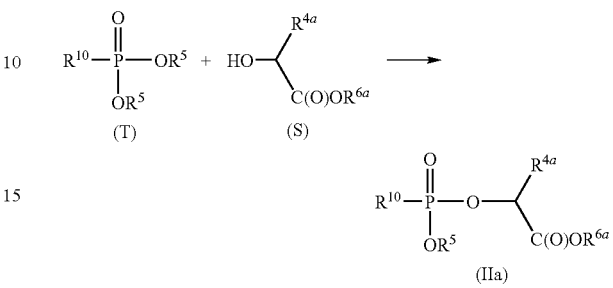

Compounds of formula (P) and formula (T) are commercially available, or may be prepared by methods known to one skilled in the art, or by methods disclosed herein.

In general, compound of formula (IIa) are prepared by first cooling a solution of a compound of formula (P) in a polar aprotic solvent, such as ether, to a temperature of between 0° C. and 10° C., preferably to a temperature of about 10° C. An excess molar amount of an alkaline metal cyanide, preferably potassium cyanide, is then added to the solution over a period of about 30 minutes to about 1 hour, preferably of about 30 minutes. The resulting reaction mixture is stirred for a period of about 30 minutes to about 1 hour, preferably for a period of 30 minutes. The compound of formula (Q) is then isolated from the reaction mixture by standard isolation techniques, such as phase separation, extraction, and concentration.

The compound of formula (Q) in a polar aprotic solvent, such as ether, is then hydrolyzed under standard nitrile hydrolysis conditions to form the compound of formula (R), which can then be treated under standard esterification conditions to form compounds of formula (S). Alternatively, the compound of formula (Q) is treated under standard nitrile hydrolysis conditions in the presence of an alcohol of the formula $HOR^{6a}$ to form compounds of formula (S) in situ.

The compound of formula (S) is then treated under standard dehydrating coupling conditions with a compound of formula (T) by methods similar to those described in Hoffman, M., *Synthesis* (1986), 557A to form a compound of formula (IIa), which is isolated from the reaction mixture by standard isolation techniques.

Compounds of formula (IIa) wherein $R^{4a}$ is aryl group substituted by $-N(R^6)_2$ where at least on $R^6$ is hydrogen may be further reacted with an appropriately substituted and activated guanidine-forming compound, to form compounds of the invention wherein $R^4$ is an aryl group substituted by $-N(R^5)-C(NR^5)-N(R^5)_2$.

6. Preparation of Compounds of Formulae (Ig), (Ih), (Ii), and (Ij)

Compounds of formulae (Ig), (Ih), (Ii), and (Ij) are compounds of formula (I) as described above in the Summary of the Invention wherein $R^1$ is hydrogen and $R^2$ is $-P(O)(OR^5)-R^7-N(R^6)_2$ or $-P(O)(OR^5)-R^7-N(R^5)-S(O)_2-R^9$ where each $R^5$, each $R^6$, $R^7$ and $R^9$ are as described above in the Summary of the Invention. These compounds are prepared as described below in Reaction Scheme 6 wherein X is halo; $PG^1$ and $PG^2$ are each independently nitrogen-protecting groups; $R^{6a}$ is alkyl, aryl or aralkyl; $R^{4a}$ is as described above in the Summary of the Invention for $R^4$ except that any reactive functional groups therein may be suitably protected; $R^{5a}$ is alkyl or aralkyl; and $R^7$ and $R^9$ are as described above in the Summary of the Invention:

REACTION SCHEME 6

1.

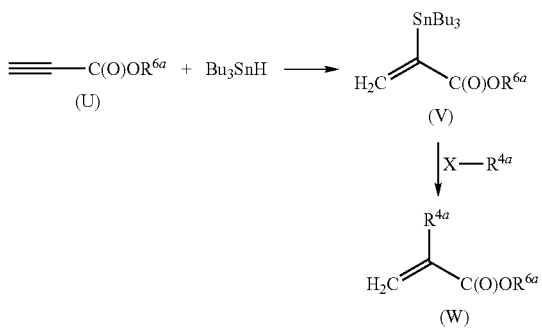

2.

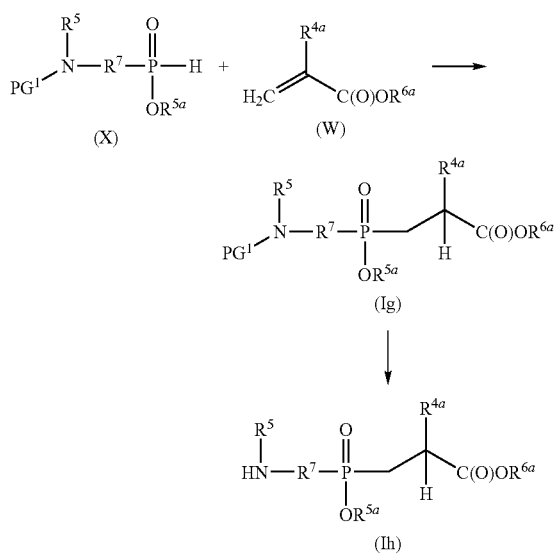

3.

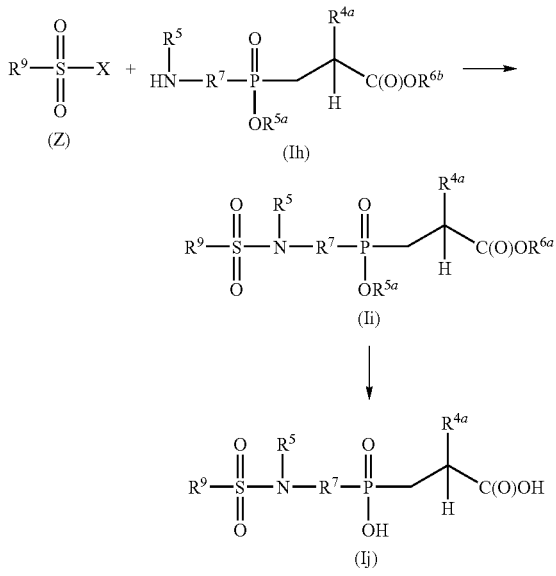

Compounds of formula (X), formula (W) and formula (Z) are prepared by methods disclosed herein or may be prepared according to methods known to one skilled in the art. Bu$_3$SnH is commercially available. Compounds of formula X—R$^{4a}$ are commercially available or may be prepared according to methods known to one skilled in the art, or by methods disclosed herein. Compounds of formula (V) are prepared in a similar manner as described in Cochran, J. C. et al., *Tetrahedron Letters* (1990), Vol. 31, pp. 6621-6624, and Miyake, H. et al., *Chem. Lett.* (1989), pp. 981-984. Compounds of formula (W) are prepared in a similar manner as described in Levin, J., *Tetrahedron Letters* (1993), Vol. 34, pp. 6211-6214.

In general, compounds of formulae (Ig), (Ih), (Ii), and (Ij) are prepared by first reacting a compound of formula (U) with tributyltin hydride in the presence of a palladium catalyst to afford the compound of formula (V). Stille coupling with the suitably protected compound of the formula X—R$^{4a}$ affords the compound of formula (W).

The compound of formula (W) in an aprotic solvent, such as methylene chloride, is then added to a solution of a compound of formula (X) in an aprotic solvent, such as methylene chloride, in the presence of a base, such as diisopropylethylamine, and an activating agent, such as chlorotrimethylsilane, at temperatures of between about −5° C. and 5° C., preferably at 0° C. The resulting reaction mixture is stirred at ambient temperature for a period of between about 12 hours and about 18 hours, preferably for a period of about 18 hours. The reaction is quenched and the compound of formula (Ig) is isolated from the reaction mixture by standard isolation techniques, such as extraction, evaporation and purification by flash chromatography.

The compound of formula (Ig) is then deprotected by standard nitrogen deprotection techniques, such as hydrogenation in the presence of a catalyst, such as Pd/C, to afford a compound of formula (Ih), which is isolated from the reaction mixture by standard isolation techniques, such as filtration.

The compound of formula (Ih) in an aprotic solvent, such as methylene chloride, in the presence of a base, such as diisopropylethylamine, and an acylation catalyst, such as DMAP, at temperatures at between about −20° C. and 80° C., preferably at about 0° C., is then treated with an excess molar amount of a compound of formula (Z) in an aprotic solvent, such as methylene chloride. The resulting reaction mixture is stirred for a period of about 0.5 hours to about 1.0 hour, preferably for about 0.5 hours, and then warmed to ambient temperature overnight. The compound of formula (Ii) is isolated from the reaction mixture by standard isolation techniques, such as evaporation of solvents.

The compound of formula (Ii) is then hydrolyzed to the compound of formula (Ij) by standard hydrolysis conditions.

Alternatively, appropriately substituted acid chlorides and isothiocyanates may be used in place of compounds of formula (Z) above to prepare compounds of the invention wherein $R^2$ is —P(O)(OR$^5$)—R$^7$—N(R$^5$)—C(O)OR$^8$, —P(O)(OR$^5$)—R$^7$—N(R$^5$)—C(O)—R$^7$—N(R$^5$)—C(O)OR$^8$ or —P(O)(OR$^5$)—R$^7$—N(R$^5$)—C(S)—N(R$^6$)$_2$.

7. Preparation of Compounds of Formula (X)

Compounds of formula (X) are intermediates in the preparation of compounds of formula (Ig) as described above. They are prepared as described below in Reaction Scheme 7 wherein $R^5$ and $R^7$ are as described above in the Summary of the Invention, $R^{5a}$ is alkyl or aralkyl, PG is an alkyl group, such as diphenylmethyl, that provides suitable protection for the nitrogen to which it is attached, and PG$^1$ is a nitrogen-protecting group:

REACTION SCHEME 7

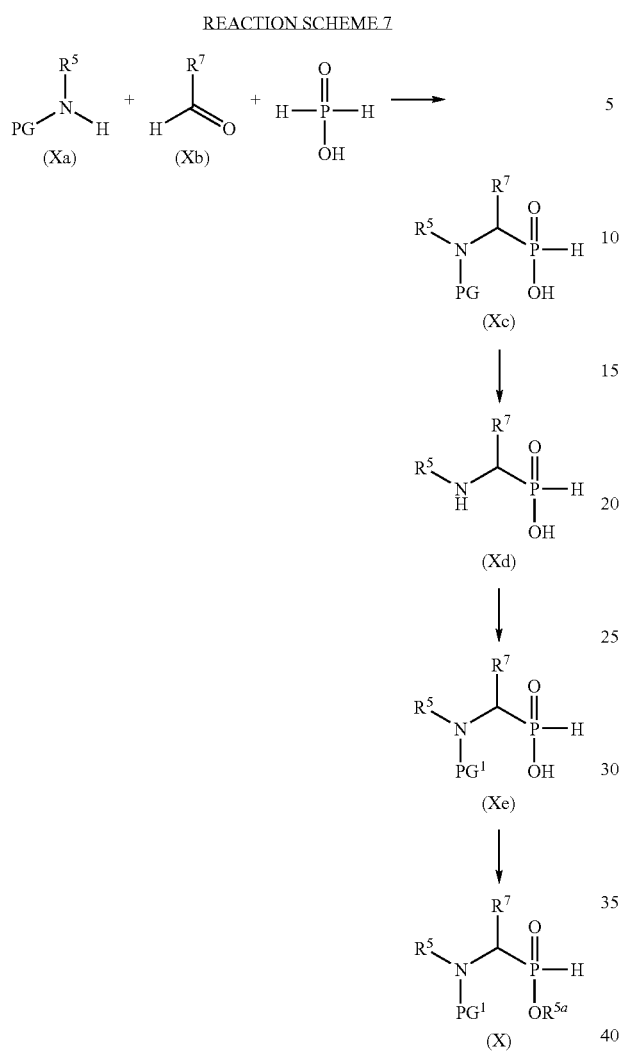

Compounds of formula (Xa), formula (Xb) and $H_3PO_2$ are commercially available, for example from Aldrich Chemical Co.

In general, in a manner similar to the methods described in Hamilton, R. et al., *Tetrahedron Lett.* (1995), pp. 4451-4454 and Baylis, E. K. et al., *J. Chem Soc, Perkin Trans,* 1 (1984), pp. 2845-2853, compounds of formula (X) are prepared by first treating a compound of formula (Xa) to a solution of hypophosphorus acid in a protic solvent, such as ethanol, at ambient temperature. The resulting reaction mixture is diluted with a polar aprotic solvent, such as ether, and the resulting precipitated salt is collected by filtration. The salt is dissolved in a polar aprotic solvent and treated with a compound of formula (Xb). The resulting reaction mixture is heated at reflux temperature for a period of about 2 hours to about 4 hours, preferably for about 3 hours. The compound of formula (Xc) is isolated from the reaction mixture by standard isolation techniques, such as salt formation, filtration and organic extraction.

The compound of formula (Xc) is then treated with a strong acid, preferably hydrobromic acid, at temperatures of between 90° C. and 110° C., preferably at a temperature of about 100° C. for a period of about 1 hour to about 3 hours, preferably for a period of about 2 hours. The compound of formula (Xd) is then isolated from the reaction mixture by standard isolation techniques.

The compound of formula (Xd) is then protected under standard nitrogen-protecting conditions to form a compound of formula (Xe), which is then treated with an appropriately substituted alcohol of formula $HOR^{5a}$ under standard esterification conditions to form a compound of formula (X), which is isolated from the reaction mixture by standard isolation techniques.

8. Preparation of Compounds of Formula (Z)

Compounds of formula (Z) are intermediates used in the preparation of compounds of formula (Im) as described above. They are commercially available or may be prepared as described below in Reaction Scheme 8 wherein $R^9$ is as described above in the Summary of the Invention and Ms is mesyl:

REACTION SCHEME 8

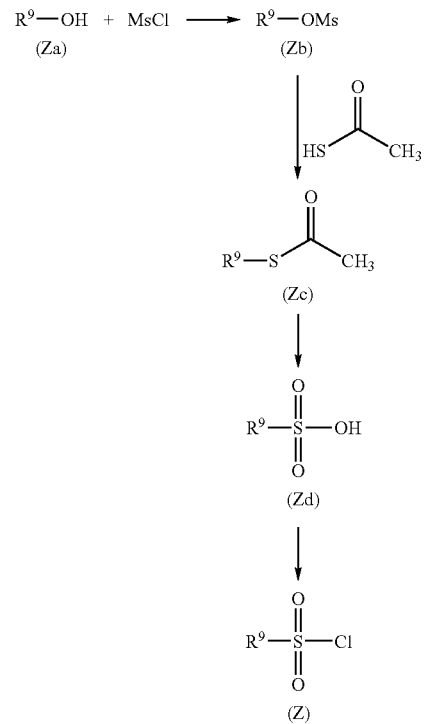

Compounds of formula (Za) and thioacetic acid are commercially available, or may be prepared according to methods known to one of ordinary skill in the art.

In general, compounds of formula (Z) are prepared by first treating a compound of formula (Za) in an aprotic solvent, such as methylene chloride, with an equimolar amount of methanesulfonyl chloride in the presence of a base, such as diisopropylethylamine, at a temperature of between about −30° C. and about 80° C., preferably at about ambient temperature, while stirring continuously for a period of about 2 hours to about 6 hours, preferably for about 4 hours, to form a compound of formula (Zb), which is isolated from the reaction mixture by standard isolation techniques, such as organic extraction and evaporation of solvents.

Thioacetic acid is added to a suspension of a strong base, such as cesium carbonate, in an aprotic solvent, such as dimethylformamide. A solution of the compound of formula (Zb) in an aprotic solvent, such as dimethylformamide, is added to the suspension. The resulting reaction mixture is stirred continuously for a period of about 12 hours to about 18 hours, preferably for about 18 hours. The compound of formula (Zc)

is isolated from the reaction mixture by standard isolation techniques, such as extraction with organic solvents, concentration and purification by column chromatography.

The compound of formula (Zc) is then oxidized under standard acid oxidation conditions to form a compound of formula (Zd), which is isolated from the reaction mixture by standard isolation techniques, such as filtration and evaporation of solvents.

The compound of formula (Zd) in an aprotic solvent, such as a mixture of methylene chloride and dimethylformamide, is cooled to a temperature of between about −5° C. and about 5° C., preferably to about 0° C., and then treated with an excess molar amount of an acyl halide reagent, such as oxalyl chloride. The resulting reaction mixture is stirred at ambient temperature for a period of about 2 hours to about 4 hours, preferably for about 3 hours. The compound of formula (Z) is then isolated from the reaction mixture by standard isolation techniques, such as evaporation and purification by silica gel chromatography.

9. Preparation of Compounds of Formula (IIb), Formula (IIc) and Formula (IId)

Compounds of formula (IIb), formula (IIc) and formula (IId) are compounds of formula (II) as described above in the Summary of the Invention. They are prepared as described below in Reaction Scheme 9 wherein $R^5$, $R^7$ and $R^9$ are as described above in the Summary of the Invention; $R^{4a}$ is as described above in the Summary of the Invention for $R^4$ except that reactive functional groups may be protected by suitable protecting groups; $R^{6a}$ is alkyl, alkenyl, alkynyl, aryl, aralkyl or aralkenyl; $PG^1$ is a suitable nitrogen protecting group; and X is halo, preferably chloro:

REACTION SCHEME 9

1.

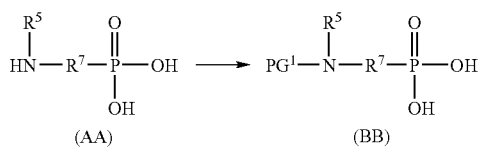

2.

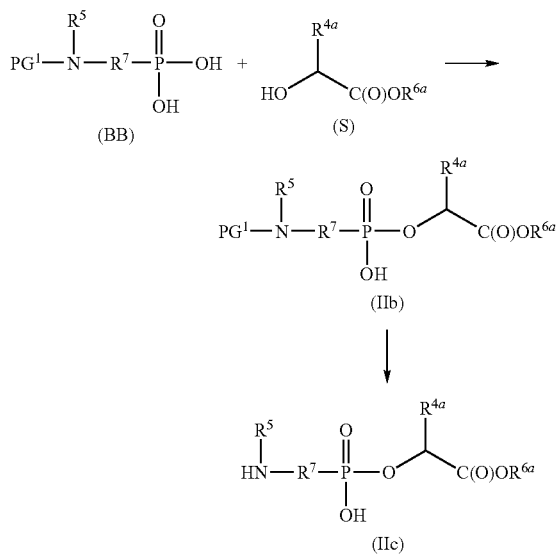

3.

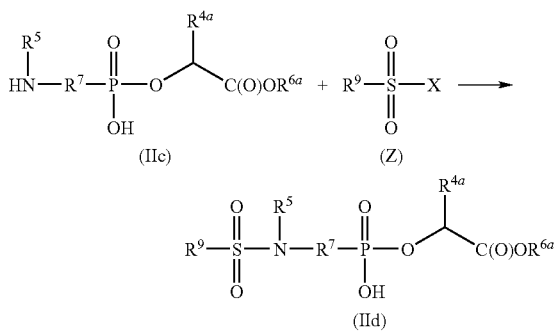

Compounds of formula (AA) are commercially available or may be prepared according to methods known to one skilled in the art. Compounds of formula (S) may be prepared according to methods known to one skilled in the art or by methods disclosed herein. Compounds of formula (Z) are prepared as described above.

In general, compounds of formula (IIb), formula (IIc) and formula (IId) are prepared by first protecting a compound of formula (AA) in a manner similar to the method described in Bartlett, P. A. et al., *J. Org. Chem.* (1990), Vol. 55, p. 6288, to produce a compound of formula (BB), which is isolated from the reaction mixture by standard isolation techniques.

The compound of formula (BB) in an aprotic solvent, such as dimethylformamide, at a temperature of about −20° C. is then treated with an acid halide reagent, such as thionyl chloride, at temperatures of between about −10° C. and about 0° C., preferably at about −5° C. The resulting reaction mixture is stirred for a period of about 30 minutes to 1 hour, preferably for about 40 minutes. A compound of formula (S) in an aprotic solvent, such as dimethyl formamide, is then added to the reaction mixture and the resulting reaction mixture is allowed to warm to ambient temperature and stirred for a period of about 1 to about 3 days, preferably for about 3 days. The reaction mixture is then basified by the addition of a base, preferably sodium bicarbonate, and the compound of formula (IIb) is then isolated from the reaction mixture by standard isolation techniques, such as organic extraction, evaporation and purification by flash chromatography.

The compound of formula (IIb) is then deprotected by standard nitrogen deprotection procedures to form a compound of formula (IIc).

To a solution of the compound of formula (IIc) in an aprotic solvent, such as methylene chloride, in the presence of a base, such as diisopropylethylamine, at temperature of between about −20° C. and about 50° C., preferably at about 0° C., is then added a compound of formula (Z) in an aprotic solvent, preferably methylene chloride. The resulting mixture is stirred at ambient temperature for a period of about 30 minutes to about 1 hour, preferably for about 30 minutes. The compound of formula (IId) is then isolated from the reaction mixture by standard isolation techniques, such as concentration and purification by silica gel chromatography.

The compound of formula (IId) may be further hydrolyzed under standard acid hydrolysis conditions to form the corresponding compound of formula (IId) where $R^{6a}$ is hydrogen.

The compounds of formula (I), (II) and (III) as set forth above in the Summary of the Invention where $R^1$ is alkyl, alkenyl, aralkyl or aralkenyl may be prepared by reacting compounds of formula (Ia), (Ib), (Ic), (Id), (Id), (Ie), (If), (Ig), (Ih), (Ii) and (Ij) with the appropriate alkyl halide, alkenyl halide, aralkyl halide or aralkenyl halide in the presence of a strong base, such as sodium methoxide or lithium diisopropylamine.

All compounds of the invention as prepared above which exist in free base or acid form may be converted to their pharmaceutically acceptable salts by treatment with the appropriate inorganic or organic base or acid. Salts of the compounds prepared above may be converted to their free base or acid form by standard techniques. It is understood that all polymorphs, amorphous forms, anhydrates, hydrates, solvates and salts of the compounds of the invention are intended to be within the scope of the invention.

In the following Preparations and Examples, the following abbreviations and acronyms may be used:
DIEA for diisopropylethylamine; DMF for dimethylformamide; THF for tetrahydrofuran; TFA for trifluoroacetic acid; DMAP for dimethylaminopyridine; AIBN for 2,2'-azobisisobutyronitrile; $CH_3CN$ for acetonitrile; $CH_2Cl_2$ for dichloromethane (methylene chloride); $CHCl_3$ for chloroform; DMSO for dimethyl sulfoxide; $Et_2O$ for diethyl ether; EDC or EDCI for 1-(3-dimethylaminopropyl)-3-ethylcarbodiimide hydrochloride; MeOH for methanol; $Bu_3SnCl$ for tributyltin chloride; $ISnBu_3$ for tributyltin iodide; BSA for bovine serum albumin; HEPES for 4-(2-hydroxyethyl)-1-piperazineethanesulfonic acid; GEMSA for guanidinoethyl-mercaptosuccinic acid; TMSCI for chlorotrimethylsilane; TMSBr for bromotrimethylsilane; NaOH for sodium hydroxide; and HCl for hydrogen chloride.

The following specific Preparations (which are directed primarily to intermediates) and Examples (which are directed primarily to claimed compounds, pharmaceutical compositions and methods of use) are provided as a guide to assist in the practice of the invention, and are not intended as a limitation on the scope of the invention.

Preparation 1

Compounds of Formula (B)

A. A solution of 2-(4-(benzyloxycarbonylamino)phenyl) ethanoic acid ethyl ester (6.5 g, 23.3 mmol), paraformaldehyde (1.05 g), potassium carbonate (5.15 g, 37.3 mmol) and tetrabutylammonium iodide (0.172 g, 0.5 mmol) in 230 mL of toluene was heated at 100° C. for 4 hours with stirring. The reaction mixture was filtered and the filtrate was washed with water, 1 M sodium hydrogen sulfate, and brine. The organic layer was evaporated in vacuo to afford 5.2 g of crude product. The product was purified by flash chromatography through silica gel (5/1 hexanes/ethyl acetate) to afford 2-(4-(benzyloxycarbonylamino)phenyl)prop-2-enoic acid ethyl ester 3.04 g (45%) as a white solid.

B. In a similar manner, compounds similar to compounds of formula (B) are prepared.

Preparation 2

Compounds of Formula (D)

A. A solution of 2-(4-(benzyloxycarbonylamino)phenyl) prop-2-enoic acid ethyl ester (2.2 g, 7.55 mmol) and thioacetic acid (5 mL) in 10 mL of chloroform was heated for 18 hours. The reaction mixture was evaporated in vacuo and purified by flash chromatography through silica gel (5/1 hexanes/ethyl acetate) to afford 2-(4-(benzyloxycarbonylamino) phenyl)-3-(acetylthio)propanoic acid ethyl ester, 0.22 g (8%) as an oil.

B. In a similar manner, compounds similar to compounds of formula (D) are prepared.

Preparation 3

Compounds of Formula (F)

A. To a solution of 2-(4-aminophenyl)-3-(acetylthio)propanoic acid ethyl ester (0.12 g, 0.45 mmol) in 4 mL of chloroform at ambient temperature was added DIEA (86 µL, 0.5 mmol) followed by N,N'-di(benzyloxycarbonyl)-N''-trifluoromethyl-sulfonylguanidine (0.175 g, 0.45 mmol). The reaction mixture was stirred for 18 hours, diluted with methylene chloride and washed with saturated sodium bicarbonate and 1 M sodium bisulfate. The organic layers were concentrated in vacuo and the resulting oil was purified by flash chromatography through silica gel (5/1 hexanes/ethyl acetate) to afford 2-(4-(N'-benzyloxycarbonyl-N''-trifluoromethyl-sulfonylguanidino)phenyl)-3-(acetylthio)propanoic acid ethyl ester (0.011 g, 52%).

B. In a similar manner, compounds similar to compounds of formula (F) are prepared.

Preparation 4

Compounds of Formula (H)

A. A slurry of 2-(pyridin-4-yl)ethanoic acid ethyl ester (10 g, 60.5 mmol) and platinum oxide (250 mg) in 100 mL acetic acid was shaken under 50 psi hydrogen gas for 18 hours. The reaction mixture was filtered and evaporated in vacuo. The resulting oil was dissolved in water and was adjusted to pH 8 with sodium bicarbonate and diluted with tetrahydrofuran. Di-t-butyl dicarbonate (13.2 g, 60.5 mmol) was added and the reaction mixture was stirred for 18 hours. The reaction mixture was concentrated in vacuo to an aqueous solution and extracted with ethyl acetate. The combined organic layers were washed with 1 M sodium bisulphate, dried and concentrated in vacuo to afford 10 g of 2-(1-benzyloxycarbonylpiperidin-4-yl)ethanoic acid ethyl ester.

B. In a similar manner, compounds similar to compounds of formula (H) are prepared.

Preparation 5

Compounds of Formula (J)

A. To a solution of lithium diisopropylamide (20 mmol) in 150 mL of THF at −78° C. was added 2-(1-benzyloxycarbonylpiperidin-4-yl)ethanoic acid ethyl ester (5.0 g, 18.4 mmol). The reaction mixture was warmed to 0° C. over 1.5 hours, then formaldehyde gas (approx. 8 g) was passed through the reaction solution for 0.5 hours. After 0.5 hours, the reaction was quenched with 10% HCl and the volatile organics were evaporated in vacuo. Purification through silica gel (5:1 hexanes/ethyl acetate) afforded pure 2-(1-benzyloxycarbonylpiperidin-4-yl)prop-2-enoic acid ethyl ester (0.40 g, 8%).

B. In a similar manner, compounds similar to compounds of formula (J) are prepared.

Preparation 6

Compounds of Formula (K)

A. To a solution of 2-(1-benzyloxycarbonylpiperidin-4-yl) prop-2-enoic acid ethyl ester (0.40 g, 1.4 mmol) in 1 mL of dioxane was added 5 mL of 6 N HCl. The solution was heated to 100° C. for 18 hours. The reaction mixture was evaporated in vacuo to afford 2-(piperidin-4-yl)prop-2-enoic acid (0.25 g, 100%) as a hydrogen chloride salt.

B. In a similar manner, compounds similar to compounds of formula (K) are prepared.

Preparation 7

Compounds of Formula (N)

A. A solution of sodium hypophosphite hydrate (17.6 g, 200 mmol), 4-phenyl-1-butene (10 mL, 66.6 mmol), 2,2'-azobisisobutyronitrile (AIBN) (1 g), conc. sulfuric acid (1 mL) in 200 mL of absolute ethanol was heated to reflux for 17 hours. The reaction mixture was concentrated to an oil, suspended in 70 mL of water, made basic with 50% NaOH and washed with 2×70 mL ether. The aqueous layer was acidified with conc. sulfuric acid, extracted into ethyl acetate and concentrated. The residue was dissolved in ether and adamantaneamine (10 g, 66 mmol) was added. A white precipitate was filtered, partitioned between 10% HCl and ethyl acetate. The organic layer was concentrated to provide 4-phenylbutylphosphinic acid (7.2 g).

B. In a similar manner, other compounds of formula (N) are prepared.

Preparation 8

Compounds of Formula (Q) and Formula (S)

A. A mixture of m-nitrobenzaldehyde (27.0 g, 178.7 mmol) and a 10% solution of 24 g of sodium bisulfite was placed in a 2 liter flask and 75 mL of ether was added. The resulting mixture was cooled in an ice-bath to 10° C. and potassium cyanide (15.0 g, 230.3 mmol) in a 20% solution was added over a period of 30 minutes. The mixture was stirred for another 30 minutes after the addition of the potassium cyanide. The ether layer was separated and the aqueous layer was extracted with ether. The combined organic layers were dried over sodium sulfate and concentrated in vacuo to afford 27.81 g (87%) of α-hydroxy-3-nitrobenzeneacetonitrile, a compound of formula (Q), as a pale yellow oil.

B. To a solution of α-hydroxy-3-nitrobenzeneacetonitrile (27.8 g, 156.1 mmol) in 500 mL of ether was added methanol (7.6 mL, 187.3 mmol). Hydrogen chloride gas was bubbled into the solution until it was saturated. The solution changed to a heterogeneous solution. The solution was cooled to 0° C. and filtered to collect the solid. The filtrate was extracted with methylene chloride, dried over sodium sulfate, filtered and concentrated to afford 25.0 g (76%) of 2-hydroxy-2-(3-nitrophenyl)ethanoic acid methyl ester, a compound of formula (S), as a yellow solid.

C. To a solution of 2-hydroxy-2-(3-nitrophenyl)ethanoic acid methyl ester (11.52 g, 54.55 mmol) in 200 mL of MeOH was added 950 mg of 10% Pd/C followed by di-t-butyl dicarbonate (13.2 g, 60.5 mmol) as a solution in 50 mL of methanol. An atmosphere of $H_2$ was applied at 30 psi and the reaction was shaken for 7 hrs. The resulting yellow solution was filtered through a pad of celite and concentrated in vacuo. Purification by $SiO_2$ flash column chromatography (30% ethyl acetate/hexanes) provided 12.9 g (84%) of 2-hydroxy-2-(3-(t-butoxycarbonylamino)phenyl)ethanoic acid methyl ester as a yellow oil.

D. To a solution of 2-(3-nitro)phenyl-2-hydroxyethanoic acid methyl ester (5.57 g, 26.4 mmol) in 250 mL of methanol was added N',N''-di(t-butoxycarbonyl)-1H-pyrazole-1-carboxamidine (8.15 g, 26.2 mmol). To the reaction mixture was added 10% Pd/C (325 mg) in methanol (10 mL). After hydrogenation under at 30 psi hydrogen gas for 4.5 hours, the reaction mixture was filtered through a pad of celite and concentrated in vacuo. Purification by $SiO_2$ flash column chromatography (gradient 10-100% ethyl acetate/hexanes) provided 9.07 g (81%) of 2-(3-(N',N''-di(t-butoxycarbonyl)guanidino)phenyl)-2-hydroxyethanoic acid methyl ester as a white solid.

E. In a similar manner, other compounds of formula (Q) and formula (S) are prepared.

Preparation 9

Compounds of the Invention where $R^3$ is Tetrazole

A. A mixture of a 10% solution of sodium bisulfite (24 g, 230 mmol) and 3-nitrobenzaldehyde (27 g, 178 mmol) was combined in a 1 L flask with 75 mL ether and 100 ml THF. The resulting reaction mixture was cooled in an ice-water bath to 10° C. and a solution of potassium cyanide (15 g, 130 mmol) in 75 mL water was added over a period of a half-hour while stirring. The reaction mixture was stirred at 15° C. for 1 hour. The organic layers were separated and the aqueous phase was extracted with ether (200 mL). The combined organic layers were dried over sodium sulfate and concentrated in vacuo to afford (3-nitrophenyl)(hydroxy)acetonitrile as a yellow oil (29 g, 163 mmol), which was used without further purification in the next step.

B. To a solution of (3-nitrophenyl)(hydroxy)acetonitrile (3.5 g, 19.6 mmol) in 100 mL toluene was added sodium azide (8 g, 123 mmol) and $Bu_3SnCl$ (26 ml, 98 mmol). The mixture solution was heated at reflux for 10 hours. The solvent was removed in vacuo, the residue was dissolved in water, acidified with 1N HCl, and extracted with 3×100 mL ethyl acetate. The crude product was purified by flash chromatography on silica gel to afford 5-(3-nitrophenyl)(hydroxy)methyltetrazole (2.0 g, 9 mmol, 46%) as yellow solid. To a solution of 5-(3-nitrophenyl)(hydroxy)-methyltetrazole (1.3 g, 5.9 mmol) in 50 mL methanol was added $SnCl_2$ (8 g, 35.4 mmol). The resulting reaction mixture was heated at 60° C. for 20 minutes. The reaction mixture was dried in vacuo, then purified directly over an ion-exchange column to afford 5-(3-aminophenyl)(hydroxy)methyltetrazole (1.0 g, 5.2 mmol, 88%), which was used directly in the next step.

C. To a solution of 5-(3-aminophenyl)(hydroxy)methyltetrazole (1.0 g, 5.2 mmol) in 30 mL acetonitrile was added N,N'-di(t-butoxycarbonyl)guanidinopyrazole (1.6 g, 5.2 mmol) and DIEA (1.8 mL, 10.4 mmol). The resulting reaction mixture was heated at 55° C. for 18 hours. The reaction mixture was concentrated in vacuo, the residue was taken up into 200 mL ethyl acetate, then washed with 1N $NaHSO_4$ and water. The crude mixture was purified with flash column on silica gel to afford 5-(3-N,N'-di(t-butoxycarbonyl)guanidinophenyl)-(hydroxy)methyltetrazole (0.9 g, 2.0 mmol, 40%).

Preparation 10

Compounds of Formula (V)

A. In a flame dried 2 L three-necked round bottom flask, 40.0 g (476 mmol) of propynoic acid methyl ester was dissolved in 1 L of THF and cooled in an ice bath. To the stirred solution, 10.0 g (8.65 mmol) tetrakis(triphenylphosphine) palladium was added. To the resulting mixture, 210 mL (682 mmol) of tributyltin hydride was added dropwise using an addition funnel over 40-60 minutes. The mixture was allowed to stir overnight at ambient temperature. The mixture was concentrated in vacuo and loaded directly onto a silica column (hexane). Hexanes was used as the eluent until the tin byproduct (ISnBu$_3$) was removed. A 3:1 (hexane:methylene chloride) solution was then used for elution of desired product. Fractions were combined and concentrated to yield 140 g (78%) of 2-tributyltinpropenoic acid methyl ester, NMR (DMSO-d$_6$) 0.82-0.86 (dd, J=7.3, 9), 0.93-0.97 (m, 6), 1.21-1.30 (m, 6), 1.42-1.50 (m, 6), 3.31 (s, 3), 5.96-5.97 (d, J=2.6 Hz, 1), 6.77-6.78 (d, J=2.6 Hz, 1) ppm.

B. In a similar manner, other compounds of formula (V) are prepared.

Preparation 11

Compounds of Formula (W)

A. In a flame dried flask, 31.27 g (94 mmol) of 3-iodo-(t-butoxy-carbonylamino)methylbenzene was dissolved in DMF (500 mL) and the solution was stirred. To this stirring solution 70.2 g (187 mmol) of 2-tributyltinpropenoic acid methyl ester, 21.6 g (18.7 mmol) of tetrakis(triphenylphosphine) palladium (obtained from Strem) and 14.2 g (74.6 mmol) of copper iodide were sequentially added. The resulting reaction mixture was allowed to stir at ambient overnight. The reaction mixture was diluted with 1 L Et$_2$O in a separator funnel and partitioned with 500 mL H$_2$O. The resulting biphasic mixture was filtered to remove precipitates and extraction continued with water (4×500 mL) to remove DMF (~2.5 L of water in total). The organic layer was dried (Na$_2$SO$_4$) and concentrated to result in a dark syrup which was redissolved in 5% ethyl acetate in hexane and loaded directly onto a silica column (hexane). Elution with 5% ethyl acetate in hexane was performed until all tin species (ISnBu$_3$ and remaining 2-tributyltinpropenoic acid methyl ester) was removed. Elution with 10% ethyl acetate in hexane allowed for isolation of desired material. Fractions were combined and concentrated to afford 23.8 g (87%, 81.7 mmol) of isolated 2-(3-(t-butoxycarbonylamino)methylphenyl)propenoic acid methyl ester as a yellow syrup, which was found to be pure (≧95%) by HPLC and NMR; NMR (DMSO-d$_6$: δ1.38 (S, 9), 3.74 (2, 3), 4.12 (d, J=6.22 Hz, 2), 5.96 (d, J=1.1 Hz, 1), 6.22 (d, J=1.0 Hz, 1), 7.20-7.40 (m, 4) ppm.

B. In a similar manner, other compounds of formula (W) are prepared.

Preparation 12

Compounds of Formula (X)

A. Diphenylmethylamine (34 mL, 0.2 mol) was added dropwise to a solution of 100% hypophosphorous acid (13.2 g, 0.2 mol) in 100 mL of absolute ethanol. The resulting mixture was stirred at ambient temperature for 15 minutes, then diluted with 500 mL of ether. The precipitated salt (45 g) was collected by filtration. The salt (25 g, 0.1 mol) was dissolved in 50 mL of absolute ethanol and the isopropanal (9 mL, 0.1 mol) (a compound of formula (Xb)) was added. The reaction mixture was heated at reflux for 3 hours. On cooling, the product formed as a precipitate. The product was removed by filtration and washed with ethanol and ether to afford 1-(diphenylmethylamino)-2-methylpropylphosphonous acid (a compound of formula (Xc)) as a white solid (12.5 g) that was used in the next step without further purification.

B. 1-(diphenylmethylamino)-2-methylpropylphosphonous acid (12 g) was suspended in 100 mL of 48% hydrobromic acid, then heated at 100° C. for 2 hours until two distinct phases separated. The mixture was evaporated to dryness in vacuo, and the residue taken up in 100 mL of water. The aqueous solution was washed several times with ether to remove diphenylmethyl bromide and then evaporated to give an 80 mL solution of 1-amino-2-methylpropylphosphonous acid, a compound of formula (Xd). The solution of 1-amino-2-methylpropylphosphonous acid in 80 ml water was adjusted to pH 9.5 using 4 N NaOH, and the solution was cooled to 0° C. by an ice bath. Benzyl chloroformate (7.1 mL, 47 mmol) was added dropwise over 30 minutes and the resulting mixture was stirred for an additional 12 hours while the pH was maintained at pH 9-9.5 by periodic addition of 4 N NaOH. The reaction mixture was washed with ether (3×100 mL) to remove excess benzyl chloroformate. The aqueous solution was acidified using concentrated HCl to pH 1, then extracted by ethyl acetate (4×100 mL). The organic phase was dried over Na$_2$SO$_4$ and concentrated to afford 9.2 g of 1-(benzyloxycarbonylamino)-2-methylpropylphosphonous acid, as a white solid, which could be used in further reactions without further purification.

C. A solution of 1-(benzyloxycarbonylamino)-2-methylpropylphosphonous acid (3.4 g, 12.5 mmol) in 20 mL of absolute ethanol was heated to reflux and (R)-(+)-methylbenzylamine (96% ee, 1.5 g, 12.5 mmol) was added. The resulting mixture was diluted with 120 mL of ethyl acetate. The precipitate was filtered off, washed with 100 mL of ethyl acetate and 100 mL of ether, dried in vacuo to afford (R)-1-(benzyloxycarbonylamino)-2-methylpropylphosphonous acid as a white solid (1.1 g) with a rotation $[\alpha]_D$=−10.87° (c=10 mg/mL 9:1 DMF-H$_2$O). This material was found to be 93% ee by chiral HPLC.

D. (R)-1-(benzyloxycarbonylamino)-2-methylpropylphosphonous acid (1.1 g, 2.8 mmol) was suspended in 20 mL water, basified to pH>10 by 4 N NaOH, and extracted by ether (3×50 mL) to remove (R)-(+)-methylbenzylamine. The aqueous solution was acidified to pH 1 with concentrated HCl and extracted with ethyl acetate (4×50 mL). The organic phase was dried and concentrated to afford (R)-1-(benzyloxycarbonylamino)-2-methylpropylphosphonous acid as a white solid (0.7 g), $^1$H NMR DMSO-d$_6$ 0.85 (3, d), 0.95 (3, d), 2.03 (1, m), 3.43 (m, 1), 5.03 (2, s), 6.14 (0.5, s), 7.32 (5, m), 7.46 (0.5, s), 7.58 (1, d) ppm.

E. To a solution of 1-(benzyloxycarbonylamino)-2-methylpropylphosphonous acid (5.8 g, 21.4 mmol) in 15 mL ethanol and 200 mL CH$_2$Cl$_2$ was added EDC (5.0 g, 26 mmol). The resulting reaction mixture was stirred at ambient temperature for 30 minutes. The mixture was concentrated in vacuo, and the residue was taken up into 200 mL ethyl acetate, washed with water and brine. The solvent was evaporated in vacuo to afford 1-(benzyloxycarbonylamino)-2-methylpropylphosphonous acid ethyl ester (6.2 g, 20.7 mmol, 96.8%) as white solid which was used without further purification.

F. In a similar manner, other compounds of formula (X) are prepared.

Preparation 13

Compounds of Formula (Z)

A. To a solution of 3-phenylpropylalcohol (52.5 g, 386 mmol) in 1 L methylene chloride was added diisopropylethylamine (134 mL, 772 mmol). After cooling to 0° C., methanesulfonyl chloride (29.73 g, 386 mmol) was added dropwise. The reaction mixture was stirred continuously for 4 hours at ambient temperature. The reaction mixture was washed with 1 M NaHSO$_4$, H$_2$O, and brine. After drying (Na$_2$SO$_4$), and evaporating the solvent in vacuo, the resulting yellow syrup (75 g, 96%) was carried to next step without further purification, NMR (CDCl$_3$) 2.15 (q, 2), 2.75 (t, 2), 3.00 (s, 3), 4.24 (t, 2), 7.18 (m, 3) 7.24 (m, 2) ppm.

B. Thioacetic acid (27 mL, 378 mmol) was added to a suspension of Cs$_2$CO$_3$ in DMF (1.5 L). A solution of the mesylate prepared above (67.6 g, 315 mmol) in DMF (100 mL) was added in one portion to the suspension and the reaction mixture was stirred continuously at ambient temperature for 18 hours during which the reaction flask was covered with aluminum foil. The mixture was poured into water (4 L), and extracted with ethyl acetate (5×700 mL). The combined organic layers were washed with water, NaHCO$_3$ (5%, 1 L), and brine. Drying (Na$_2$SO$_4$) followed by concentration in vacuo afforded the crude product, which was purified by column chromatography (CH$_2$Cl$_2$) to afford an oil (55 g, 89%), NMR (CDCl$_3$) 1.92 (q, 2), 2.35 (s, 3), 2.72 (t, 2), 2.88 (t, 2), 7.18 (m, 3), 7.24 (m, 2) ppm.

C. A mixture of H$_2$O$_2$ (30% in H2O (320 mL)) and acetic acid (160 mL) was added to a solution of the thioacetate prepared above (55 g, 283 mmol) in 320 mL of acetic acid. After stirring overnight at ambient temperature, 10% Pd/C (2 g) was added to destroy excess of peroxide. Filtration over celite and evaporation of solvents afforded the crude sulfonic acid (66 g), which was carried to next step without purification, NMR (CDCl$_3$) 2.12 (q, 2), 2.72 (t, 2), 3.08 (t, 2), 7.12 (m, 3), 7.24 (m, 2) ppm.

D. To a solution of the sulfonic acid prepared above (66 g, 330 mmol) in 1.2 L of methylene chloride and 25 mL of DMF cooled to 0° C. was added oxalyl chloride (57 mL, 660 mmol) dropwise over a period of 1 hour. The reaction mixture was stirred at ambient temperature for 3 hours. Solvent was evaporated in vacuo and a gravity column on silica gel eluting with methylene chloride afforded a light yellow oil, 3-phenylpropylsulfonyl chloride (57 g, 81%), NMR (CDCl$_3$) 2.38 (q, 2), 2.84 (t, 2), 3.62 (t, 2), 7.18 (m, 2) 7.24 (m, 1) 7.36 (m, 2) ppm.

E. In a similar manner, other compounds of formula (Z) are prepared.

Preparation 14

Compounds of Formula (BB)

A. A slurry of (1R)-(+)-(1-amino-2-methylpropyl)phosphonic acid (2.57 g, 16.8 mmol), NaHCO$_3$ (2.82 g, 33.6 mmol), and Na$_2$CO$_3$ (3.58 g, 33.8 mmol) in 16 mL of 2N NaOH and 3 mL of H$_2$O was cooled in an ice water bath. To this was added benzyloxycarbonyl chloride (2.4 mL, 16.8 mmol). During the next 2 hours, two additional aliquots of benzyloxycarbonyl chloride were added (2.4 mL each). After stirring at ambient temperature for 16 hours, 40 mL of 2N NaOH was added and the mixture was partitioned between water and ether. The aqueous portion was washed with ether, acidified to pH 2 with concentrated HCl, and extracted with ethyl acetate (2×) and with methylene chloride (2×). The combined organic extracts were washed with saturated NaCl, dried over MgSO$_4$, filtered, and concentrated in vacuo to give 4.41 g (91%) of (1R)-(+)-(1-benzyloxycarbonylamino-2-methylpropyl)phosphonic acid as a white foam.

B. In a similar manner, other compounds of formula (BB) are prepared.

EXAMPLE 1

Compounds of Formula (Ia)

A. To a solution of 2-(4-(benzyloxycarbonylamino)phenyl)-3-(acetylthio)-propanoic acid ethyl ester (0.2 g, 0.54 mmol) in 5 mL of methylene chloride was added 5 mL of trifluoroacetic acid. After 0.5 hours, the reaction mixture was concentrated in vacuo. The compound was purified by flash chromatography through silica gel (1/1 hexanes/ethyl acetate) to afford 2-(4-aminophenyl)-3-(acetylthio)propanoic acid ethyl ester (0.12 g, 85%).

B. In a similar manner, but after base hydrolysis with ammonium hydroxide as described below in Example 3(D), the following compound was prepared:
2-(3-aminophenyl)-3-mercaptopropanoic acid, NMR (DMSO-d$_6$) 2.32 (t, 1), 2.70 (m, 1), 2.96 (m, 1), 3.63 (m, 1) 6.95 (overlapping peaks, 3) 7.25 (t, 1) ppm.

EXAMPLE 2

Compounds of Formula (Ib) and (Ic)

A. Hydrogen chloride gas was bubbled through a solution of 2-(4-(N'-benzyloxycarbonyl-N''-trifluoromethylsulfonylguanidino)-phenyl)-3-(acetylthio)propanoic acid ethyl ester in degassed ethanol at 0° C. for 5 minutes. The reaction mixture was warmed to ambient temperature and stirred for 18 hours. The reaction mixture was concentrated in vacuo to afford 2-(4-guanidinophenyl)-3-mercaptopropanoic acid ethyl ester as an oil and was used without further purification in the next step.

B. To a solution of 2-(4-guanidinophenyl)-3-mercaptopropanoic acid ethyl ester (60 mg) in 1:1:1 water/ethanol/tetrahydrofuran at 0° C. was added LiOH (130 mg). The reaction was stirred for 18 hours, acidified to pH 2 with trifluoroacetic acid and purified by preparative HPLC to afford 2-(4-guanidinophenyl)-3-mercaptopropanoic acid, as a trifluoroacetic acid salt, (15 mg); NMR (D$_2$O) 2.75-2.83 (dd, 1), 2.98-3.05 (dd, 1), 3.75-3.80 (dd, 1), 7.19 (d, 2), 7.32 (d, 2) ppm.

C. In a similar manner, the following compounds similar to the compounds of formula (Ib) and (Ic) as prepared above were prepared:
2-(3-guanidinophenyl)-3-mercaptopropanoic acid, trifluoroacetic acid salt, NMR (D$_2$O) 3.24 (m, 2), 4.12 (t, 1), 7.60 (m, 4) ppm;
2-(3-guanidinophenyl)-3-mercaptopropanoic acid, NMR (DMSO-d$_6$) 2.80 (m, 1), 3.08 (m, 1), 3.88 (t, 1), 7.22 (m, 2), 7.28 (m, 1), 7.42 (m, 1), 8.18 (s, 1) ppm;
(−)-2-(3-guanidinophenyl)-3-mercaptopropanoic acid, NMR (D$_2$O) 2.95 (m, 1), 3.19 (m, 1), 3.90 (t, 1), 7.25 (d, 2), 7.40 (d, 1), 7.51 (t, 1) ppm;
(+)-2-(3-guanidinophenyl)-3-mercaptopropanoic acid, NMR (D$_2$O) 2.98 (m, 1), 3.20 (m, 1), 3.95 (t, 1), 7.30 (d, 2), 7.40 (d, 1), 7.55 (t, 1) ppm; and
2-(2-chloro-5-guanidinophenyl)-3-mercaptopropanoic acid; NMR (D$_2$O) 2.95 (m, 1), 3.15 (m, 1), 4.05 (t, 1), 7.21 (1, d), 7.35 (s, 1), 7.60 (d, 1) ppm.

EXAMPLE 3

Compounds of Formula (Id) and (Ie)

A. A solution of 2-(piperidin-4-yl)prop-2-enoic acid (0.30 g, 1.64 mmol) in 6 mL of 1:1 thioacetic acid/isopropanol was stirred for 24 hours. The reaction mixture was concentrated in vacuo to afford the crude product, 2-(piperidin-4-yl)-3-(acetylthio)propanoic acid. The product was dissolved in 2 mL of water, cooled to 0° C., degassed with nitrogen, and 2 mL of ammonium hydroxide was added. The reaction mixture was stirred for 1 hour, concentrated in vacuo and the residue was dissolved in 10% HCl and purified by preparative HPLC to afford 73 mg of pure 2-(piperidin-4-yl)-3-mercaptopropanoic acid, as a trifluoroacetic acid salt, NMR ($D_2O$) 1.30-1.43 (m, 2), 1.70-1.90 (m, 3), 2.32-2.42 (m, 1), 2.50-2.60 (m, 1), 2.63-2.72 (m, 1), 2.79-2.90 (m, 2), 3.22-3.34 (m, 2) ppm.

B. In a similar manner, the following compounds were prepared:

2-(piperidin-3-yl)-3-mercaptopropanoic acid, NMR (DMSO-$d_6$) 1.19 (q, 1) 1.51 (m, 1) 1.70 (dod, 2) 1.96 (m, 1) 2.33 and 2.39 (overlapping m, 2) 2.59 and 2.68 (overlapping m, 4) 3.20 (dod, 2) 8.38 (m, 1) 8.64 (m, 1) ppm, and NMR (DMSO-$d_6$) 1.19 (m, 1) 1.51 (m, 1) 1.72 (m, 2) 1.98 (m, 1) 2.32 and 2.39 (overlapping m, 2) 2.63 (m, 4) 3.17 (m, 1) 8.32 (m, 1) 8.62 (m, 1) ppm;

C. A solution of 2-(piperidin-4-yl)-3-(acetylthio)propanoic acid (0.6 g, 1.72 mmol) and Boc-glycine-N-hydroxysuccinimide ester (0.52 g, 1.9 mmol) was stirred in 15 mL of dioxane for 18 hours. The reaction mixture was concentrated, partitioned between ethyl acetate and 1 M $NaHSO_4$. The organic layer was concentrated to give 2-(1-(t-butoxycarbonylaminomethylcarbonyl)-piperidin-4-yl)-3-(acetylthio) propanoic acid, which was dissolved in 10 mL of 1:1 methylene chloride-TFA for 1 hour. The reaction mixture was then concentrated. The resulting residue was dissolved in water-methanol, cooled to 0° C. and purged with nitrogen gas. Aqueous $NH_4OH$ was added and the resulting reaction mixture was stirred for 1 hour and then concentrated to an oil. Purification by prep HPLC afforded 65 mg of 2-(1-(aminomethylcarbonyl)-piperidin-4-yl)-3-mercaptopropanoic acid; NMR ($D_2O$) 1.2-1.21 (m, 2), 1.51-1.82 (m, 3), 2.30-2.40 (m, 1), 2.48-2.71 (m, 2), 2.90-3.00 (m, 1), 3.55 (m, 1), 3.82 (m, 2), 4.21 (m, 1) ppm.

D. 2-(Piperidin-3-yl)-3-(acetylthio)propanoic acid was dissolved in trifluoroacetic acid and the reaction mixture was stirred for 2 hours. The solvent was removed in vacuo. The resulting material was dissolved in 10 mL $CHCl_3$ and 0.48 mL of N-methyl-N-(trimethylsilyl)trifluoroacetamide was added. The mixture was stirred for 30 minutes under nitrogen gas. Triethylamine (0.5 mL) and di(t-butoxycarbonyl)-guanidine triflate (0.56 mg) were added and the mixture was refluxed for 3 hours. After cooling to ambient temperature, an equal volume of TFA was added and the solution was stirred for 1 hour. The solvents were removed in vacuo (starting material still present). The mixture was dissolved in neat TFA and the mixture was stirred overnight. The crude product was purified by reverse phase HPLC to give 2-(1-amidinopiperidin-3-yl)-3-(acetylthio)propanoic acid as two partially separable diastereomers. Fractions corresponding to the first major peak were collected and found to contain 80% of diastereomer A by HPLC. The second major peak contained 58% of diastereomer B by HPLC. The diastereomers were individually dissolved in 15 mL water. $N_2$ was bubbled through the solution and 4 mL $NH_4OH$ was added. The solution was stirred for 1 hour. The solvents were removed in vacuo and the reaction mixture was purified by reverse phase HPLC to give 2-(1-amidinopiperidin-3-yl)-3-mercaptopropanoic acid, NMR ($D_2O$) 1.63 (m, 1) 1.82 (m, 1) 2.02-2.30 (overlapping m, 3) 2.82 (m, 1) 3.01 (m, 2) 3.28 (m, 2) 4.01 (m, 2) ppm.

EXAMPLE 4

Compounds of Formula (If)

A. To 4-phenylbutylphosphinic acid (357 mg, 1.8 mmol) in methylene chloride at 0° C. was added DIEA (0.66 mL, 3.8 mmol), followed by TMSCl (0.47 mL, 3.8 mmol). After 1 hour, 2-(3-(t-butoxycarbonylamino)phenyl)propenoic acid methyl ester (0.5 g, 1.8 mmol) was added and the reaction mixture was allowed to warm to ambient temperature. After 5 hours, the reaction was partitioned between methylene chloride and saturated $NaHCO_3$ solution. The organic layer was washed with 0.1 N sulfuric acid and concentrated in vacuo. The residue was dissolved in 10 mL 3:1 THF:methanol for 18 hours. The reaction was concentrated to provide 2-(3-(t-butoxycarbonylamino)phenyl)-3-((4-phenylbutyl)(hydroxy) phosphinoyl)propanoic acid methyl ester (845 mg) as a white foam.

B. 2-(3-(t-Butoxycarbonylamino)phenyl)-3-((4-phenylbutyl)(hydroxy)-phosphinoyl)propanoic acid methyl ester (845 mg, 1.8 mmol) was stirred in 1 M NaOH (5.3 mL, 5.3 mmol) in methanol/THF/$H_2O$ for 1.5 hours. The product was concentrated in vacuo. The residue was dissolved in 10 mL methylene chloride and TFA (10 mL) was added. After 45 minutes, the reaction mixture was concentrated to provide 2-(3-aminophenyl)-3-((4-phenylbutyl)(hydroxy)phosphinoyl)propanoic acid, NMR (DMSO-$d_6$) 1.30-1.45 (m, 8), 1.80 (m, 1), 2.35 (m, 1), 3.62 (m, 1), 6.58-6.65 (m, 3), 7.05 (m, 1), 7.15 (m, 3), 7.23 (m, 2) ppm; as a crude product. Pure product was obtained by preparative reversed-phase HPLC.

C. To 2-(3-aminophenyl)-3-((4-phenylbutyl)(hydroxy) phosphinoyl)-propanoic acid trifluoroacetate salt (300 mg, 0.63 mmol) in 25 mL methylene chloride was added DIEA (0.44 mL) and N-methyl-N-trimethylsilyltrifluoroacetamide (0.3 mL, 1.6 mmol) to form the silyl ester in situ. After 1.5 hours, the reaction mixture was heated at 45° C. for 1.5 hours, cooled to 0° C. and N,N'-di(t-butoxycarbonyl)-N''-trifluoromethanesulfonylguanidine (260 mg, 0.66 mmol) was added. The reaction was heated at 40° C. for 18 hours. The reaction mixture was concentrated and purified by prep HPLC to afford 2-(3-(N,N'-di(t-butoxycarbonyl)guanidino) phenyl)-3-((4-phenylbutyl)(hydroxy)phosphinoyl)propanoic acid (70 mg).

D. 2-(3-(N,N'-di(t-Butoxycarbonyl)guanidino)phenyl)-3-((4-phenylbutyl)-(hydroxy)phosphinoyl)propanoic acid was dissolved in 9 mL 2:1 methylene chloride:TFA. After 1.5 hours, the reaction mixture was concentrated and purified by prep HPLC to afford 2-(3-guanidinophenyl)-3-((4-phenylbutyl)(hydroxy)-phosphinoyl)propanoic acid, NMR (DMSO-$d_6$) 1.25-1.60 (m, 6), 2.00 (m, 1), 2.40-2.50 (m, 2), 3.85 (m, 1), 7.0-7.45 (m, 9) ppm, (2.9 mg).

E. In a similar manner, the following compounds of the invention were made:

2-(3-aminophenyl)-3-((phenyl)(hydroxy)phosphinoyl)propanoic acid, NMR (DMSO-$d_6$) 2.15 (m, 1), 2.73 (m, 1), 3.75 (m, 1), 6.92 (m, 3), 7.22 (m, 1), 7.55 (m, 2), 7.60 (m, 1), 7.73 (m, 2) ppm;

2-(3-aminophenyl)-3-((pentyl)(hydroxy)phosphinoyl)propanoic acid, NMR (DMSO-$d_6$) 0.80 (t, 3), 1.20-1.40 (m, 8), 1.82 (m, 1), 2.40 (m, 1), 3.78 (m, 1), 6.95-7.05 (m, 3), 7.25 (m, 1) ppm;

2-(3-guanidinophenyl)-3-((phenyl)(hydroxy)phosphinoyl) propanoic acid, NMR (DMSO-$d_6$) 2.42 (m, 1), 2.68 (m, 1), 3.85 (m, 1), 7.00-7.58 (m, 9) ppm;

2-(3-guanidinophenyl)-3-((pentyl)(hydroxy)phosphinoyl) propanoic acid, NMR (DMSO-$d_6$) 0.8 (m, 3), 1.15-1.6 (m, 8), 1.95 (m, 1), 2.4 (m, 1), 3.82 (m, 1), 7.0-7.5 (m, 5) ppm;

2-(3-guanidinophenyl)-3-((4-methylpentyl)(hydroxy)phosphinoyl)propanoic acid, NMR (DMSO-$d_6$) 0.80 (d, 6), 1.10 (m, 2), 1.25-1.45 (m, 6), 2.02 (m, 1), 2.45 (m, 1), 3.85 (m, 1), 7.05 (m, 1), 7.18 (m, 2), 7.35 (m, 1) ppm;

2-(3-guanidinophenyl)-3-((3-phenylpropyl)(hydroxy)phosphinoyl)propanoic acid, NMR (DMSO-$d_6$) 1.15 (m, 2), 1.25 (m, 2), 1.62 (m, 1), 2.20 (m, 2), 3.45 (m, 1), 6.70-7.00 (m, 9) ppm;

2-(3-guanidinophenyl)-3-((3-phenylprop-2-enyl)(hydroxy) phosphinoyl)propanoic acid; NMR (DMSO-$d_6$) 2.0 (m, 1), 2.41 (m, 1), 2.58 (dd, 2), 3.9 (m, 1), 6.12 (m, 1), 6.4 (dd, 1), 7.06-7.12 (dd, 1), 7.14-7.24 (m, 3), 7.24-7.4 (m, 5), 7.48 (m, 3), 9.8 (s, 1) ppm;

2-(3-guanidinophenyl)-3-((phenylmethyl)(hydroxy)phosphinoyl)propanoic acid, NMR (DMSO-$d_6$) 2.0 (m, 1), 2.45 (m, 1), 3.1 (dd, 2), 3.9 (m, 1), 7.15-7.4 (m, 6) 7.4-7.6 (m, 4) ppm;

2-(3-guanidinophenyl)-3-((pentyl)(hydroxy)phosphinoyl) propanoic acid methyl ester, NMR (DMSO-$d_6$) 0.81 (m, 3), 1.2 (m, 4), 1.4 (m, 4), 2.0 (m, 1), 2.4 (m, 1), 3.36 (s, 3), 3.89 (m, 1), 7.1 (d, 1), 7.2 (m, 2), 7.38 (t, 1), 7.45 (m, 3) ppm;

2-(3-guanidinophenyl)-3-((ethyl)(hydroxy)phosphinoyl) propanoic acid, NMR (DMSO-$d_6$) 0.9 (m, 3), 1.41 (m, 2), 1.98 (m, 1), 2.4 (m, 1), 3.82 (m, 1), 7.0-7.5 (m, 6) ppm;

2-(1-amidinopiperidin-4-yl)-3-mercaptopropanoic acid; NMR ($D_2O$) 1.15-1.23 (m, 3), 1.58-1.88 (m, 2), 2.30-2.40 (m, 1), 2.50-2.58 (m, 1), 2.67 (m, 1), 2.85-2.99 (m, 2), 2.62-2.75 (m, 2) ppm;

2-(1-(1-iminoethyl)piperidin-4-yl)-3-mercaptopropanoic acid; NMR ($D_2O$) 1.18 (m, 1), 1.20-1.35 (m, 2), 1.60-1.95 (m, 3), 2.10 (s, 3), 2.31-2.40 (m, 1), 2.55 (dd, 1), 2.63 (dd, 1), 2.90-3.11 (m, 2), 3.81 (m, 2) ppm;

2-(3-guanidinophenyl)-3-((2-phenylethyl)(hydroxy)phosphinoyl)propanoic acid, NMR (DMSO-$d_6$) 1.78 (m, 2), 2.0 (m, 1), 2.41 (m, 1), 2.7 (m, 2), 3.9 (m, 1), 7.05-7.6 (m, 11), 9.8 (s, 1) ppm; and 2-(3-guanidinophenyl)-3-((2-(methylcarbonyl)ethyl)(hydroxy)phosphinoyl)propanoic acid, NMR (DMSO-$d_6$) 1.82 (m, 2), 2.0 (m, 1), 2.2 (s, 3), 2.4 (m, 1), 2.58 (m, 2), 3.82 (m, 1), 7.0-7.6 (m, 10), 9.8 (s, 1) ppm.

F. Alternatively, phosphonic acid diethyl ester (465 µL, 3.6 mmol) was dissolved in 10 mL of methylene chloride and cooled in an ice bath. Trimethyl aluminum (2.0 M in toluene, 1.8 mL, 3.6 mmol) was added dropwise and the resulting solution was stirred for 20 minutes. 2-(3-(t-Butoxycarbonylamino)phenyl)propenoic acid ethyl ester (1.0 g, 3.43 mmol) (as prepared by methods disclosed herein) was dissolved in 5 mL of methylene chloride and added to the reaction mixture. The reaction mixture was stirred overnight at ambient temperature. The reaction mixture was poured into a separator funnel containing 50 ml of water. The resulting reaction mixtures was agitated and the layers were allowed to separate. Ice-cold 0.2N HCl and methylene chloride (20 ml of each) was added and the resulting mixture was agitated. The organic layers were separated and the aqueous layer was washed with 20 mL of methylene chloride. The resulting organic layers were combined and washed with 50 mL of water and then dried over magnesium sulfate before filtering and evaporating to produce the product as an oil, 0.9 g. The product was purified by flash chromatography, eluting with a gradient of methylene chloride to 10% methanol in methylene chloride. Fractions were combined and evaporated to give 2-(3-t-butoxycarbonylaminophenyl)-3-di(ethoxy)phosphinoylpropanoic acid ethyl ester, 650 mg, as a clear oil, which was used in the next step.

G. 2-(3-t-Butoxycarbonylaminophenyl)-3-di(ethoxy) phosphinoylpropanoic acid ethyl ester (650 mg, 1.5 mmol) and 6N HCl in dioxane were combined in a 25 mL flask and stirred at ambient temperature for 6 hours. The reaction mixture was evaporated to an oil, dried in vacuo for 48 hours to give a product as an oil, 630 mg. The product was purified in 2 batches by preparative HPLC. Fractions were combined and evaporated to oil, which was dried under high vacuum overnight to give 2-(3-aminophenyl)-3-di(ethoxy)phosphinoylpropanoic acid ethyl ester, 350 mg, as an oil, which was used in the next step.

H. 2-(3-aminophenyl)-3-di(ethoxy)phosphinoylpropanoic acid ethyl ester (350.0 mg, 0.96 mmol), N,N'-di(t-butoxycarbonyl)guanidine triflate (375 mg, 0.96 mmol), chloroform (10 mL) and triethylamine (133.4 mL, 0.96 mmol) were combined in a 25 ml flask and stirred at 50° C. for 27 hours. The solvents were evaporated. The resulting residue was dissolved in acetonitrile/water (8 mL) and purified by preparative chromatography. The fractions were combined and evaporated to an oil, which was dried under high vacuum for 48 hours to give 107 mg of 2-(3-N,N'-di(t-butoxycarbonyl)-guanidinophenyl)-3-di(ethoxy)phosphinoylpropanoic acid ethyl ester, which was used in the next step.

I. 2-(3-N,N'-di(t-Butoxycarbonyl)guanidinophenyl)-3-di(ethoxy)-phosphinoylpropanoic acid ethyl ester (107 mg, 0.19 mmol) was combined with 6 N HCl (5 mL) and the mixture was heated to 80° C. for 4 hours. The solvents were evaporated. The resulting residue (80 mg) was purified by preparative HPLC. The fractions were combined and evaporated to produce 2-(3-guanidinophenyl)-3-phosphonopropanoic acid, as an oil, (43 mg), NMR ($D_2O$) 2.20 (m, 1), 2.57 (m, 1), 4.11 (m, 1), 7.25 (d, 1), 7.35 (s, 1), 7.40 (d, 1), 7.49 (t, 1) ppm.

J. In a similar manner, other compounds of formula (If) are prepared.

EXAMPLE 5

Compounds of Formula (IIa) and Formula (III)

A. Following a procedure reported by Hoffmann, M., *Synthesis* (1986), 557A, a solution of (R)-1-(benzyloxycarbonyl) amino-2-methylpropylphosphonic acid (691.0 mg, 2.41 mmol) in 8 mL of DMF was cooled to −20° C. using a dry ice/methanol bath. To this solution was added thionyl chloride (0.21 mL, 2.88 mmol) and stirred at −5° C. for 25 minutes. Racemic 2-hydroxy-2-(3-(t-butoxycarbonylamino)phenyl)ethanoic acid methyl ester (683.4 mg, 2.43 mmol) was added as a solution in 2 mL of DMF and the reaction was allowed to warm to ambient temperature. After stirring for 4 days (total reaction time 87 hrs), the reaction had almost gone to completion (95%). To this reaction mixture 5 mL of saturated $NaHCO_3$ was added. The solution was washed with ether (2×), acidified to pH 2 with concentrated HCl, and extracted with ethyl acetate (3×). The combined ethyl acetate extracts were dried over $MgSO_4$, filtered, and concentrated in vacuo to give a mixture of product and starting material. Purification via $SiO_2$ gel flash column chromatography ($CH_2Cl_2$, then methanol) provided 1.1966 g (90%) of 2-(3-(t-butoxycarbonylamino)phenyl)-2-((1-(benzyloxycarbonyl)amino-2-methylpropyl)(hydroxy)phosphinoyloxy)ethanoic acid methyl ester; as a mixture of diastereomers.

B. To a solution of 2-(3-(t-butoxycarbonylamino)phenyl)-2-((1-(benzyloxycarbonyl)-amino-2-methylpropyl)(hydroxy) phosphinoyloxy)ethanoic acid methyl ester (1.01 g, 1.84 mmol) in 11 mL of $CH_2Cl_2$ was added 5 mL of TFA. After stirring for 2 hours at ambient temperature, the solution was concentrated in vacuo and azeotrope with $CH_2Cl_2$ and methanol to give a product as a yellow oil that solidified upon exposure to diethyl ether. The resulting off-white solid, 2-(3-aminophenyl)-2-((1-(benzyloxycarbonyl)amino-2-methylpropyl)(hydroxy)-phosphinoyloxy)ethanoic acid methyl ester, was used without further purification.

C. To a solution of 2-(3-aminophenyl)-2-((1-(benzyloxycarbonyl)amino-2-methylpropyl)(hydroxy)phosphinoyloxy)

ethanoic acid methyl ester in 12 mL of CH₃CN was added DIEA (1.0 mL, 5.74 mmol) and N,N'-bis(t-butoxycarbonyl)-1-guanylpyrazole (642.1 mg, 2.07 mmol). After heating at 56° C. for 22 hrs, the reaction was allowed to cool to ambient temperature. The solution was concentrated in vacuo, redissolved in ethyl acetate, washed with 1N HCl and brine, dried over MgSO₄, filtered, and concentrated in vacuo to give a yellow oil, 2-(3-(N,N'-di(t-butoxycarbonyl)-guanidino)phenyl)-2-((1-(benzyloxycarbonyl)amino-2-methylpropyl)(hydroxy)-phosphinoyloxy)ethanoic acid methyl ester, that was used without further purification.

D. To a slurry of 2-(3-(N,N'-di(t-butoxycarbonyl)guanidino)phenyl)-2-((1-(benzyloxycarbonyl)amino-2-methylpropyl)(hydroxy)phosphinoyloxy)ethanoic acid methyl ester in 10 mL of MeOH and 5 mL of H₂O was added LiOH (411.9 mg, 9.82 mmol). After stirring the cloudy yellow solution for 2 hours, the reaction was acidified to pH 2 with 1M NaHSO₄ and extracted with CH₂Cl₂ (3×). The combined organic layers were dried over MgSO₄, filtered, and concentrated in vacuo to give 2-(3-(N,N'-di(t-butoxycarbonyl)guanidino)phenyl)-2-((1-(benzyloxycarbonyl)amino-2-methylpropyl)-(hydroxy)phosphinoyloxy)ethanoic acid as a yellow oil that was used without further purification.

E. To a solution of 2-(3-(N,N'-di(t-butoxycarbonyl)guanidino)phenyl)-2-((1-(benzyloxycarbonyl)amino-2-methylpropyl)(hydroxy)phosphinoyloxy)ethanoic acid in 10 mL of CH₂Cl₂ was added 5 mL of TFA. After stirring for 2 hours at ambient temperature, the solution was concentrated in vacuo and azeotrope with CH₂Cl₂ and MeOH. Purification by preparatory HPLC separated the two diastereomers and provided 72.9 mg (8%) of one diastereomer and 90.1 mg (10%) of 2-(3-guanidinophenyl)-2-((1-(benzyloxycarbonyl)amino-2-methylpropyl)(hydroxy)-phosphinoyloxy)ethanoic acid, NMR (DMSO-d₆) 0.85 (m, 6), 2.05 (m, 1), 3.70 (m, 1), 4.80 (AB q, 2: doublets at 4.70, 4.90), 5.65 (d, 1), 7.20 (d, 1), 7.25-7.50 (m, 14), 9.85 (s, 1) ppm.

F. In a similar manner as described above, the following compounds of formula (IIa) were prepared:
2-(3-aminophenyl)-2-((phenyl)(hydroxy)phosphinoyloxy)ethanoic acid, NMR (DMSO-d₆) 5.68 (d, 1), 7.30-7.34 (m, 1), 7.40-7.46 (m, 5), 7.46-7.54 (m, 1) ppm;
2-(3-guanidinophenyl)-2-((1-amino-2-methylpropyl)(hydroxy)phosphinoyloxy)ethanoic acid, NMR (DMSO-d₆) 1.00 (m, 6), 2.08 (m, 1), 2.86 (dd, 1), 3.93 (br s, 3), 5.62 (d, 1), 7.16 (d, 1), 7.28 (s, 1), 7.33 (d, 1), 7.40 (t, 1), 7.47 (m, 2), 7.83 (br s, 2), 9.89 (s, 1) ppm; and NMR (DMSO-d₆) 1.00 (m, 6), 2.08 (m, 1), 2.87 (dd, 1), 3.68 (br s, 3), 5.64 (d, 1), 7.17 (d, 1), 7.28 (s, 1), 7.31 (d, 1), 7.39 (t, 1), 7.47 (m, 2), 7.83 (br s, 2), 9.89 (s, 1) ppm; and
2-(3-guanidinophenyl)-2-((1-(2-phenylethyl)amino-2-methylpropyl)(hydroxy)-phosphinoyloxy)ethanoic acid, (DMSO-d₆) 0.92 (m, 6), 2.22 (m, 1), 2.38-2.56 (m, 1), 2.82-2.98 (m, 1), 3.10-3.30 (1 m), 3.20 (1, dd), 3.36-3.46 (m, 2) 5.62 (d, 1), 7.18-7.20 (m, 9) 7.50 (m, 2), 9.90 (s, 1) ppm.

G. (1-Benzyloxycarbonylamino-2-methylpropyl)phosphonic acid (600 mg, 2.1 mmol) was dissolved in 20 mL DMF, cooled down to −30° C. over a dry-ice/acetone bath, then sulfonyl chloride (0.17 ml, 2.3 mmol) was added dropwise to the reaction mixture. The resulting reaction mixture was stirred at 0° C. for 30 minutes, then a solution of 5-(3-N,N'-di(t-butoxycarbonyl)guanidinophenyl)(hydroxy)methyltetrazole (900 mg, 2.0 mmol) in 5 mL DMF was added dropwise. The reaction mixture was stirred at ambient temperature overnight. The reaction mixture was diluted with 200 mL ethyl acetate, washed with 3×100 mL water, brine. The crude mixture was purified by flash column on silica gel to afford 2-methyl-1-[1-(3-N,N'-di(t-butoxycarbonyl)guanidinophenyl)-1-tetrazolylmethoxy](hydroxy)-phosphinoylpropylcarbamic acid, benzyl ester (100 mg, 0.14 mmol), which was used in the next step.

H. To a solution of 2-methyl-1-[1-(3-N,N'-di(t-butoxycarbonyl)guanidinophenyl)-1-tetrazolylmethoxy](hydroxy)phosphinoyl-propylcarbamic acid, benzyl ester (100 mg, 0.14 mmol) in 3 mL methylene chloride was added TFA (0.4 mL) at 0° C. The reaction mixture was then stirred at 5° C. for 3 hours. The crude product was purified by preparative HPLC to afford 2-methyl-1-[1-(3-guanidinophenyl)-1-tetrazolylmethoxy](hydroxy)phosphinoyl-propylcarbamic acid, benzyl ester, as TFA salt (50 mg) NMR, DMSO-d₆ 0.84 (m, 6), 2.01 (m, 1), 3.72 (m, 1), 4.70 (m, 1), 4.94 (m, 1), 6.76 (d, 1), 7.20-7.50 (m, 9) ppm.

EXAMPLE 6

Compounds of Formula (Ig)

A. To a solution of 1-(benzyloxycarbonylamino)-2-methylpropyl-phosphonous acid ethyl ester (6.2 g 20.7 mmol) in 150 ml CH₂Cl₂ was added DIEA (6.5 mL, 47.5 mmol). The mixture solution was cooled down to 0° C. over an ice-water bath. TMSCI (5.5 mL, 42.0 mmol) was added dropwise under N₂. The reaction mixture was stirred at ambient temperature for 2 hours, then cooled to 0° C. again. A solution of 2-(3-(t-butoxycarbonylamino)methylphenyl)-propenoic acid methyl ester (6.7 g, 23.0 mmol) in 15 mL CH₂Cl₂ was added to the reaction mixture. The resulting reaction mixture was stirred at ambient temperature for 18 hours. The reaction was quenched by 10 mL MeOH, then concentrated in vacuo, and the residue was taken up into 300 mL ethyl acetate. The organic phase was washed with 2 N NaHSO₄, water, and brine. The solvent was evaporated in vacuo, and the crude product was purified by flash chromatography on silica gel to afford 2-(3-(t-butoxycarbonylamino)methylphenyl)-3-((1-(benzyloxycarbonyl)amino-2-methylpropyl)(ethoxy)phosphinoyl)propanoic acid methyl ester (10.7 g, 18.1 mmol, 81%) as white solid.

B. In a similar manner, the following compound of the invention was prepared:
2-(3-(t-butoxycarbonylamino)methylphenyl)-3-((1-(benzyloxycarbonyl)amino-2-methylpropyl)(ethoxy)phosphinoyl)propanoic acid t-butyl ester, NMR (DMSO-d₆) 0.90 (m, 6), 1.00-1.15 (m, 3), 1.29 (s, 9), 1.35 (s, 9), 1.80-2.05 (m, 2), 2.60 (m, 1), 3.60-3.95 (m, 4), 4.08 (d, 2), 5.00 (m, 2), 7.10 (m, 3), 7.20-7.40 (m, 7), 7.46-7.75 (d, 1) ppm.

C. In a similar manner, but after treatment under standard hydrolysis conditions, the following compounds of the invention were made:
2-phenyl-3-((1-(benzyloxycarbonyl)amino-2-methylpropyl)(hydroxy)phosphinoyl)-propanoic acid, NMR (DMSO-d₆) 0.88 (m, 6), 1.80 (m, 1), 2.08 (m, 1), 3.55 (m, 1), 3.80 (m, 1), 4.97 (AB q, 2: doublets at 5.02, 4.95), 7.15-7.30 (m, 10), 9.85 (s, 1) ppm;
2-(3-(t-butoxycarbonylamino)methylphenyl)-3-((1-(benzyloxycarbonyl)amino-2-methylpropyl)(hydroxy)phosphinoyl)propanoic acid t-butyl ester, NMR (DMSO-d₆) 0.88 (d, 6), 1.33 (s, 9), 1.39 (s, 9), 1.75 (m, 1), 2.10 (m, 1), 2.40 (m, 1), 3.52 (m, 1), 3.67 (m, 1), 4.08 (d, 2), 5.02 (q, 2), 7.00-7.18 (m, 3), 7.20-7.40 (m, 7) ppm; and
2-tetrahydroisoquinolinyl-3-((1-(benzyloxycarbonyl)amino-2-methylpropyl)-(hydroxy)phosphinoyl)propanoic acid, NMR (DMSO-d₆) 0.88 (m, 6), 1.78 (m, 1), 2.07 (m, 1), 2.48 (m, 1), 2.92 (m, 2), 3.34 (m, 2), 2.94 (m, 1), 3.54

(m, 1), 3.76 (m, 1), 4.21 (q, 2), 5.01 (m, 2), 7.02-7.17 (m, 3), 7.31 (m, 4), 7.40 (q, 1), 9.02 (s, 2) ppm.

EXAMPLE 7

Compounds of Formula (Ih)

A. To a solution of 2-(3-(t-butoxycarbonylamino)methylphenyl)-3-((1-(benzyloxycarbonyl)amino-2-methylpropyl)(ethoxy)phosphinoyl)propanoic acid methyl ester (10.6 g, 18.0 mmol) in 200 mL methanol was added Pd/C (10%) (2.1 g). The reaction mixture was hydrogenated in $H_2$ (50 psi) for 2 to 3 hours. The catalyst was filtered over a celite pad. The solvent was removed in vacuo to afford 2-(3-(t-butoxycarbonylamino)methylphenyl)-3-((1-amino-2-methylpropyl)(ethoxy)-phosphinoyl)propanoic acid methyl ester (7.1 g, 15.6 mmol, 87%) as white solid, NMR (DMSO-$d_6$) 0.80-0.91 (m, 6), 1.05-1.18 (m, 3), 1.37 (s, 9), 1.46 (m, 1), 1.90 (m, 1), 2.00-2.20 (m, 1), 2.56-2.64 (m, 1), 3.56 (s, 3), 3.70-3.95 (m, 3), 4.08 (d, 2), 7.10-7.20 (3, m), 7.24 (m, 1), 7.38 (t, 1) ppm.

B In a similar manner, the following compounds of the invention were prepared:

2-(3-(t-butoxycarbonylamino)methylphenyl)-3-((1-amino-2-methylpropyl)(hydroxy)-phosphinoyl)propanoic acid t-butyl ester, NMR (CD$_3$OD) 0.89 (m, 6), 1.3-1.5 (d, 18), 3.9 (m, 1), 4.2 (s, 2), 7.0-7.4 (m, 4) ppm, NMR (DMSO-$d_6$) 0.96 (dd, 6), 1.30 (s, 9), 1.38 (s, 9), 1.92 (m, 1), 2.10 (m, 1), 2.50 (m, 1), 2.78 (m, 1), 3.78 (m, 1), 4.08 (d, 2), 7.10 (m, 3), 7.28 (t, 1), 7.38 (t, 1) ppm, and NMR (DMSO-$d_6$) 0.96 (dd, 6), 1.30 (s, 9), 1.38 (s, 9), 1.92 (m, 1), 2.13 (m, 1), 2.58 (m, 1), 3.05 (m, 1), 3.80 (m, 1), 4.10 (d, 2), 7.10 (m, 3), 7.28 (t, 1), 7.38 (t, 1) ppm; and 2-(3-(t-butoxycarbonylamino)methylphenyl)-3-((1-amino-2-methylpropyl)(ethoxy)-phosphinoyl)propanoic acid t-butyl ester, NMR (DMSO-$d_6$) 0.90 (m, 6), 1.10-1.18 (m, 3), 1.29 (s, 9), 1.38 (s, 9), 1.95-2.05 (m, 2), 2.55-2.80 (m, 2), 3.76-4.0 (m, 3), 4.08 (d, 2), 7.10 (m, 3), 7.25 (t, 1), 7.36 (t, 1) ppm.

C. In a similar manner, other compounds of formula (Ih) are prepared.

EXAMPLE 8

Compounds of Formula (Ii) and Formula (Ij)

A. To a solution of 2-(3-(t-butoxycarbonylamino)methylphenyl)-3-((1-amino-2-methylpropyl)(ethoxy)phosphinoyl)propanoic acid methyl ester (344 mg, 0.75 mmol) in methylene chloride (10 mL) was added DIEA (394 μL, 2.25 mmol) followed by DMAP (3.4 mg (cat.)). The reaction mixture was cooled to 0° C. and a solution of benzenesulfonylchloride (200 mg, 1.13 mmol) in methylene chloride was added dropwise over 15 minutes. The reaction mixture was stirred at 0° C. for 30 minutes and allowed to warm to ambient temperature overnight. The reaction was diluted with methylene chloride and washed with 2 N aq NaHSO$_4$, water, brine and dried over sodium sulfate. Evaporation gave a crude residue (425 mg) that was dissolved in 2.5 mL of methylene chloride and cooled to 0° C. under $N_2$. TMSBr (1 mL) was added dropwise and the reaction was stirred at ambient temperature overnight, quenched with MeOH and evaporated. The resulting residue was dissolved in 5 mL of MeOH/H$_2$O (1:1), neutralized with 0.25 M aq LiOH and 300 mg of LiOH and 10 mL of H$_2$O. The reaction mixture was stirred at ambient temperature overnight. The solvents were evaporated and purification by preparative HPLC yielded 150 mg of 2-(3-(amino)methylphenyl)-3-((1-(phenylsulfonyl)amino-2-methylpropyl)(hydroxy)-phosphinoyl)propanoic acid, NMR (DMSO-$d_6$) 0.5-0.8 (m, 6), 1.8 (m, 1), 1.92 (m, 1), 2.35 (m, 1) 3.25 (m, 1), 3.82 (m, 1), 4.0 (s, 2), 7.2 (dd, 1), 7.25-7.4 (m, 3), 7.4-7.6 (m, 3), 7.8 (m, 3), 8.18 (s, 3) ppm.

B. In a similar manner, the following compound of the invention was prepared:

2-(3-(t-butoxycarbonylamino)methylphenyl)-3-((1-(3-phenylpropylsulfonyl)amino-2-methylpropyl)(ethoxy)phosphinoyl)propanoic acid, t-butyl ester, NMR (DMSO-$d_6$) 0.90 (d, 6), 1.15 (t, 3), 1.29 (s, 9), 1.35 (s, 9), 1.90-2.10 (m, 4), 2.65 (m, 3), 3.04 (m, 2), 3.38 (m, 1), 3.75 (m, 1), 3.90 (q, 2), 4.08 (d, 2), 7.10-7.30 (m, 9), 7.35 (t), 7.50 (d, 1) ppm.

C. In a similar manner, 2-(benzyloxycarbonyl)amino-3-phenylpropylsulfonyl chloride (160 mg, 0.46 mmol) was suspended in 10 mL methylene chloride, which had been cooled to 0° C. by an ice-water bath. A solution of 2-(3-(t-butoxycarbonylamino)-methylphenyl)-3-((1-amino-2-methylpropyl)(hydroxy)phosphinoyl)propanoic acid t-butyl ester (200 mg, 0.42 mmol) in 3 mL methylene chloride was added dropwise to the suspension. The resulting mixture was stirred at ambient temperature overnight. The mixture was washed with 2N NaHSO$_4$, water, and brine. The organic phase was concentrated in vacuo. Purification by chromatograph on silica gel afforded a yellow solid, 2-(3-(t-butoxycarbonylamino)methylphenyl)-3-((1-(3-phenyl-2-(benzyloxy-carbonyl)aminopropylsulfonyl)amino-2-methylpropyl)(hydroxy)phosphinoyl)propanoic acid t-butyl ester, 70 mg.

D. To a solution of 2-(3-(t-butoxycarbonylamino)methylphenyl)-3-((1-(3-phenyl-2-(benzyloxycarbonyl)aminopropylsulfonyl)amino-2-methylpropyl)(hydroxy)phosphinoyl)propanoic acid t-butyl ester (70 mg) in methylene chloride (0.5 mL) was added 2 mL TFA, and the reaction mixture was stirred at ambient temperature for three hours. The reaction mixture was concentrated in vacuo. The residue oil was purified by HPLC to afford a white solid, 2-(3-(amino)methylphenyl)-3-((1-(3-phenyl-2-(benzyloxycarbonyl)aminopropylsulfonyl)-amino-2-methylpropyl)(hydroxy)phosphinoyl)propanoic acid, 20 mg, NMR (DMSO-$d_6$) 0.88 (m, 6), 1.88-2.10 (m, 2), 2.58 (m, 1), 2.70 (m, 1), 2.90 (m, 1), 3.20-3.40 (m, 3), 3.85 (m, 1), 3.95 (s, 2), 4.13 (m, 1), 4.90 (m, 2), 7.10-7.40 (m, 14) ppm.

E. In a similar manner, other compounds of the invention were prepared:

2-(3-(amino)methylphenyl)-3-((1-(3-phenylpropylsulfonyl)amino-2-methylpropyl)-(hydroxy)phosphinoyl)propanoic acid, methyl ester, NMR (DMSO-$d_6$) 0.90 (m, 6), 1.91-2.10 (m, 4), 2.63 (m, 3), 2.93-3.15 (m, 2), 3.26 (m, 1), 3.55 (s, 3), 3.92-4.00 (m, 3), 7.10-7.40 (m, 9) ppm; and NMR (DMSO-$d_6$) 0.90 (dd, 6), 1.90-2.10 (m, 4), 2.64 (m, 3), 2.96-3.14 (m, 2), 3.26 (m, 1), 3.54 (s, 3), 3.65-4.00 (m, 3), 7.15-7.40 (m, 9) ppm;

2-(3-(t-butoxycarbonylamino)methylphenyl)-3-((1-(3-phenylpropylsulfonyl)amino-2-methylpropyl)(hydroxy)phosphinoyl)propanoic acid, NMR (DMSO-$d_6$) 0.88 (m, 6), 1.27 (s, 9), 1.91-2.10 (m, 4), 2.60 (m, 3), 2.95-3.13 (m, 2), 3.25 (m, 1), 3.80 (m, 1), 4.08 (m, 2), 7.10-7.30 (m, 9), 7.36 (q, 1) ppm;

2-(3-(t-butoxycarbonylamino)methylphenyl)-3-((1-(3-phenylpropylsulfonyl)amino-2-methylpropyl)(hydroxy)phosphinoyl)propanoic acid, methyl ester, NMR (DMSO-$d_6$) 0.90 (m, 6), 1.28 (s, 9), 1.91-2.10 (m, 4), 2.60 (m, 3), 2.95-3.12 (m, 2), 3.25 (m, 1), 3.53 (s, 3), 3.90 (m, 1), 4.06 (m, 2), 7.10-7.40 (m, 9) ppm;

2-(3-(amino)methylphenyl)-3-((1-(3-phenylpropylsulfonyl)amino-2-methylpropyl)-(hydroxy)phosphinoyl)propanoic acid;

(2R)-2-(3-(amino)methylphenyl)-3-(((1R)-1-(3-phenylpropylsulfonyl)amino-2-methylpropyl)(hydroxy)phosphinoyl)propanoic acid, $[\alpha]_D=-26°$ (c=9 mg/mL, 1:1 methanol/water), NMR (DMSO-$d_6$) 0.92 (d, 6), 1.94 (m, 3), 2.06 (m, 1), 2.61 (m, 3), 2.93-3.10 (m, 2), 3.25 (m, 1), 3.85 (m, 1), 3.98 (q, 2), 7.15-7.40 (m, 9) ppm;

(2S)-2-(3-(amino)methylphenyl)-3-(((1R)-1-(3-phenylpropylsulfonyl)amino-2-methylpropyl)(hydroxy)phosphinoyl)propanoic acid, $[\alpha]_D=+27°$ (c=9 mg/mL, 1:1 methanol/water), NMR (DMSO-$d_6$) 0.90 (dd, 6), 1.90-2.10 (m, 4), 2.65 (m, 3), 2.96-3.12 (m, 2), 3.26 (m, 1), 3.90 (m, 1), 3.98 (q, 2), 7.15-7.40 (m, 9) ppm;

(2R/S)-2-(3-(amino)methylphenyl)-3-(((1S)-1-(3-phenylpropylsulfonyl)amino-2-methylpropyl)(hydroxy)phosphinoyl)propanoic acid, NMR (DMSO-$d_6$) 0.87 (m, 6), 1.90-2.10 (m, 4), 2.58-2.70 (m, 3), 2.93-3.15 (m, 2), 3.25 (m, 1), 3.88 (m, 1), 3.99 (m, 2), 7.15-7.40 (m, 9) ppm;

(2R/S)-2-(3-(amino)methylphenyl)-3-(((1R)-1-(3-phenylpropylsulfonyl)amino-2-methylpropyl)(hydroxy)phosphinoyl)propanoic acid, NMR (DMSO-$d_6$) 0.88 (m, 6), 1.91-2.10 (m, 4), 2.63 (m, 3), 2.93-3.12 (m, 2), 3.25 (m, 1), 3.86 (m, 1), 3.98 (m, 2), 7.15-7.40 (m, 9) ppm;

(2R)-2-(3-(amino)methylphenyl)-3-(((1S)-1-(3-phenylpropylsulfonyl)amino-2-methylpropyl)(hydroxy)phosphinoyl)propanoic acid, $[\alpha]_D=-23°$ (c=9 mg/mL, 1:1 methanol/water), NMR (DMSO-$d_6$) 0.89-0.95 (dd, 6), 1.92-2.07 (m, 4), 2.58-2.72 (m, 3), 2.98-3.15 (m, 2), 3.24-3.31 (m, 1), 3.87-3.93 (m, 1), 4.00-4.02 (dd, 2), 7.16-7.41 (m, 10), 8.17 (s, 3) ppm;

(2S)-2-(3-(amino)methylphenyl)-3-(((1S)-1-(3-phenylpropylsulfonyl)amino-2-methylpropyl)(hydroxy)phosphinoyl)propanoic acid, $[\alpha]_D=+22°$ (c=9 mg/mL, 1:1 methanol/water), NMR (DMSO-$d_6$) 0.96 (m, 6), 1.80-1.90 (m, 3), 2.02-2.10 (m, 1), 2.52-2.64 (m, 3), 2.96-3.08 (m, 2), 3.90 (t, 1), 4.02 (s, 2), 7.14 (m, 3), 7.24 (m, 3), 7.36 (m, 3) ppm;

2-(3-(amino)methylphenyl)-3-((1-(2-phenylethylsulfonyl)amino-2-methylpropyl)-(hydroxy)phosphinoyl)propanoic acid, NMR (DMSO-$d_6$) 0.85 (m, 6), 1.84-2.10 (m, 3), 2.58 (m, 1), 2.80-2.96 (m, 2), 3.11-3.40 (m, 2), 3.78-3.90 (m, 3), 7.10-7.30 (m, 9) ppm;

2-(3-(amino)methylphenyl)-3-((1-(benzylsulfonyl)amino-2-methylpropyl)(hydroxy)-phosphinoyl)propanoic acid, NMR (DMSO-$d_6$) 0.88-0.94 (m, 6), 1.90-2.10 (m, 2), 2.50-2.70 (m, 1), 3.30 (m, 1), 3.90 (m, 1), 4.00 (d, 2), 4.40 (m, 2), 7.20-7.40 (m, 5), 8.15 (m, 4) ppm;

2-(3-(amino)methylphenyl)-3-((1-(2-(naphth-1-yl)ethylsulfonyl)amino-2-methylpropyl)-(hydroxy)phosphinoyl)propanoic acid, NMR (DMSO-$d_6$) 0.80-1.00 (m, 6), 2.00 (m, 2), 2.65 (m, 1), 3.20-3.52 (m, 5), 3.82-4.00 (m, 3) 7.20-7.40 (m, 6), 7.52-7.60 (m, 2), 7.80-8.20 (m, 3) ppm;

2-(3-(amino)methylphenyl)-3-((1-(4-phenylbutylsulfonyl)amino-2-methylpropyl)-(hydroxy)phosphinoyl)propanoic acid, NMR (DMSO-$d_6$) 0.96 (m, 6), 1.46-1.58 (m, 4), 1.92-2.16 (m, 2), 2.52-2.64 (m, 3), 3.12-3.18 (m, 2), 3.20-3.28 (m, 1), 3.90 (m, 1), 4.02 (m, 2), 7.14 (m, 3), 7.24 (m, 3), 7.36 (m, 3) ppm;

2-(3-(amino)methylphenyl)-3-((1-(2-phenylethenylsulfonyl)amino-2-methylpropyl)-(hydroxy)phosphinoyl)propanoic acid, NMR (DMSO-$d_6$) 0.88-1.96 (m, 6), 2.58-2.70 (m, 1), 3.21-3.50 (m, 3), 3.82-3.92 (m, 1), 3.94-4.02 (m, 2), 7.16-7.42 (m, 6), 7.58-7.62 (m, 3), 8.18-8.20 (m, 2) ppm;

2-(3-(amino)methylphenyl)-3-((1-(naphth-1-ylsulfonyl)amino-2-methylpropyl)(hydroxy)-phosphinoyl)propanoic acid, NMR (DMSO-$d_6$) 0.32 (d, 3), 0.38 (d, 3), 1.89 (m, 2), 2.50 (m, 1), 3.20-3.37 (m, 1), 3.83-3.86 (m, 1), 4.02-4.03 (m, 2), 7.30-7.41 (m, 3), 7.52-7.66 (m, 3), 7.70 (m, 1), 8.14 (m, 5), 8.81 (d, 1) ppm;

2-(3-(amino)methylphenyl)-3-((1-(3-trifluoromethylphenylsulfonyl)amino-2-methylpropyl)(hydroxy)phosphinoyl)propanoic acid, NMR (DMSO-$d_6$) 0.55-0.70 (m, 3), 0.70-0.78 (m, 3), 1.80-2.00 (m, 2), 2.50 (m, 1), 3.30-3.48 (m, 1), 3.78-3.92 (m, 1), 4.00 (m, 2), 7.10-7.45 (m, 3), 7.70 (m, 1), 7.90 (m, 1), 8.00-8.40 (m, 3) ppm;

2-(3-(amino)methylphenyl)-3-((1-(4-phenylphenylsulfonyl)amino-2-methylpropyl)-(hydroxy)phosphinoyl)propanoic acid, NMR (DMSO-$d_6$) 0.60-0.90 (m, 6), 1.70-2.10 (m, 2), 2.50 (m, 1), 3.40 (m, 1), 3.80-3.90 (m, 1), 4.00 (s, 2), 7.00-7.60 (m, 6), 7.60-8.00 (m, 6), 8.10 (s, 1) ppm;

2-(3-(amino)methylphenyl)-3-((1-(3-phenyl-2-(benzyloxycarbonyl)aminopropylsulfonyl)-amino-2-methylpropyl)(hydroxy)phosphinoyl)propanoic acid, NMR (DMSO-$d_6$) 0.87 (m, 6), 1.91-2.10 (m, 2), 2.57 (m, 1), 2.71 (m, 1), 2.94 (m, 1), 3.18-3.40 (m, 3), 3.84 (m, 1), 3.94 (m, 2), 4.16 (m, 1), 4.88 (q, 2), 7.10-7.40 (m, 14) ppm;

2-(3-(amino)methylphenyl)-3-((1-(4-pentylphenylsulfonyl)amino-2-methylpropyl)(hydroxy)phosphinoyl)propanoic acid, NMR (DMSO-$d_6$) 0.58-0.80 (m, 9), 1.20 (m, 4), 1.50 (m, 2), 1.90 (m, 2), 2.30 (m, 1), 2.60 (m, 1), 3.10-3.40 (m, 2), 3.80-4.00 (m, 2), 7.10-7.40 (m, 4), 7.50-7.70 (m, 2), 8.18 (m, 2) ppm;

2-(3-(amino)methylphenyl)-3-((1-(3-(4-methoxyphenyl)propylsulfonyl)amino-2-methylpropyl)(hydroxy)phosphinoyl)propanoic acid, NMR (DMSO-$d_6$) 0.89-0.95 (m, 6), 1.83-2.10 (m, 4), 2.52-2.66 (m, 3), 2.92-3.11 (m, 2), 3.21-3.31 (s, 1) 3.71 (d, 3), 3.81-3.92 (m, 1), 4.00-4.02 (d, 2), 6.79-6.82 (m, 2), 7.02-7.10 (m, 2), 7.22-7.40 (m, 5), 8.16 (s, 3) ppm;

2-(3-(amino)methylphenyl)-3-((1-(2-(4-methoxyphenyl)ethylsulfonyl)amino-2-methylpropyl)(hydroxy)phosphinoyl)propanoic acid, NMR (DMSO-$d_6$) 0.93-1.00 (m, 6), 1.92-2.07 (m, 2), 2.56-2.69 (m, 1), 2.83-3.03 (m, 3), 3.11-3.60 (s, 33) 3.71 (d, 3), 3.87-3.95 (m, 2), 3.99 (s, 2), 6.82-6.85 (m, 2), 7.12-7.18 (m, 2), 7.28-7.39 (m, 4), 8.14 (s, 3) ppm;

2-(3-(hydrazinocarbonyl)phenyl)-3-((1-(benzyloxycarbonyl)amino-2-methylpropyl)-(hydroxy)phosphinoyl)propanoic acid, NMR (DMSO-$d_6$) 0.90 (m, 6), 1.86 (m, 1), 2.06 (m, 1), 2.57 (m, 1), 3.54 (m, 1), 3.90 (m, 1), 5.00 (q, 2), 7.26 (m, 5), 7.43 (m, 3), 7.77 (m, 2) ppm;

2-(3-(amino)methylphenyl)-3-((1-(methylsulfonyl)amino-2-methylpropyl)-(hydroxy)phosphinoyl)propanoic acid, NMR (DMSO-$d_6$) 0.96 (m, 6), 1.80-2.20 (m, 2), 2.60 (m, 1), 2.95 (m, 3), 3.43 (m, 1), 3.85 (m, 1), 4.00 (m, 2), 7.18-8.30 (m, 5) ppm;

2-(3-(amino)methylphenyl)-3-((1-(methylcarbonyl)amino-2-methylpropyl)(hydroxy)-phosphinoyl)propanoic acid, NMR (DMSO-$d_6$) 0.83-0.91 (m, 6), 1.70-1.85 (m, 5), 2.10 (m, 1), 3.48 (m, 1), 3.85 (m, 1), 3.99 (m, 2), 7.20-8.20 (m, 4) ppm;

2-(3-(amino)methylphenyl)-3-((1-(thien-2-ylsulfonyl)amino-2-methylpropyl)-(hydroxy)phosphinoyl)propanoic acid, NMR (DMSO-$d_6$) 0.6-0.9 (m, 6), 1.21 (m, 1), 1.7 (m, 1), 1.98 (m, 1), 2.2 (m, 1), 3.9 (m, 1), 3.98 (s, 2), 7.0 (q, 1), 7.06 (q, 1), 7.15 (t, 1), 7.3 (m, 1), 7.58 (dd, 1), 7.78 (dd, 1), 8.18 (s, 2) ppm;

2-(3-(amino)methylphenyl)-3-((1-(4-acetamidophenylsulfonyl)-amino-2-methylpropyl)(hydroxy)phosphinoyl)propanoic acid, NMR (DMSO-$d_6$) 0.5-0.8 (m, 6), 1.9 (m, 1), 2.05 (s, 3), 3.82 (m, 1), 4.0 (s, 2), 7.1-7.4 (m, 4), 7.6-7.82 (m, 4), 8.15 (s, 2), 10.25 (s, 1) ppm;

2-(3-(amino)methylphenyl)-3-((1-(2-benzyloxyethylsulfonyl)amino-2-methylpropyl)(hydroxy)phosphinoyl)propanoic acid, NMR (DMSO-d$_6$) 0.84 (m, 6), 1.86-1.2.16 (m, 2), 2.55-2.70 (m, 1), 3.23-3.34 (m, 1), 3.36-3.46 (m, 2) 3.70-3.80 (m, 2), 3.80-3.92 (m, 1), 4.02 (s, 2), 4.46 (m, 2), 7.24-7.40 (m, 9) ppm;

2-(3-(amino)methylphenyl)-3-((1-(2-hydroxyethylsulfonyl)amino-2-methylpropyl)(hydroxy)phosphinoyl)propanoic acid, NMR (DMSO-d$_6$) 0.84 (m, 6), 1.86-1.2.16 (m, 2), 3.18-3.28 (m, 2), 3.72-3.78 (m, 2), 3.60-3.82 (m, 1), 4.02 (m, 2), 7.24 (d, 1) 7.26-7.42 (m, 3) ppm;

2-(3-(amino)methylphenyl)-3-((1-(benzothiadiazolylsulfonyl)amino-2-methylpropyl)-(hydroxy)phosphinoyl)propanoic acid;

2-(3-aminophenyl)-3-((1-(3-phenylpropylsulfonyl)amino-2-methylpropyl)(hydroxy)phosphinoyl)propanoic acid, NMR (DMSO-d$_6$) 0.77-0.81 (m, 6), 1.80-2.00 (m, 4), 2.42-2.58 (m, 3), 2.80-3.00 (m, 2), 3.20-3.28 (m, 1), 3.72-3.90 (m, 1), 6.95-7.35 (m, 10) ppm; and 2-(3-guanidinophenyl)-3-((1-(3-phenylpropylsulfonyl)amino-2-methylpropyl)(hydroxy)-phosphinoyl)propanoic acid, NMR (DMSO-d$_6$) 0.82-0.95 (m, 6), 1.85-2.10 (m, 4), 2.58-2.70 (m, 3), 2.90-3.18 (m, 2), 3.40 (m, 1), 3.84-3.95 (m, 1), 7.08-7.50 (m, 10) ppm.

F. In a similar manner, other compounds of formula (Ii) and (Ij) are prepared.

G. In a similar manner, the following compounds of the invention and compounds of formula (III) were prepared:

2-(3-guanidinophenyl)-3-((1-(benzyloxycarbonyl)amino-3-methylbutyl)(hydroxy)phosphinoyl)propanoic acid, NMR (DMSO-d$_6$) 0.76-0.91 (m, 6), 1.37 (m, 1), 1.52 (m, 1), 1.95 (m, 1), 2.45 (m, 1), 3.72 (m, 2), 5.01 (m, 2), 7.14 (m, 2), 7.36 (m, 5), 7.44 (m, 2) ppm;

2-(3-guanidinophenyl)-3-(((benzyloxycarbonyl)aminomethyl)(hydroxy)phosphinoyl)-propanoic acid, NMR (DMSO-d$_6$) 2.02 (m, 1), 2.46 (m, 1), 3.24 (m, 2), 3.88 (m, 1), 5.01 (s, 2), 7.11-7.45 (m, 9) ppm;

2-(3-guanidinophenyl)-3-((1-(benzyloxycarbonyl)aminoethyl)(hydroxy)phosphinoyl)-propanoic acid, NMR (DMSO-d$_6$) 1.17 (m, 3), 1.94 (m, 1), 2.42 (m, 1), 3.67 (m, 1), 3.88 (m, 1), 4.98 (m, 2), 7.14 (m, 3), 7.33 (m, 6) ppm;

2-(3-guanidinophenyl)-3-((1-(benzyloxycarbonyl)amino-2-methylpropyl)(hydroxy)-phosphinoyl)propanoic acid, NMR (DMSO-d$_6$) 0.92 (m, 6), 2.02 (m, 2), 2.38 (m, 1), 3.56 (m, 1), 3.85 (m, 1), 5.03 (m, 2), 7.11-7.40 (m, 9) ppm, NMR (DMSO-d$_6$) 0.90 (m, 6), 1.93 (m, 1), 2.04 (m, 1), 2.42 (m, 1), 3.53 (m, 1), 3.83 (m, 1), 5.02 (m, 2), 7.12 (m, 3), 7.28-7.38 (m, 8) ppm, and NMR (DMSO-d$_6$) 0.90 (m, 6), 1.92 (m, 1), 2.03 (m, 1), 2.40 (m, 1), 3.55 (m, 1), 3.86 (m, 1), 5.02 (m, 2), 7.13 (m, 3), 7.24-7.38 (m, 6) ppm;

2-(2-chloro-5-guanidinophenyl)-3-((1-(benzyloxycarbonyl)amino-2-methylpropyl)(hydroxy)phosphinoyl)propanoic acid, NMR (DMSO-d$_6$) 0.91 (m, 6), 2.10 (m, 2), 2.46 (m, 1), 3.56 (m, 1), 4.26 (m, 1), 5.02 (m, 2), 7.11 (d, 1), 7.24-7.52 (m, 7) ppm, NMR (DMSO-d$_6$) 0.90 (m, 6), 2.01-2.18 (m, 2), 2.43 (m, 1), 3.58 (m, 1), 4.24 (m, 1), 5.03 (m, 2), 7.11 (d, 1), 7.24-7.52 (m, 7) ppm, and NMR (DMSO-d$_6$) 0.90 (m, 6), 2.01-2.18 (m, 2), 2.43 (m, 1), 3.58 (m, 1), 4.25 (m, 1), 5.02 (m, 2), 7.12 (d, 1), 7.24-7.52 (m, 7) ppm;

2-(3-(amino)methylphenyl)-3-((1-(benzyloxycarbonyl)amino-2-methylpropyl)(hydroxy)-phosphinoyl)propanoic acid, mixture of diastereomers, NMR (DMSO-d$_6$) 0.93 (m, 6), 1.81 (m, 1), 2.05 (m, 1), 2.53 (m, 1), 3.96 (s, 2), 5.00 (s, 2), 7.18-7.40 (m, 10) ppm;

2-(3-guanidinophenyl)-3-(((1-benzyloxycarbonylamino-2-phenylethyl)carbonylaminomethyl)(hydroxy)phosphinoyl)propanoic acid, mixture of diastereomers, NMR (DMSO-d$_6$) 0.95 (m, 6), 1.71-2.30 (m, 2), 2.60-2.2.73 (m, 2), 2.90-3.00 (m, 2), 3.70-3.85 (m, 2), 4.90 (m, 2), 7.00-7.60 (m, 14) ppm;

2-(3-(amino)methylphenyl)-3-((1-(2-phenylethylcarbonyl)amino-2-methylpropyl)(hydroxy)phosphinoyl)propanoic acid, NMR (DMSO-d$_6$) 0.76-0.86 (m, 6), 1.72 (m, 1), 2.07 (m, 1), 2.38-2.56 (m, 3), 2.74 (m, 2), 3.85 (m, 2), 4.01 (m, 2), 7.11-7.46 (m, 9), 7.93 (d, 1) ppm; and 2-(3-guanidinophenyl)-3-(((1-benzyloxycarbonylamino-2-phenylethyl)-carbonylaminomethyl)(hydroxy)phosphinoyl)propanoic acid, NMR (DMSO-d$_6$) 1.97 (m, 1), 2.38 (m, 1), 2.64 (m, 1), 2.88 (m, 1), 3.33 (m, 2), 3.84 (m, 1), 4.23 (m, 1), 4.82 (m, 2), 7.03-7.46 (m, 14) ppm, and NMR (DMSO-d$_6$) 1.97 (m, 1), 2.38 (m, 1), 2.64 (m, 1), 2.85 (m, 1), 3.31 (m, 2), 3.83 (m, 1), 4.24 (m, 1), 4.82 (m, 2), 7.01-7.48 (m, 14) ppm.

EXAMPLE 9

Compounds of Formula (IIb) and Formula (IIc)

A. A solution of (1R)-(+)-(1-benzyloxycarbonylamino-2-methylpropyl)phosphonic acid (4.27 g, 14.9 mmol) in 50 mL of DMF was cooled to −20° C. using a dry ice/methanol bath. To this was added thionyl chloride (1.20 mL, 16.5 mmol) and the reaction mixture was stirred at −5° C. for 40 minutes. 2-(3-(N',N"-Di(t-butoxycarbonyl)guanidino)phenyl)-2-hydroxyethanoic acid methyl ester (5.60 g, 13.2 mmol) was added to the reaction mixture as a solution in 15 mL of DMF and the reaction was allowed to warm to ambient temperature. After stirring for 3 days, 20 mL of saturated NaHCO$_3$ was added. The solution was washed with ether (2×), combined and concentrated in vacuo to give a mixture of product and starting material. The product was purified by flash column chromatography (10%-100% ethyl acetate/methylene chloride), followed by methanol to give 5.07 g (55%) of 2-(3-(N',N"-di(t-butoxycarbonyl)guanidino)phenyl)-2-((1R)-(1-(benzyloxycarbonyl)amino-2-methylpropyl)(hydroxy)phosphinoyloxy)ethanoic acid methyl ester.

B. In a similar manner, other compounds of formula (IIb) are prepared.

C. To a solution of palladium(II) acetate (184 mg, 0.82 mmol) in 13 mL of CH$_2$Cl$_2$ was added triethylamine (0.24 mL, 1.72 mmol) and triethylsilane (1.80 mL, 11.3 mmol). After stirring the resulting black slurry for 25 minutes, 2-(3-(N',N"-di(t-butoxycarbonyl)guanidino)phenyl)-2-((1R)-(1-(benzyloxycarbonyl)amino-2-methylpropyl)(hydroxy)phosphinoyloxy)ethanoic acid methyl ester (2.93 g, 4.23 mmol) in methylene chloride (3 mL) was added. The reaction mixture was stirred at ambient temperature for 5.5 hours at which point the reaction was concentrated in vacuo, dissolved in methanol, and filtered. The filtrate was concentrated in vacuo and placed in vacuo overnight to provide 2.7143 g (116%) of 2-(3-(N',N"-di(t-butoxycarbonyl)guanidino)phenyl)-2-((1R)-(1-amino-2-methylpropyl)-(hydroxy)phosphinoyloxy)ethanoic acid methyl ester as an impure white foam.

D. In a similar manner, other compounds of formula (IIc) are prepared.

EXAMPLE 10

Compounds of Formula (IId)

A. To a solution of 2-(3-(N',N"-di(t-butoxycarbonyl)guanidino)phenyl)-2-((1-amino-2-methylpropyl)(hydroxy)phosphinoyloxy)ethanoic acid methyl ester (300 mg, 0.53 mmol) in 8 mL methylene chloride was added DIEA (0.44 mL, 1.06 mmol), which was cooled to 0° C. by an ice-water bath. Then a solution of 2-phenylethenylsulfonyl chloride (120 mg, 0.59 mmol) in 1 mL methylene chloride was added dropwise. The resulting mixture was stirred at ambient temperature for thirty minutes. The mixture was washed with water, 2N NaHSO$_4$, and brine. The organic phase was dried over sodium sulfate and concentrated to afford a yellow solid. Purification by chromatograph on silica gel afforded a yellow solid, 2-(3-(N',N''-di(t-butoxycarbonyl)guanidino)phenyl)-2-((1-(2-phenylethenylsulfonyl)amino-2-methylpropyl)(hydroxy)phosphinoyloxy)ethanoic acid, methyl ester, (220 mg).

B. To a solution of 2-(3-(N',N''-di(t-butoxycarbonyl)guanidino)phenyl)-2-((1-(2-phenylethenylsulfonyl)amino-2-methylpropyl)(hydroxy)-phosphinoyloxy)ethanoic acid, methyl ester (220 mg) in 5 mL methylene chloride was added 1 mL TFA. The reaction mixture was stirred at ambient temperature for 4 hours, then concentrated in vacuo to get an oil. The oil was dissolved in 2.5 mL MeOH, then a solution of LiOH (100 mg) in 3 mL water was added. The reaction mixture was stirred at ambient temperature for 2 hours. The crude product was purified by HPLC directly without work up to afford 2-(3-guanidinophenyl)-2-((1-(2-phenylethenylsulfonyl)amino-2-methylpropyl)-(hydroxy)phosphinoyloxy)ethanoic acid, as a white solid (55 mg) NMR (DMSO-d$_6$) 0.88 (m, 6), 2.10 (m, 1), 3.40 (m, 1), 5.63 (m, 1), 7.10-7.60 (m, 11), 9.80 (d, 1) ppm.

C. In a similar manner as described above in Paragraphs A and B, other compounds of formula (IId) are prepared.

D. Alternatively, to a solution of benzylsulfonyl chloride (101.4 mg, 0.53 mmol) and 2-(3-(N',N''-di(t-butoxycarbonyl)guanidino)phenyl)-2-((1R)-(1-amino-2-methylpropyl)(hydroxy)-phosphinoyloxy)ethanoic acid methyl ester (301.4 mg, 0.54 mmol) in 4 mL of methylene chloride was added triethylamine (0.13 mL, 0.93 mmol). After stirring at ambient temperature for 1.5 hours, the reaction mixture was concentrated in vacuo to give a yellow oil, 2-(3-(N',N''-di(t-butoxycarbonyl)guanidino)phenyl)-2-((1R)-(1-(benzylsulfonyl)amino-2-methylpropyl)-(hydroxy)phosphinoyloxy)ethanoic acid methyl ester, which was used without further purification in the following step.

E. To a slurry of 2-(3-(N',N''-di(t-butoxycarbonyl)guanidino)phenyl)-2-((1R)-(1-(benzylsulfonyl)amino-2-methylpropyl)(hydroxy)phosphinoyloxy)ethanoic acid methyl ester (0.53 mmol) in 6 mL of methanol and 3 mL of H$_2$O was added LiOH (124.3 mg, 5.3 mmol). After stirring for 6 hours, the solution was acidified to pH 2 with concentrated HCl and extracted with methylene chloride (3×). The combined organic layers were dried over MgSO$_4$, filtered, and concentrated in vacuo to give 2-(3-(N',N''-di(t-butoxycarbonyl)guanidino)phenyl)-2-((1R)-(1-(benzylsulfonyl)amino-2-methylpropyl)(hydroxy)phosphinoyloxy)ethanoic acid as a yellow oil that was used without further purification in the following step.

F. To a solution of 2-(3-(N',N''-di(t-butoxycarbonyl)guanidino)phenyl)-2-((1R)-(1-(benzylsulfonyl)amino-2-methylpropyl) (hydroxy)phosphinoyloxy)ethanoic acid (0.53 mmol) in 3 mL of methylene chloride was added TFA (3 mL, 39 mmol). After stirring for 1.5 hours at ambient temperature, the solution was concentrated. Purification by HPLC provided 33.0 mg (12%, 4 steps) of 2-(3-guanidinophenyl)-2-((1-(benzylsulfonyl)amino-2-methylpropyl)(hydroxy)phosphinoyloxy)ethanoic acid as white fluffy solid; NMR (DMSO-d$_6$) 0.92 (m, 6), 2.01 (m, 1), 3.5 (m, 2), 4.54-4.26 (overlapping AB q, 2), 5.74 (overlapping doublets, 1), 7.22 (m, 1), 7.29-7.46 (m, 14), 9.78 (m, 1).

F. In a similar manner, the following compound was prepared:
2-(3-guanidinophenyl)-2-((1-(benzylaminothiocarbonyl)amino-2-methylpropyl)-(hydroxy)phosphinoyloxy)ethanoic acid, NMR (DMSO-d$_6$) 0.91 (m, 6), 2.11 (m, 1), 4.50-4.70 (m, 2), 4.94 (m, 1), 5.60 (m, 1), 7.20-7.40 (m, 9), 8.00 (s, 1), 9.78 (d, 1) ppm.

G. In a similar manner, the following compounds of the invention were prepared:
2-(3-guanidinophenyl)-2-((1-(benzyloxycarbonyl)aminoethyl)(hydroxy)-phosphinoyloxy)ethanoic acid, NMR (DMSO-d$_6$) 1.20 (m, 3), 3.85 (m, 1), 4.90 (AB q, 2), 5.60 (d, 1), 7.20 (d, 1), 7.25-7.50 (m, 14), 9.85 (s, 1) ppm; and NMR (DMSO-d$_6$) 1.20 (m, 3), 3.85 (m, 1), 4.90 (AB q, 2), 5.60 (d, 1), 7.20 (d, 1), 7.25-7.50 (m, 14), 9.85 (s, 1) ppm;

2-(3-guanidinophenyl)-2-(((benzyloxycarbonyl)aminomethyl)(hydroxy)-phosphinoyloxy)ethanoic acid; NMR (DMSO-d$_6$) 3.40 (m, 2), 4.95 (s, 2), 5.65 (d, 1), 7.20 (d, 1), 7.25-7.50 (m, 14), 9.80 (s, 1) ppm;

2-(3-guanidinophenyl)-2-((1-(benzyloxycarbonyl)amino-2-methylpropyl)-(hydroxy)phosphinoyloxy)ethanoic acid; NMR (DMSO-d$_6$) 0.85 (m, 6), 2.05 (m, 1), 3.70 (m, 1), 4.80 (AB q, 2: doublets at 4.70, 4.90), 5.65 (d, 1), 7.20 (d, 1), 7.25-7.50 (m, 14), 9.85 (s, 1) ppm;

2-(3-guanidinophenyl)-2-((1-(benzyloxycarbonyl)aminohexyl)(hydroxy)-phosphinoyloxy)ethanoic acid; a mixture of diastereomers, NMR (DMSO-d$_6$) 0.90 (m, 3), 1.20 (m, 5), 1.30 (m, 1), 1.45 (m, 1), 1.65 (m, 1), 3.60 (m, 1), 4.70-5.00 (m, 2, 2 AB quartets overlapping), 5.55 (d, 0.5), 5.60 (d, 0.5), 6.95 (d, 0.5), 7.00 (d, 0.5), 7.15 (d, 1), 7.30 (m, 10), 7.50 (m, 3), 10.10 (s, 0.5), 10.15 (s, 0.5) ppm;

2-(3-aminophenyl)-2-((1-(benzyloxycarbonyl)amino-2-methylpropyl)-(hydroxy)phosphinoyloxy)ethanoic acid, a mixture of diastereomers, NMR (DMSO-d$_6$) 0.87 (m, 6), 2.03 (m, 1), 3.75 (m, 1), 4.83-5.02 (m, 2, 2 AB quartets overlapping), 5.46 (d, 0.5), 5.48 (d, 0.5), 6.75 (m, 1), 6.86 (m, 2), 7.12 (m, 1), 7.25 (m, 7) ppm;

2-(2-chloro-3-guanidinophenyl)-2-((1-(benzyloxycarbonyl)amino-2-methylpropyl)-(hydroxy)phosphinoyloxy)ethanoic acid, NMR (DMSO-d$_6$) 0.85 (m, 6), 2.02 (m, 1), 3.61 (m, 1), 4.80-5.00 (m, 2), 5.81 (m, 1), 7.10-7.43 (m, 8) ppm, and NMR (DMSO-d$_6$) 0.80 (m, 6), 2.00 (m, 1), 3.51 (m, 1), 4.50-4.80 (m, 2), 5.81 (m, 1), 6.95-743 (m, 8) ppm;

2-(3-guanidinophenyl)-2-((1-(benzyloxycarbonyl)amino-1-phenylmethyl)-(hydroxy)phosphinoyloxy)ethanoic acid, as a mixture of diastereomers, NMR (DMSO-d$_6$) 0.90 (m, 3), 1.20 (m, 5), 1.30 (m, 1), 1.45 (m, 1), 1.65 (m, 1), 3.60 (m, 1), 4.70-5.00 (m, 2, 2 AB quartets overlapping), 5.55 (d, 0.5), 5.60 (d, 0.5), 6.95 (d, 0.5), 7.00 (d, 0.5), 7.15 (d, 1), 7.30 (m, 10), 7.50 (m, 3), 10.10 (s, 0.5), 10.15 (s, 0.5) ppm; and NMR (DMSO-d$_6$) 4.78-4.99 (m, 3: AB q overlapped with m), 5.07 (d, 1), 7.13-7.39 (m, 18), 7.92 (d, 2), 9.82 (s, 1) ppm;

2-(2-fluoro-3-guanidinophenyl)-2-((1-(benzyloxycarbonyl)amino-2-methylpropyl)-(hydroxy)phosphinoyloxy)ethanoic acid, NMR (DMSO-d$_6$) 0.90 (m, 6), 2.03 (m, 1), 3.64 (m, 1), 4.80-4.97 (q, 2), 5.77 (d, 1), 7.20-7.42 (m, 8) ppm, and NMR (DMSO-d$_6$/D$_2$O) 0.88 (m, 6), 2.02 (m, 1), 3.46 (m, 1), 4.55-4.83 (q, 2), 5.78 (d, 1), 7.17-7.37 (m, 8) ppm;

2-(3-guanidinophenyl)-2-((1-(benzyloxycarbonyl)amino-1-cyclohexylmethyl)-(hydroxy)phosphinoyloxy)ethanoic acid, NMR (DMSO-d$_6$) 0.96-1.09 (m, 5), 1.51 (d, 1), 1.57 (m, 2), 1.68 (m, 2), 1.80 (d, 1), 3.55 (m, 1), 4.86 (AB q, 2: doublets at 4.78, 4.93), 5.52 (d, 1), 6.60 (d, 1), 7.06 (d, 1), 7.19-7.33 (m, 8), 7.51 (m, 3), 10.32 (s, 1) ppm;

2-(2-methyl-3-guanidinophenyl)-2-((1-(benzyloxycarbonyl)amino-2-methylpropyl)-(hydroxy)phosphinoyloxy)ethanoic acid, NMR (DMSO-d$_6$) 0.80 (m, 6), 2.04 (m, 1), 2.16 (s, 3), 3.55 (m, 1), 4.63-5.05 (m, 2), 5.78 (m, 1), 7.12-7.38 (m, 8) ppm; NMR (DMSO-d$_6$) 0.80 (m, 6), 2.04 (m, 1), 2.16 (s, 3), 3.55 (m, 1), 4.93-5.00 (m, 2), 5.78 (m, 1), 7.12-7.38 (m, 8) ppm; NMR (DMS DMSO-d$_6$) 0.88 (m, 6), 2.04 (m, 1), 2.16 (s, 3), 3.64 (m, 1), 4.84 (dd, 2), 5.60 (d, 1), 7.26 (m, 8), 9.42 (t, 1) ppm; and NMR (DMSO-d$_6$) 0.88 (d, 6), 2.06 (m, 1), 2.18 (s, 3), 3.64 (m, 1), 4.90 (dd, 2), 5.56 (d, 1), 7.38 (m, 8), 9.36 (s, 1) ppm;

2-(3-guanidinophenyl)-2-((1-(benzyloxycarbonyl)amino-3-methylbutyl)-(hydroxy)phosphinoyloxy)ethanoic acid; NMR (DMSO-d$_6$) 0.74 (d, 3), 0.82 (d, 3), 1.37 (m, 1), 1.51 (m, 2), 3.73 (m, 1), 4.85 (AB q, 2: doublets at 4.76, 4.95), 5.60 (d, 1), 7.15 (d, 1), 7.25-7.43 (m, 14), 9.86 (s, 1) ppm;

2-(3-(amino)methylphenyl)-2-((1-(benzyloxycarbonyl)amino-2-methylpropyl)-(hydroxy)phosphinoyloxy)ethanoic acid, NMR (DMSO-d$_6$) 0.86 (m, 6), 2.06 (m, 1), 3.64 (m, 2), 3.92 (s, 2), 4.90 (m, 2), 5.60 (q, 1), 7.34 (m, 8), 7.50 (s, 1), 8.46 (bs, 2) ppm;

2-(3-(guanidinomethyl)phenyl)-2-((1-(benzyloxycarbonyl)amino-2-methylpropyl)-(hydroxy)phosphinoyloxy)ethanoic acid, NMR (DMSO-d$_6$) 0.88 (m, 6), 2.06 (m, 1), 3.70 (m, 1), 4.36 (d, 2), 4.96 (dd, 2), 5.60 (d, 1), 7.30 (m, 9), 7.94 (t, 1) ppm, and NMR (DMSO-d$_6$) 0.92 (m, 6), 2.12 (m, 1), 3.85 (m, 1), 4.46 (d, 2), 5.06 (dd, 2), 5.68 (d, 1), 7.40 (m, 9), 8.06 (t, 1) ppm;

2-(3-(1-iminoethylaminophenyl))-2-((1-(benzyloxycarbonyl)amino-2-methylpropyl)-(hydroxy)phosphinoyloxy)ethanoic acid, NMR (DMSO-d$_6$) 0.83 (m, 6), 2.02 (m, 1), 2.30 (s, 3), 3.58 (m, 1), 4.78-4.90 (m, 2), 5.60 (m, 1), 7.20-7.43 (m, 9) ppm, and NMR (DMSO-d$_6$) 0.80 (m, 6), 2.00 (m, 1), 2.30 (s, 3), 3.60 (m, 1), 4.80-4.90 (m, 2), 5.60 (m, 1), 7.20-7.45 (m, 9) ppm;

2-(3-(t-butoxycarbonylamino)methylphenyl)-2-((1-(benzyloxycarbonyl)amino-2-methylpropyl)(hydroxy)phosphinoyloxy)ethanoic acid, NMR (DMSO-d$_6$) 0.88 (m, 6), 1.36 (s, 9), 2.04 (m, 1), 3.72 (m, 1), 4.08 (m, 2), 4.88 (m, 1), 5.00 (m, 1), 5.56 (m, 1), 5.68 (d, 1), 7.30 (m, 11) ppm;

2-(3-(ethoxycarbonylamino)methylphenyl)-2-((1-(benzyloxycarbonyl)amino-2-methylpropyl)(hydroxy)phosphinoyloxy)ethanoic acid, NMR (DMSO-d$_6$) 0.92 (m, 6), 1.20 (t, 3), 2.04 (m, 1), 3.76 (m, 1), 4.08 (q, 2), 4.20 (s, 2), 4.90 (m, 1), 5.08 (m, 1), 5.62 (t, 1), 7.30 (m, 11) ppm;

2-(3-(isopropoxycarbonylamino)methylphenyl)-2-((1-(benzyloxycarbonyl)amino-2-methylpropyl)(hydroxy)phosphinoyloxy)ethanoic acid, NMR (DMSO-d$_6$) 0.88 (m, 6), 1.14 (d, 6), 2.04 (m, 1), 3.72 (m, 1), 4.22 (s, 2), 4.74 9 m, 1), 4.86 (m, 1), 4.96 (m, 1), 5.52 (t, 1), 7.30 (m, 11) ppm;

2-(3-(2,2-dimethylpropylcarbonylamino)methylphenyl)-2-((1-(benzyloxycarbonyl)amino-2-methylpropyl)(hydroxy)phosphinoyloxy)ethanoic acid, NMR (DMSO-d$_6$) 0.92 (m, 6), 0.96 (s, 9), 2.02 (s, 2), 2.08 (m, 1), 3.73 (m, 2), 4.26 (m, 2), 4.91 (m, 1), 5.04 (m, 1), 5.58 (dd, 1), 7.23-7.37 (m, 10), 8.27 (m, 1) ppm;

2-(3-guanidinophenyl)-2-((1-(2-phenylethylcarbonyl)amino-2-methylpropyl)-(hydroxy)phosphinoyloxy)ethanoic acid, NMR (DMSO-d$_6$) 0.85 (m, 6), 2.00 (m, 1), 2.40 (m, 2), 2.80 (m, 2), 5.00 (m, 1), 5.40 (m, 1), 7.25-7.50 (m, 11), 7.60 (d, 1), 8.40 (s, 3), 9.75 (s, 1) ppm, and NMR (DMSO-d$_6$) 0.85 (m, 6), 2.00 (m, 1), 2.40 (m, 2), 2.80 (m, 2), 5.00 (m, 1), 5.40 (m, 1), 7.25-7.50 (m, 12), 8.40 (s, 3), 9.75 (s, 1) ppm;

2-(3-guanidinophenyl)-2-((1-(2-phenylethenylcarbonyl)amino-2-methylpropyl)-(hydroxy)phosphinoyloxy)ethanoic acid, mixture of diastereomers, NMR (DMSO-d$_6$) 0.90 (m, 6), 2.10 (m, 1), 4.10 (m, 1), 5.00 (m, 2), 5.65 (m, 1), 6.60 (m, 1), 7.05-7.60 (m, 14), 9.70 (s, 0.5), 9.75 (s, 0.5) ppm;

2-(3-guanidinophenyl)-2-[(1-(1-benzyloxycarbonylamino-2-(4-hydroxyphenyl)ethylcarbonyl)amino-2-methylpropyl)-(hydroxy)phosphinoyloxy]ethanoic acid, NMR (DMSO-d$_6$) 0.83 (d, 3), 0.90 (d, 3), 2.05 (m, 1), 4.00 (m, 1), 4.15 (m, 1), 4.89 (s, 2), 5.57 (d, 1), 6.62 (d, 2), 7.04 (d, 2), 7.19-7.45 (m, 13), 7.65 (m, 1), 9.14 (s, 1), 9.67 (s, 1) ppm;

2-(3-guanidinophenyl)-2-[(1-(1-benzyloxycarbonylamino-2-phenylethylcarbonyl)amino-2-methylpropyl)(hydroxy)phosphinoyloxy]ethanoic acid, NMR (DMSO-d$_6$) 0.86 (d, 3), 0.92 (d, 3), 2.01 (m, 1), 2.83 (AB q, 2), 4.05 (m, 1), 4.28 (m, 1), 4.89 (s, 2), 5.57 (d, 1), 7.14 (m, 5), 7.25 (m, 10), 7.37 (m, 5), 7.83 (d, 1), 9.70 (s, 1) ppm, and NMR (DMSO-d$_6$) 0.86 (d, 3), 0.92 (d, 3), 2.01 (m, 1), 2.83 (AB q, 2), 3.94 (m, 1), 4.20 (m, 1), 4.88 (s, 2), 5.56 (d, 1), 6.52 (m, 1), 7.14 (m, 4), 7.25 (m, 10), 7.37 (m, 4), 7.51 (d, 1), 7.60 (d, 1), 9.69 (s, 1) ppm;

2-(2-fluoro-3-guanidinophenyl)-2-[(1-(1-benzyloxycarbonylamino-2-phenylethylcarbonyl)amino-2-methylpropyl)(hydroxy)phosphinoyloxy]ethanoic acid, NMR (DMSO-d$_6$) 0.77-0.88 (m, 6), 2.05 (m, 1), 2.52 (m, 1), 2.79 (m, 1), 3.94 (m, 1), 4.23 (m, 1), 4.83 (m, 2), 5.71 (m, 1), 7.09-7.48 (m, 13) ppm;

2-(3-guanidinophenyl)-2-[(1-(1-phenylcarbonylamino-2-phenylethylcarbonyl)amino-2-methylpropyl)(hydroxy)phosphinoyloxy]ethanoic acid, mixture of diastereomers- NMR (DMSO-d$_6$) 0.90 (m, 6), 1.05 (t, 3), 2.05 (m, 1), 2.80 (d, 2), 3.80 (m, 2), 3.95 (m, 1), 4.20 (m, 1), 4.85 (dd, 2), 5.55 (m, 1), 7.10-7.45 (m, 13), 7.60 (m, 1), 9.85 (m, 1) ppm;

2-(3-guanidinophenyl)-2-[(1-(1-ethoxycarbonylamino-2-phenylethylcarbonyl)amino-2-methylpropyl)(hydroxy)phosphinoyloxy]ethanoic acid, mixture of diastereomers, NMR (DMSO-d$_6$) 0.90 (m, 6), 1.05 (t, 3), 2.05 (m, 1), 2.80 (d, 2), 3.80 (m, 2), 3.95 (m, 1), 4.20 (m, 1), 4.85 (dd, 2), 5.55 (m, 1), 7.10-7.45 (m, 13), 7.60 (m, 1), 9.85 (m, 1) ppm;

2-(3-guanidinophenyl)-2-[(1-(1-benzyloxycarbonylamino-3-phenylpropylcarbonyl)-amino-2-methylpropyl)(hydroxy)phosphinoyloxy]ethanoic acid, NMR (DMSO-d$_6$) 0.87 (m, 6), 1.51 (m, 1), 1.65 (m, 1), 2.03 (m, 1), 3.85 (m, 2), 4.05 (m, 1), 4.20 (m, 1), 5.00 (m, 2), 5.46 (d, 1), 7.00 (m, 1), 7.07 (m, 1), 7.15-7.46 (m, 21), 9.64 (s, 1) ppm, and NMR (DMSO-d$_6$) 0.87 (m, 6), 1.51 (m, 1), 1.65 (m, 1), 2.03 (m, 1), 3.85 (m, 2), 4.05 (m, 1), 4.20 (m, 1), 5.00 (m, 2), 5.46 (d, 1), 7.00 (m, 1), 7.07 (m, 1), 7.15-7.46 (m, 21), 9.64 (s, 1) ppm; and 2-(3-(amino)methylphenyl)-2-[(1-(1-benzyloxycarbonylamino-3-phenylpropylcarbonyl)amino-2-methylpropyl)(hydroxy)phosphinoyloxy]ethanoic acid, mixture of diastereomers, NMR (CD$_3$OD) 0.98 (m, 6), 1.75 (m, 1), 1.92 (m, 1), 2.18 (m, 1), 2.63 (m, 2), 4.04 (m, 3), 4.15 (m, 1), 5.13 (m, 2), 5.73 (dd, 1), 7.11-7.36 (m, 12), 7.45 (m, 1), 7.53 (s, 1) ppm.

EXAMPLE 11

This example illustrates the preparation of representative pharmaceutical compositions for oral administration containing a compound of the invention, or a pharmaceutically acceptable salt thereof:

| A. | Ingredients | % wt./wt. |
|---|---|---|
| | Compound of the invention | 20.0% |
| | Lactose | 79.5% |
| | Magnesium stearate | 0.5% |

The above ingredients are mixed and dispensed into hard-shell gelatin capsules containing 100 mg each, one capsule would approximate a total daily dosage.

| B. | Ingredients | % wt./wt. |
|---|---|---|
| | Compound of the invention | 20.0% |
| | Magnesium stearate | 0.9% |
| | Starch | 8.6% |
| | Lactose | 69.6% |
| | PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. | Ingredients | |
|---|---|---|
| | Compound of the invention | 0.1 g |
| | Propylene glycol | 20.0 g |
| | Polyethylene glycol 400 | 20.0 g |
| | Polysorbate 80 | 1.0 g |
| | Water | q.s. 100 mL |

The compound of the invention is dissolved in propylene glycol, polyethylene glycol 400 and polysorbate 80. A sufficient quantity of water is then added with stirring to provide 100 mL of the solution which is filtered and bottled.

| D. | Ingredients | % wt./wt. |
|---|---|---|
| | Compound of the invention | 20.0% |
| | Peanut Oil | 78.0% |
| | Span 60 | 2.0% |

The above ingredients are melted, mixed and filled into soft elastic capsules.

| E. | Ingredients | % wt./wt. |
|---|---|---|
| | Compound of the invention | 1.0% |
| | Methyl or carboxymethyl cellulose | 2.0% |
| | 0.9% saline | q.s. 100 mL |

The compound of the invention is dissolved in the cellulose/saline solution, filtered and bottled for use.

EXAMPLE 12

This example illustrates the preparation of a representative pharmaceutical formulation for parenteral administration containing a compound of the invention, or a pharmaceutically acceptable salt thereof:

| Ingredients | |
|---|---|
| Compound of the invention | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a 0.2 m membrane filter and packaged under sterile conditions.

EXAMPLE 13

This example illustrates the preparation of a representative pharmaceutical composition in suppository form containing a compound of the invention, or a pharmaceutically acceptable salt thereof:

| Ingredients | % wt./wt. |
|---|---|
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 14

This example illustrates the preparation of a representative pharmaceutical formulation for insufflation containing a compound of the invention, or a pharmaceutically acceptable salt thereof:

| Ingredients | % wt./wt. |
|---|---|
| Micronized compound of the invention | 1.0% |
| Micronized lactose | 99.0% |

The ingredients are milled, mixed, and packaged in an insufflator equipped with a dosing pump.

EXAMPLE 15

This example illustrates the preparation of a representative pharmaceutical formulation in nebulized form containing a compound of the invention, or a pharmaceutically acceptable salt thereof:

| Ingredients | % wt./wt. |
|---|---|
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

EXAMPLE 16

This example illustrates the preparation of a representative pharmaceutical formulation in aerosol form containing a compound of the invention, or a pharmaceutically acceptable salt thereof:

| Ingredients | % wt./wt. |
|---|---|
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

EXAMPLE 17

In Vitro Assay

The compounds of the invention were tested in an in vitro assay according to the method described in Hendriks et al., "Colorimetric assay for carboxypeptidase N in serum", *Clinica Chimica Acta* (1986), Vol. 157, pp. 103-108 and Zhao et al., "Identification and characterization of two thrombin-activatable fibrinolysis inhibitor isoforms", *Thromb. Haemost*. (1998), Vol. 80, pp. 949-955.

Activation of Plasma Carboxypeptidase B:

The following reagents were mixed together at a total volume of 200 μL:

| | |
|---|---|
| 20 μL plasma carboxypeptidase B (1 mg/mL or 16.67 μM) | final 1.67 μM |
| 10 μL human thrombin (0.2 μM) | final 10 nM |
| 5.3 μL human thrombomodulin (1.89 μM) | final 50 nM |
| 165 μL activation buffer (20 mM HEPES, pH 7.8/150 mM NaCl/5 mM $CaCl_2$) | |

The above mixture was incubated for 15 minutes at ambient temperature. The activation process was stopped by the addition of 2 μl of PPACK, D-Phe-Pro-Arg chloromethylketone (100 μM, final 1.0 μM). The mixture was then diluted 1:36 with the activation buffer containing 0.1% BSA. The resulting diluted mixture was kept on ice.

Assay for Activated Plasma Carboxypeptidase Activity:

The following were mixed:

36 μL of a compound of the invention (1.67×10 μM in 33 mM HEPES, pH 7.8)

12 μL of the activated plasma carboxypeptidase B mixture prepared above (final 33 ng/assay or 15.7 nM)

[35 μM ($IC_{50}$) GEMSA was used as a positive standard]

[DMSO/buffer (final 1%) was used as a blank]

The resulting sample mixture was incubated for 2 minutes at ambient temperature. To the sample mixture was added 12 μL of 5 mM hippuryl-Arg (final 1 mM (=Km)). The resulting sample mixture was incubated at ambient temperature for 30 minutes. At the end of the reaction, the product, hippuric acid, in the sample mixture was converted to a chromogen by adding the following to the mixture:

80 μL of 0.2 M sodium phosphate buffer, pH 8.3

60 μL of 3% cyanuric chloride in dioxane (w/v).

The samples were mixed well and then 150 μL aliquots were transferred to a new well.

Optical density of the samples was measured at 382 nm.

The compounds of the invention, when tested in this assay, demonstrated the ability to inhibit the activity of activated plasma carboxypeptidase B.

EXAMPLE 18

In Vitro Assay

The following in vitro plasma clot lysis assay was conducted according to methods similar to those described in Nagashima et al., "An inhibitor of activated thrombin-activatable fibrinolysis inhibitor potentiates tissue-type plasminogen activator-induced thrombolysis in a rabbit jugular vein thrombolysis model", *Thrombosis Research* (2000), Vol. 98, pp. 333-342.

Human or rabbit platelet-poor plasma was obtained by centrifugation of citrated blood (9:1 with 3.8% sodium citrate, v/v) at 1500 g for 15 minutes at ambient temperature. In a 96-well microtitre plate, 30 μL of citrated plasma was mixed with 50 nM thrombomodulin and various concentrations of inhibitors in 20 mM HEPES, pH 7.0 with 75 mM NaCl and 0.005% TWEEN 80. The mixture was immediately added to another well containing thrombin (final 2.5 NIH units/mL), $CaCl_2$ (final 17 mM) and tissue-type plasminogen activator (final in a range between 0.03-0.07 μg/mL) in separate aliquots. The total volume of the mixture was 120 μL. The absorbance at 405 nm was measured at 37° C. every minute for 1 hour using a SpectraMAX 250 Microplate Spectrophotometer (Molecular Device Corporation, Sunnyvale, Calif.). Lysis time was defined as the time at which the absorbance was one-half of the difference between the plateau reached after clotting and the base-line value achieved at complete lysis.

In order to test the stability of inhibitors in plasma, inhibitors were pre-incubated with plasma in some assays for various times before being tested in the assay.

The compounds of the invention, when tested in this assay, demonstrated the ability to enhance clot lysis induced by tissue-type plasminogen activator both with and without pre-incubation with plasma.

EXAMPLE 19

In Vivo Assay

The following in vivo assay was conducted according to methods similar to those described in Nagashima et al., "An inhibitor of activated thrombin-activatable fibrinolysis inhibitor potentiates tissue-type plasminogen activator-induced thrombolysis in a rabbit jugular vein thrombolysis model", *Thrombosis Research* (2000), Vol. 98, pp. 333-342.

A rabbit jugular vein thrombolysis model was set up as described in Nagashima et al. New Zealand white rabbits (~2.5 kg body weight) were anaesthetized with a mixture of 5 to 8% isofluorane in oxygen and were maintained under 0.5 to 2.5% isofluorane in oxygen. The facial vein, the right and the left marginal ear vein were cannulated for delivery of citrated whole blood, intravenous infusion of compounds of the invention and collection of blood samples, respectively. A thrombotic occlusion was introduced by injecting a mixture of 300 μL autologous citrated whole blood (9:1 with 3.8% sodium citrate) and 80 μl thromboplastin with $Ca^{2+}$ into a 2-cm isolated segment of the jugular vein via the cannula in the facial vein. Ten minutes later, a cotton thread was inserted through the thrombus to hold it in place. The thrombus was matured for 30 minutes prior to re-establishing blood flow and starting the infusion of compounds of the invention. Blood samples were collected in 3.8% citrate (9:1, v/v) and PPACK (1 μM) prior to thrombus formation (denoted as time 0 sample) and 1, 10, 30, 60 and 90 minutes after initiation of administration of the compound to measure the plasma level of the compound. Compounds and vehicles were administered as a bolus injection followed by constant infusion for 90 minutes. At the end of 90 minutes, the thrombus was removed for wet weight measurement.

The animals were divided into 4 groups. Animals in Group 1 received saline only. Animals in Group 2 received tissue-type plasminogen activator (t-PA) only. Animals in Group 3 received t-PA and a compound of the invention. Animals in Group 4 received t-PA and a positive control (a small protein inhibitor of carboxypeptidase). Statistical analysis of the results was performed using the non-parametric Kruskal-Wallis one-way analysis of variance followed by the Mann-Whitney U-test.

The compounds of the invention, when tested in this assay, demonstrated the ability to allow the lysis of the thrombus.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

The invention claimed is:

1. A compound of formula (I):

(I)

wherein:
$R^1$ is hydrogen;
$R^2$ is —SH, —S—C(O)—$R^8$, —P(O)(O$R^5$)$_2$, —P(O)(O$R^5$)$R^6$, —P(O)(O$R^5$)—$R^7$—N($R^6$)$_2$, —P(O)(O$R^5$)—$R^7$—C(O)—$R^8$, —P(O)(O$R^5$)—$R^7$—N($R^5$)—C(O)O$R^8$, or —P(O)(O$R^5$)—$R^7$—N($R^5$)—C(S)—N($R^6$)$_2$;
$R^3$ is tetrazole, —C(O)O$R^6$, or —C(O)O—$R^7$—OC(O)$R^5$;
$R^4$ is phenyl substituted by one or more substituents selected from the group consisting of alkyl, halo, haloalkyl, haloalkoxy, mercapto, alkylthio, phenyl, cycloalkyl, nitro, cyano, —O$R^6$, —N($R^6$)$_2$, —$R^7$—N($R^6$)$_2$, —N($R^6$)—C(O)O$R^8$, —$R^7$—N($R^6$)—C(O)O$R^8$, —N($R^6$)—C(O)—$R^6$, —$R^7$—N($R^6$)—C(O)—$R^6$, —C(O)—N($R^6$)$_2$, —C(O)—$R^7$—N($R^6$)$_2$, —N($R^5$)—C(N$R^5$)—N($R^5$)$_2$, —N($R^5$)—C(O)—N($R^6$)$_2$ and —N($R^5$)—C(O)—$R^7$—N($R^6$_2);
each $R^5$ is independently hydrogen, alkyl or aralkyl;
each $R^6$ is independently hydrogen, alkyl, alkenyl, alkynyl, aryl, aralkyl or aralkenyl;
each $R^7$ is independently cycloalkylene (optionally substituted by alkyl), a straight or branched alkylene chain (optionally substituted by hydroxy, mercapto, alkylthio, aryl, cycloalkyl, —N($R^6$)$_2$, —C(O)O$R^6$, or —C(O)N($R^6$)$_2$), or a straight or branched alkenylene chain (optionally substituted by hydroxy, mercapto, alkylthio, aryl, cycloalkyl, —N($R^6$)$_2$, —C(O)O$R^6$, or —C(O)N($R^6$)$_2$); and
each $R^8$ is independently alkyl, alkenyl, aryl, aralkyl or aralkenyl;

provided that when $R^3$ is —C(O)OH or when $R^4$ is a substituted phenyl, $R^2$ can not be —P(O)(O$R^5$)—$R^7$—N(H)—C(O)O$R^8$;
as a single stereoisomer, a mixture of stereoisomers, or as a racemic mixture of stereoisomers; or a pharmaceutically acceptable salt thereof.

2. The compound of claim 1 wherein:
$R^1$ is hydrogen;
$R^2$ is —SH or —S—C(O)—$R^8$;
$R^3$ is tetrazole, —C(O)O$R^6$ or —C(O)O—$R^7$—OC(O)$R^5$;
$R^4$ is phenyl substituted by one or more substituents selected from the group consisting of alkyl, halo, nitro, cyano, —N($R^6$)$_2$, —$R^7$—N($R^6$)$_2$, —N($R^6$)—C(O)O$R^8$, —$R^7$—N($R^6$)—C(O)O$R^8$, —N($R^6$)—C(O)—$R^6$, —$R^7$—N($R^6$)—C(O)—$R^6$, —C(O)—N($R^6$)$_2$, —C(O)—$R^7$—N($R^6$)$_2$, —N($R^5$)—C(N$R^5$)—N($R^5$)$_2$, —N($R^5$)—C(O)—N($R^6$)$_2$ and —N($R^5$)—C(O)—$R^7$—N($R^6$_2);
each $R^5$ is independently hydrogen, alkyl or aralkyl;
each $R^6$ is independently hydrogen, alkyl, alkenyl, alkynyl, aryl, aralkyl or aralkenyl;
each $R^7$ is independently a straight or branched alkylene chain optionally substituted by hydroxy, mercapto, alkylthio, aryl, cycloalkyl, —N($R^6$)$_2$, —C(O)O$R^6$, or —C(O)N($R^6$)$_2$; and
each $R^8$ is independently alkyl, alkenyl, aryl, aralkyl or aralkenyl.

3. The compound of claim 2 wherein:
$R^1$ is hydrogen;
$R^2$ is —SH or —S—C(O)—$R^8$;
$R^3$ is —C(O)O$R^6$;
$R^4$ is phenyl substituted by one or more substituents selected from the group consisting of halo, nitro, —N($R^6$)$_2$, —$R^7$—N($R^6$)$_2$ and —N($R^5$)—C(N$R^5$)—N($R^5$)$_2$;
each $R^5$ is independently hydrogen, alkyl or aralkyl;
each $R^6$ is independently hydrogen, alkyl, aryl or aralkyl;
$R^7$ is a straight or branched alkylene chain; and
$R^8$ is alkyl, alkenyl, aryl, aralkyl or aralkenyl.

4. The compound of claim 3 selected from the group consisting of the following:
2-(4-guanidinophenyl)-3-mercaptopropanoic acid;
2-(3-guanidinophenyl)-3-mercaptopropanoic acid;
2-(3-aminophenyl)-3-mercaptopropanoic acid; and
2-(2-chloro-5-guanidinophenyl)-3-mercaptopropanoic acid.

5. The compound of claim 1 wherein:
$R^1$ is hydrogen;
$R^2$ is —P(O)(O$R^5$)$_2$, —P(O)(O$R^5$)$R^6$ or —P(O)(O$R^5$)—$R^7$—C(O)—$R^8$;
$R^3$ is tetrazole, —C(O)O$R^6$, or —C(O)O—$R^7$—OC(O)$R^5$;
$R^4$ is phenyl substituted by one or more substituents selected from the group consisting of alkyl, halo, nitro, cyano, —N($R^6$)$_2$, —$R^7$—N($R^6$)$_2$, —N($R^6$)—C(O)O$R^8$, —$R^7$—N($R^6$)—C(O)O$R^8$, —N($R^6$)—C(O)—$R^6$, —$R^7$—N($R^6$)—C(O)—$R^6$, —C(O)—N($R^6$)$_2$, —C(O)—$R^7$—N($R^6$)$_2$, —N($R^5$)—C(N$R^5$)—N($R^5$)$_2$, —N($R^5$)—C(O)—N($R^6$)$_2$ and —N($R^5$)—C(O)—$R^7$—N($R^6$_2);
each $R^5$ is independently hydrogen, alkyl or aralkyl;
each $R^6$ is independently hydrogen, alkyl, alkenyl, alkynyl, aryl, aralkyl or aralkenyl;
each $R^7$ is independently a straight or branched alkylene chain optionally substituted by hydroxy, mercapto, alkylthio, aryl, cycloalkyl, —N($R^6$)$_2$, —C(O)O$R^6$, or —C(O)N($R^6$)$_2$; and each R⁸ is independently alkyl, alkenyl, aryl, aralkyl or aralkenyl.

6. The compound of claim 5 wherein:
R¹ is hydrogen;
R² is —P(O)(OR⁵)₂, —P(O)(OR⁵)R⁶ or —P(O)(OR⁵)—R⁷—C(O)—R⁸;
R³ is —C(O)OR⁶;
R⁴ is phenyl substituted by one or more substituents selected from the group consisting of halo, nitro, —N(R⁶)₂, —R⁷—N(R⁶)₂ and —N(R⁵)—C(NR⁵)—N(R⁵)₂;
each R⁵ is independently hydrogen, alkyl or aralkyl;
each R⁶ is independently hydrogen, alkyl, aryl or aralkyl;
each R⁷ is independently a straight or branched alkylene chain optionally substituted by aryl, —N(R⁶)₂ or —C(O)OR⁶; and
R⁸ is alkyl, alkenyl, aryl, aralkyl or aralkenyl.

7. The compound of claim 6 selected from the group consisting of the following:
2-(3-guanidinophenyl)-3-phosphonopropanoic acid;
2-(3-aminophenyl)-3-((phenyl)(hydroxy)phosphinoyl) propanoic acid;
2-(3-aminophenyl)-3-((4-phenylbutyl)(hydroxy)phosphinoyl)propanoic acid;
2-(3-aminophenyl)-3-((pentyl)(hydroxy)phosphinoyl) propanoic acid;
2-(3-guanidinophenyl)-3-((phenyl)(hydroxy)phosphinoyl)propanoic acid;
2-(3-guanidinophenyl)-3-((4-phenylbutyl)(hydroxy)phosphinoyl)propanoic acid;
2-(3-guanidinophenyl)-3-((pentyl)(hydroxy)phosphinoyl) propanoic acid;
2-(3-guanidinophenyl)-3-((4-methylpentyl)(hydroxy) phosphinoyl)propanoic acid;
2-(3-guanidinophenyl)-3-((3-phenylpropyl)(hydroxy) phosphinoyl)propanoic acid;
2-(3-guanidinophenyl)-3-((3-phenylprop-2-enyl)(hydroxy)phosphinoyl)propanoic acid;
2-(3-guanidinophenyl)-3-((phenylmethyl)(hydroxy)phosphinoyl)propanoic acid;
2-(3-guanidinophenyl)-3-((pentyl)(hydroxy)phosphinoyl) propanoic acid methyl ester;
2-(3-guanidinophenyl)-3-((ethyl)(hydroxy)phosphinoyl) propanoic acid;
2-(3-guanidinophenyl)-3-((2-phenylethyl)(hydroxy)phosphinoyl)propanoic acid; and
2-(3-guanidinophenyl)-3-((2-(methylcarbonyl)ethyl)(hydroxy)phosphinoyl)propanoic acid.

8. The compound of claim 1 wherein:
R¹ is hydrogen;
R² is —P(O)(OR⁵)—R⁷—N(R⁵)—C(O)OR⁸;
R³ is —C(O)OR⁶ (where R⁶ is alkyl, aryl or aralkyl);
R⁴ is phenyl substituted by one or more substituents selected from the group consisting of alkyl, halo, nitro, cyano, —N(R⁶)₂, —R⁷—N(R⁶)₂, —N(R⁶)—C(O)OR⁸, —R⁷—N(R⁶)—C(O)OR⁸, —N(R⁶)—C(O)—R⁶, —R⁷—N(R⁶)—C(O)—R⁶, —C(O)—N(R⁶)₂, —C(O)—R⁷—N(R⁶)₂, —N(R⁵)—C(NR⁵)—N(R⁵)₂, —N(R⁵)—C(O)—N(R⁶)₂ and —N(R⁵)—C(O)—R⁷—N(R⁶₂) where each R⁶ is independently hydrogen, alkyl, aryl or aralkyl;
each R⁵ is independently hydrogen, alkyl or aralkyl;
each R⁷ is a straight or branched alkylene chain optionally substituted by aryl, —N(R⁶)₂ or —C(O)OR⁶; and
each R⁸ is independently alkyl, alkenyl, aryl, aralkyl or aralkenyl.

9. The compound of claim 8 selected from the group consisting of the following:
2-(3-(t-butoxycarbonylamino)methylphenyl)-3-((1-(benzyloxycarbonyl)amino-2-methylpropyl)(hydroxy) phosphinoyl)propanoic acid t-butyl ester; and
2-(3-(t-butoxycarbonylamino)methylphenyl)-3-((1-(benzyloxycarbonyl)amino-2-methylpropyl)(ethoxy)phosphinoyl)propanoic acid t-butyl ester.

10. The compound of claim 1 wherein:
R¹ is hydrogen;
R² is —P(O)(OR⁵)—R⁷—N(R⁶)₂ or —P(O)(OR⁵)—R⁷—N(R⁵)—C(S)—N(R⁶)₂;
R³ is tetrazole, —C(O)OR⁶, or —C(O)O—R⁷—OC(O)R⁵;
R⁴ is phenyl substituted by one or more substituents selected from the group consisting of alkyl, halo, nitro, cyano, —N(R⁶)₂, —R⁷—N(R⁶)₂, —N(R⁶)—C(O)OR⁸, —R⁷—N(R⁶)—C(O)OR⁸, —N(R⁶)—C(O)—R⁶, —R⁷—N(R⁶)—C(O)—R⁶, —C(O)—N(R⁶)₂, —C(O)—R⁷—N(R⁶)₂, —N(R⁵)—C(NR⁵)—N(R⁵)₂, —N(R⁵)—C(O)—N(R⁶)₂ and —N(R⁵)—C(O)—R⁷—N(R⁶₂);
each R⁵ is independently hydrogen, alkyl or aralkyl;
each R⁶ is independently hydrogen, alkyl, alkenyl, alkynyl, aryl, aralkyl or aralkenyl;
each R⁷ is a straight or branched alkylene chain optionally substituted by hydroxy, mercapto, alkylthio, aryl, cycloalkyl, —N(R⁶)₂, —C(O)OR⁶, or —C(O)N(R⁶)₂; and
each R⁸ is independently alkyl, alkenyl, aryl, aralkyl or aralkenyl.

11. The compound of claim 10 selected from the group consisting of the following:
2-(3-(t-butoxycarbonylamino)methylphenyl)-3-((1-amino-2-methylpropyl)(hydroxy)-phosphinoyl)propanoic acid t-butyl ester; and
2-(3-(t-butoxycarbonylamino)methylphenyl)-3-((1-amino-2-methylpropyl)(ethoxy)-phosphinoyl)propanoic acid t-butyl ester.

12. A compound of formula (I):

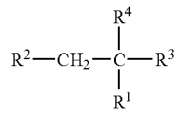

(I)

wherein:
R¹ is hydrogen;
R² is —P(O)(OR⁵)—R⁷—N(R⁵)—C(O)OR⁸;
R³ is —C(O)OR⁶;
R⁴ is unsubstituted phenyl;
each R⁵ is independently hydrogen, alkyl or aralkyl;
each R⁶ is independently hydrogen, alkyl, alkenyl, alkynyl, aryl, aralkyl or aralkenyl;
each R⁷ is a straight or branched alkylene chain optionally substituted by aryl, —N(R⁶)₂ or —C(O)OR⁶; and
R⁸ is alkyl, alkenyl, aryl, aralkyl or aralkenyl.

13. The compound of claim 12 selected from the group consisting of the following:
2-phenyl-3-((1-(benzyloxycarbonyl)amino-2-methylpropyl)(hydroxy)phosphinoyl)-propanoic acid.

14. A pharmaceutical composition comprising a pharmaceutically acceptable excipient and a compound of formula (I) according to claim 1.

* * * * *